(12) United States Patent
Chen et al.

(10) Patent No.: US 10,697,025 B2
(45) Date of Patent: *Jun. 30, 2020

(54) METHODS OF STRATIFYING PATIENTS FOR TREATMENT WITH RETINOIC ACID RECEPTOR-ALPHA AGONISTS

(71) Applicant: Syros Pharmaceuticals, Inc., Cambridge, MA (US)

(72) Inventors: Mei W. Chen, Cambridge, MA (US); Cindy Collins, Cambridge, MA (US); Matthew L. Eaton, Cambridge, MA (US); Matthew G. Guenther, Boston, MA (US); Nan Ke, Malden, MA (US); Jeremy Lopez, Allston, MA (US); Michael R. McKeown, Brookline, MA (US); David A. Orlando, Somerville, MA (US)

(73) Assignee: Syros Pharmaceuticals, Inc., Cambridge, MA (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/899,629

(22) Filed: Feb. 20, 2018

(65) Prior Publication Data

US 2018/0187271 A1 Jul. 5, 2018

Related U.S. Application Data

(63) Continuation of application No. 15/799,519, filed on Oct. 31, 2017, now Pat. No. 10,167,518, which is a continuation of application No. 15/172,045, filed on Jun. 2, 2016, now Pat. No. 9,845,508, which is a continuation of application No. PCT/US2016/025256, filed on Mar. 31, 2016.

(60) Provisional application No. 62/268,203, filed on Dec. 16, 2015, provisional application No. 62/140,999, filed on Mar. 31, 2015.

(51) Int. Cl.

| | |
|---|---|
| *A61K 31/165* | (2006.01) |
| *A61K 31/167* | (2006.01) |
| *C12Q 1/6886* | (2018.01) |
| *A61K 31/166* | (2006.01) |
| *A61K 31/196* | (2006.01) |
| *A61K 31/192* | (2006.01) |
| *A61K 31/195* | (2006.01) |

(52) U.S. Cl.
CPC .......... *C12Q 1/6886* (2013.01); *A61K 31/165* (2013.01); *A61K 31/166* (2013.01); *A61K 31/167* (2013.01); *A61K 31/192* (2013.01); *A61K 31/195* (2013.01); *A61K 31/196* (2013.01); *C12Q 2600/106* (2013.01); *C12Q 2600/156* (2013.01); *C12Q 2600/158* (2013.01)

(58) Field of Classification Search
CPC .................................................. A61K 31/165
See application file for complete search history.

(56) References Cited

U.S. PATENT DOCUMENTS

| | | |
|---|---|---|
| 4,703,110 A | 10/1987 | Shudo |
| 5,081,271 A | 1/1992 | Shudo |
| 5,089,509 A | 2/1992 | Chandraratna |
| 5,455,265 A | 10/1995 | Chandraratna |
| 5,759,785 A | 6/1998 | Tsai et al. |
| 5,856,490 A | 1/1999 | Teng et al. |
| 5,965,606 A | 10/1999 | Teng et al. |
| 6,063,797 A | 5/2000 | Fesus et al. |
| 6,071,924 A | 6/2000 | Campochiaro et al. |
| 6,075,032 A | 6/2000 | Campochiaro et al. |
| 6,187,950 B1 | 2/2001 | Song et al. |
| 6,355,669 B1 | 3/2002 | Yamauchi et al. |
| 6,358,995 B1 | 3/2002 | Tagami et al. |
| 6,387,950 B2 | 5/2002 | Nehme et al. |
| 8,030,031 B2 | 10/2011 | Kopreski |
| 8,669,058 B2 | 3/2014 | Liew |
| 9,181,580 B2 | 11/2015 | Young et al. |
| 10,167,518 B2 | 1/2019 | Chen et al. |
| 2010/0048708 A1 | 2/2010 | Ekimoto |
| 2010/0099084 A1 | 4/2010 | Albitar |
| 2014/0051760 A1 | 2/2014 | Miller et al. |
| 2014/0272956 A1 | 9/2014 | Huang et al. |
| 2016/0355888 A1 | 12/2016 | Chen et al. |
| 2017/0292165 A1 | 10/2017 | McKeown et al. |
| 2018/0087115 A1 | 3/2018 | Chen et al. |
| 2018/0155796 A1 | 6/2018 | McKeown et al. |
| 2019/0249259 A1 | 8/2019 | McKeown et al. |

FOREIGN PATENT DOCUMENTS

| | | |
|---|---|---|
| WO | WO-2003025171 A2 | 3/2003 |
| WO | WO-2013185105 A1 | 12/2013 |
| WO | WO-2014/066848 A1 | 5/2014 |

(Continued)

OTHER PUBLICATIONS

Alsafadi et al. "Retinoic acid receptor alpha amplifications and retinoic acid sensitivity in breast cancers." *Clin Breast Cancer.* Oct. 2013;13(5):401-8.

(Continued)

*Primary Examiner* — Yong S. Chong
(74) *Attorney, Agent, or Firm* — Choate, Hall & Stewart LLP; Brenda Herschbach Jarrell; Janet M. Tse

(57) ABSTRACT

The invention provides methods that define cellular populations that are sensitive to RARA agonists and identify patient subgroups that will benefit from treatment with RARA agonists. The invention also provides packaged pharmaceutical compositions that comprise a RARA agonist and instructions for determining if such agonist is suitable for use in treatment.

27 Claims, 47 Drawing Sheets

Specification includes a Sequence Listing.

(56) References Cited

FOREIGN PATENT DOCUMENTS

| WO | WO-2015085172 A2 | 6/2015 |
|---|---|---|
| WO | WO-2015101618 A1 | 7/2015 |
| WO | WO-2016144976 A1 | 9/2016 |
| WO | WO-2016161107 A1 | 10/2016 |
| WO | WO-2017/091762 A1 | 6/2017 |
| WO | WO-2017/177167 A1 | 10/2017 |
| WO | WO-2018/067946 A1 | 4/2018 |
| WO | WO-2018/136961 A1 | 7/2018 |

OTHER PUBLICATIONS

Asleson et al. "Amplification of the RARA gene in acutte myeloid leukemia: significant finding or coincidental observation?" Cancer Genetics and Cytogenetics (2010) vol. 202 pp. 33-37.

Baljevic et al. "Telomere Length Recovery: A Strong Predictor of Overall Survival in Acute Promyelocytic Leukemia." Acta Haematol. 2016;136(4):210-218.

Bruyère et al. "Concomitant and successive amplifications of MYC in APL-like leukemia." *Cancer Genet Cytogenet*. Feb. 2010;197(1):75-80.

Cao et al. "Oridonin stabilizes retinoic acid receptor alpha through ROS-activated NF-?B signaling." BMC Cancer. Apr. 10, 2015;15:248.

Elias et al. "Immune evasion by oncogenic proteins of acute myeloid leukemia." Blood. Mar. 6, 2014;123(10):1535-43.

Fang et al. Inhibition of all-trans-retinoic acid-induced proteasome activation potentiates the differentiating effect of retinoid in acute myeloid leukemia cells. *Mol Carcinog*. Jan. 2011;50(1):24-35.

Fang et al. "PML-RARa modulates the vascular signature of extracellular vesicles released by acute promyelocytic leukemia cells." Angiogenesis. Jan. 2016;19(1):25-38.

Fu et al. "Clinical significance of lymphoid enhancer-binding factor 1 expression in acute myeloid leukemia." *Leuk Lymphoma*. Feb. 2014;55(2):371-7.

Gao et al. "PML(NLS(−)) inhibits cell apoptosis and promotes proliferation in HL-60 cells." Int J Med Sci. 2013;10(5):498-507.

Glynn et al. "17q12-21—the pursuit of targeted therapy in breast cancer." Cancer Treat Rev. May 2010;36(3):224-9.

Gruver et al. "Modified array-based comparative genomic hybridization detects cryptic and variant PML-RARA rearrangements in acute promyelocytic leukemia lacking classic translocations." Diagn Mol Pathol. Mar. 2013;22(1):10-21.

Hasan et al. "Analysis of t(15;17) chromosomal breakpoint sequences in therapy-related versus de novo acute promyelocytic leukemia: association of DNA breaks with specific DNA motifs at PML and RARA loci." Genes Chromosomes Cancer. Aug. 2010;49(8):726-32.

Hashimoto et al. "Development of Reverse Transcription Loop-Mediated Isothermal Amplification for Simple and Rapid Detection of Promyelocytic Leukemia-Retinoic Acid Receptor α mRNA." Yonago Acta Med. Dec. 26, 2015;59(4):262-269.

Hu et al. "Effect of recombinant adenovirus carrying NLS-RARalpha gene on the proliferation of HL-60 cell and the differentiation of HL-60 cells induced by ATRA and relevant mechanism." Sichuan Da Xue Xue Bao Yi Xue Ban. Nov. 2013;44(6):897-901. Chinese.

Hu et al. "NLS-RARa promotes proliferation and inhibits differentiation in HL-60 cells." *Int J Med Sci*. Jan. 16, 2014;11(3):247-54.

Humbert et al. "The tumor suppressor gene DAPK2 is induced by the myeloid transcription factors PU.1 and C/EBP? during granulocytic differentiation but repressed by PML-RAR? in APL." J Leukoc Biol. Jan. 2014;95(1):83-93.

International Search Report and Written Opinion for corresponding International Application No. PCT/US2017/026657 dated Aug. 28, 2017.

Iwasaki et al. "FIP1L1 presence in FIP1L1-RARA or FIP1L1-PDGFRA differentially contributes to the pathogenesis of distinct types of leukemia." Ann Hematol. Sep. 2014;93(9):1473-81.

Jezísková et al. "A case of a novel PML/RARA short fusion transcript with truncated transcription variant 2 of the RARA gene." Mol Diagn Ther. Apr. 1, 2010;14(2):113-7.

Jo et al. "Korean red ginseng extract induces proliferation to differentiation transition of human acute promyelocytic leukemia cells via MYC-SKP2-CDKN1B axis." J Ethnopharmacol. Nov. 25, 2013;150(2):700-7.

Johnson et al. "An Attractive future for differentiation therapy in AML". Blood Reviews, 2015, pp. 263-268.

Kunter et al. "A truncation mutant of Csf3r cooperates with PML-RAR? to induce acute myeloid leukemia in mice." Exp Hematol. Dec. 2011;39(12):1136-43.

Lai et al. "Unusual acute promyelocytic leukemia following de novo renal transplant: case report and literature review." *Clin Nephrol*. Feb. 2011;75 Suppl 1:27-31.

Laursen et al. "Epigenetic regulation by RAR? maintains ligand-independent transcriptional activity." Nucleic Acids Res. Jan. 2012;40(1):102-15.

Lewis et al. "Microgranular variant of acute promyelocytic leukemia with normal conventional cytogenetics, negative PML/RARA Fish and positive PML/RARA transcripts by RT-PCR." Cancer Genet. Sep. 2011;204(9):522-3.

Li Z et al. FTO Plays an Oncogenic Role in Acute Myeloid Leukemia as a N6-Methyladenosine RNA Demethylase. Cancer Cell Jan. 9, 2017;31(1):127-141. doi: 10.1016/j.ccell.2016.11.017.

Liu et al. "Tetra-arsenic tetra-sulfide (As4S 4) promotes apoptosis in retinoid acid-resistant human acute promyelocytic leukemic NB4-R1 cells through downregulation of SET protein." Tumour Biol. Apr. 2014;35(4):3421-30.

Luo et al. "Effect of siRNA targeting PML-RARa fusion gene on activity of the acute promyelocytic leukemia cell line NB4]." *Sheng Wu Yi Xue Gong Cheng Xue Za Zhi*. Aug. 2014;31(4):850-4. Chinese.

Marchwicka et al. "Regulation of vitamin D receptor expression by retinoic acid receptor alpha in acute myeloid leukemia cells." J Steroid Biochem Mol Biol. May 2016;159:121-30.

Martin-Subero et al. "Amplification of ERBB2, RARA, and TOP2A genes in myelodysplastic syndrome transforming to acute myeloid leukemia" Cancer Genetics and Cytogenetics (2001) vol. 127 pp. 174-176.

Menezes et al. "FIP1L1/RARA with breakpoint at FIP1L1 intron 13: a variant translocation in acute promyelocytic leukemia." Haematologica. Oct. 2011;96(10):1565-6.

Morikawa et al. "All-trans retinoic acid displays multiple effects on the growth, lipogenesis and adipokine gene expression of AML-I preadipocyte cell line." Cell Biol Int. Jan. 2013;37(1):36-46.

Occhionorelli et al. "The self-association coiled-coil domain of PML is sufficient for the oncogenic conversion of the retinoic acid receptor (RAR) alpha." Leukemia. May 2011;25(5):814-20.

Oh et al. "Acute promyelocytic leukemia with a rare PML exon 4/ RARA exon 3 fusion transcript variant." Acta Haematol. 2013;130(3):176-80.

Perri et al. "BCL-xL/MCL-1 inhibition and RAR? antagonism work cooperatively in human HL60 leukemia cells." Exp Cell Res. Oct. 1, 2014;327(2):183-91.

Polampalli et al. "Role of RT-PCR and FISH in diagnosis and monitoring of acute promyelocytic leukemia." Indian J Cancer. Jan.-Mar. 2011;48(1):60-7.

Pu et al. "The First Switched Time of PML/RARα Fusion Gene in Patients with Acute Promyelocytic Leukemia and Its Clinical Significance." Zhongguo Shi Yan Xue Ye Xue Za Zhi. Dec. 2015;23(6):1551-5. Chinese.

Qi et al. "The PML gene of the PML-RAR? V-form fusion transcript breaks within exon 6." Acta Haematol. 2011;126(4):216-9.

Saeed et al. "Chromatin accessibility, p300, and histone acetylation define PML-RARa and AML1-ETO binding sites in acute myeloid leukemia." Blood. Oct. 11, 2012;120(15):3058-68.

Saito et al. "DIC Complicating APL Successfully Treated With Recombinant Thrombomodulin Alfa." J Pediatr Hematol Oncol. Aug. 2016;38(6):e189-90.

(56) References Cited

OTHER PUBLICATIONS

Sanford et al. "Tamibarotene in patients with acute promyelocytic Leukaemia relapsing after treatment with all-trans retinoic acid and arsenic trioxide". British Journal of Haematology, 2015, pp. 471-476.
Seshire et al. "Direct interaction of PU.1 with oncogenic transcription factors reduces its serine phosphorylation and promoter binding." Leukemia. Jun. 2012;26(6):1338-47. Erratum in: Leukemia. Nov. 2012;26(11):2445-6.
Shigeto et al. "Rapid diagnosis of acute promyelocytic leukemia with the PML-RARA fusion gene using a combination of droplet-reverse transcription-polymerase chain reaction and instant-quality fluorescence in situ hybridization." Clin Chim Acta. Jan. 30, 2016;453:38-41.
Shimomura et al. "New variant of acute promyelocytic leukemia with IRF2BP2-RARA fusion." Cancer Sci. Aug. 2016;107(8):1165-8.
Soriani et al. "PML/RAR-alpha fusion transcript and polyploidy in acute promyelocytic leukemia without t(15;17)." *Leuk Res.* Sep. 2010;34(9):e261-3.
Sueki et al. "Rapid detection of PML-RARA fusion gene by novel high-speed droplet-reverse transcriptase-polymerase chain reaction: possibility for molecular diagnosis without lagging behind the morphological analyses." *Clin Chim Acta.* Jan. 16, 2013;415:276-8.
Tian et al."Arsenic sulfide promotes apoptosis in retinoid acid resistant human acute promyelocytic leukemic NB4-R1 cells through downregulation of SET protein." PLoS One. Jan. 13, 2014;9(1):e83184.
Valleron et al. "Specific small nucleolar RNA expression profiles in acute leukemia." *Leukemia.* Sep. 2012;26(9):2052-60.
Vourtsis et al. "Effect of an all-trans-retinoic acid conjugate with spermine on viability of human prostate cancer and endothelial cells in vitro and angiogenesis in vivo." Eur J Pharmacol. Jan. 5, 2013;698(1-3):122-30.
Walz et al."Atypical mRNA fusions in PML-RARA positive, RARA-PML negative acute promyelocytic leukemia." Genes Chromosomes Cancer. May 2010;49(5):471-9.
Welch et al. "PML-RARA can increase hematopoietic self-renewal without causing a myeloproliferative disease in mice." *J Clin Invest.* Apr. 2011;121(4):1636-45.
Xu et al. "All-trans retinoic acid is capable of inducing folate receptor ? expression in KG-1 cells."Tumour Biol. Dec. 2010;31(6):589-95.
Yamamoto et al. "BCOR as a novel fusion partner of retinoic acid receptor alpha in a t(X;17)(p. 11;q12) variant of acute promyelocytic leukemia." *Blood.* Nov. 18, 2010;116(20):4274-83.
Yamamoto et al. "Persistent Hypoplastic Acute Promyelocytic Leukemia with a Novel Chromosomal Abnormality of 46, XY, t(15;17), t(9;11)(q13;p. 13)." J Clin Exp Hematop. 2015;55(2):71-6.
Zhang et al. "Arsenic trioxide suppresses transcription of hTERT through down-regulation of multiple transcription factors in HL-60 leukemia cells." *Toxicol Lett.* Jan. 22, 2015;232(2):481-9.
Zhu et al. "The significance of low PU.1 expression in patients with acute promyelocytic leukemia." J Hematol Oncol. May 8, 2012;5:22.
Zou et al. "Regulation of the hematopoietic cell kinase (HCK) by PML/RARα and PU.1 in acute promyelocytic leukemia." *Leuk Res.* Feb. 2012;36(2):219-23.
Garattini et al. "Retinoids and breast cancer: from basic studies to the clinic and back again", Cancer Treat Rev. vol. 40, pp. 739-749, 2014.
Garattini et al. "Retinoids and breast cancer: new clues to increase their activity and selectivity", Breast Cancer Res. vol. 14: 111, pp. 1-2, 2012.
International Search Report and Written Opinion from corresponding International Application No. PCT/US2016/025256 dated Aug. 8, 2016.
Paroni et al. "Synergistic antitumor activity of lapatinib and retinoids on a novel subtype of breast cancer with coamplification of ERBB2 and RARA", Oncogene. vol. 31, pp. 3431-3443, 2011.
Hashimoto et al. "Development of Reverse Transcription Loop-Mediated Isothermal Amplification for Simple and Rapid Detection of Promyelocytic Leukemia-Retinoic Acid Receptor α mRNA." Yonago Acta Med. Dec. 26, 2016;59(4):262-269.
Becker, H. et al., Favorable Prognostic Impact of NPM1 Mutations in Older Patients With Cytogenetically Normal De Novo Acute Myeloid Leukemia and Associated Gene- and MicroRNA-Expression Signatures: A Cancer and Leukemia Group B Study, Journal of Clinical Oncology, 28(4):596-604 (2010).
Centritto, F. et al., Cellular and molecular determinants of all-trans retinoic acid sensitivity in breast cancer: Luminal phenotype and RARα expression, EMBO Molecular Medicine, 7(7):950-972 (2015).
Falini, B. et al., Acute myeloid leukemia with mutated nucleophosmin (NPM1): is it a distinct entity?, Blood, 117(4):1109-1120 (2011).
Frohling, S. et al., Cytogenetics and age are major determinants of outcome in intensively treated acute myeloid leukemia patients older than 60 years: results from AMLSG trial AML HD98-B, Blood, 108(10):3280-3288 (2006).
Guo, Y. et al., How is mRNA expression predictive for protein expression? A correlation study on human circulating monocytes, Acta Biochim Biophys Sin, 40(5):426-436 (2008).
Johansson, H. et al., Retinoic acid receptor alpha is associated with tamoxifen resistance in breast cancer, Nature Communications, 4(2175): 10 pages (2013).
Thiede, C. et al., Prevalence and prognostic impact of NPM1 mutations in 1485 adult patients with acute myeloid leukemia (AML), Blood, 107(10): 4011-4020 (2006).
Bonhoure, N. et al., Quantifying ChIP-seq data: a spiking method providing an internal reference for sample-to-sample normalization, Genome Res, 24(7):1157-68 (2014).
Burnett. A. et al., The impact on outcome of the addition of all-trans retinoic acid to intensive chemotherapy in younger patients with nonacute promyelocytic acute myeloid leukemia: overall results and results in genotypic subgroups defined by mutations in NPM1, FLT3, and CEBPA, Blood, 115:948-956 (2010).
Chapuy, B. et al., Discovery and characterization of super-enhancer-associated dependencies in diffuse large B cell lymphoma, Cancer Cell, 24(6):777-90 (2013).
Chelbi-Alix, MK and Pelicano, L., Retinoic acid and interferon signaling cross talk in normal and RA-resistant APL cells, Leukemia, 13(8):1167-74 (1999).
De Weers, M. et al., Daratumumab, a novel therapeutic human CD38 monoclonal antibody, induces killing of multiple myeloma and other hematological tumors. J Immunol, 186(3):1840-8 (2011).
Delmore, JE et al., BET bromodomain inhibition as a therapeutic strategy to target c-Myc, Cell, 146(6):904-17 (2011).
Dos Santos, C. et al., Anti-Leukemic Activity of Daratumumab in Acute Myeloid Leukemia Cells and Patient-Derived Xenografts, Blood, 124:2312-2312 (2014).
Encode Project Consortium, An integrated encyclopedia of DNA elements in the human genome, Nature, 489(7414):57-74 (2012).
Furey, TS, ChIP-seq and beyond: new and improved methodologies to detect and characterize protein-DNA interactions, Nat Rev Genet, 13(12):840-52 (2012).
Gallagher, R. et al,, Expression of Retinoic Acid Receptor-α mRNA in Human Leukemia Cells with Variable Responsiveness to Retinoic Acid, Leukemia, 3(11):789-795 (1989).
Hah, N. et al., Inflammation-sensitive super enhancers form domains of coordinately regulated enhancer RNAs, Proc Natl Acad Sci USA, 112(3):E297-302 (2015).
Hnisz, D. et al., Super-Enhancers in the Control of Cell Identity and Disease, Cell, 155:934-947 (2013).
Kanno, J. et al., "Per cell" normalization method for mRNA measurement by quantitative PCR and microarrays, BMC Genomics, 7:64 (2006).
Largman, C. et al., Expression of Retinoic Acid Receptor Alpha mRNA in Human Leukemia Cells, Blood, 74(1):99-102 (1989).
Lokhorst, HM et al., Targeting CD38 with Daratumumab Monotherapy in Multiple Myeloma, N Engl J Med, 373(13):1207-19 (2015).
Lovén, J. et al., Revisiting global gene expression analysis, Cell, 151(3):476-82 (2012).
Lovén, J. et al., Selective inhibition of tumor oncogenes by disruption of super-enhancers, Cell, 153(2):320-34 (2013).

(56) References Cited

OTHER PUBLICATIONS

Mehta, K. and Cheema, S., Retinoid-mediated signaling pathways in CD38 antigen expression in myeloid leukemia cells, Leuk Lymphoma, 32(5-6):441-9 (1999).
Mercader, J. et al., Remodeling of white adipose tissue after retinoic acid administration in mice, Endocrinology, 147(11):5325-32 (2006).
Metzker, ML, Sequencing technologies—the next generation, Nat Rev Genet, 11(1):31-46 (2010).
Miwako, I. et al., Tamibarotene, Drugs Today (Bart), 43(8):563-568 abstract only (2007).
Nazha, A. et al., The addition of all-trans retinoic acid to chemotherapy may not improve the outcome of patient with NPM1 mutated acute myeloid leukemia, Frontiers in Oncology, 3(2):1-5 (2013).
Niederreither, K., Retinoic acid in development: towards an integrated view, Nat Rev Genet, 9(7):541-53 (2008).
Nijhof, IS et al., CD38 expression and complement inhibitors affect response and resistance to daratumumab therapy in myeloma, Blood, 128(7):959-70 (2016).
Orlando, DA et al., Quantitative ChIP-Seq normalization reveals global modulation of the epigenome, Cell Rep, 9(3):1163-70 (2014).
Park, PJ, ChIP-seq: advantages and challenges of a maturing technology, Nat Rev Genet, 10(10):669-80 (2009).
Parrado et al. ("Alterations of the retinoic acid receptor .alpha. (RARA.alpha.) gene in myeloid and lymphoid malignancies" British Journal of Haematology, 1999, 104,738-741).
Pogosova-Agadjanyan, E. et al., The Prognostic Significance of IRF8 Transcripts in Adult Patients with Acute Myeloid Leukemia, PLOS One, 8(8):e70812, 13 pages (2013).
Pott, S. and Lieb, JD, What are super-enhancers? Nat Genet, 47(1):8-12 (2015).
Qian, Q. et al., Treatment prospects for autosomal-dominant polycystic kidney disease, Kidney Int, 59(6):2005-22 (2001).
Redonnet, A. et al,. Relationship between peroxisome proliferator-activated receptor gamma and retinoic acid receptor alpha gene expression in obese human adipose tissue, Int J Obes Relat Metab Disord, 26(7):920-7 (2002).
Robertson, K. et al., Retinoic Acid Receptors in Myeloid Leukemia: Characterization of Receptors in Retinoic Acid-Resistant K-562 Cells, Blood, 77(2):340-347 (1991).
Schlenk, R. et al., All-trans retinoic acid as adjunct to intensive treatment in younger adult patients with acute myeloid leukemia: results of the randomized AMLSG 07-04 study, Ann Hematol, 95:1931-1942 (2016).
Schlenk, R. et al., Gene mutations and response to treatment with all-trans retinoic acid in elderly patients with acute myeloid leukemia. Results from the AMLSG Trial MAL HD98B, Haematologica, 94(1):54-60 (2009).
Sharma, A. et al., Constitutive IRF8 expression inhibits AML by activation of repressed immune response signaling, Leukemia, 29(1):157-68 (2015).
Smith, E. and Shilatifard, A., Enhancer biology and enhanceropathies, Nat Struct Mol Biol, 21(3):210-9 (2014).
Smits, EL et al., Interferon α may be back on track to treat acute myeloid leukemia, Oncoimmunology, 2(4):e23619 (2013).
Sverdlov, E.D. et al., Adult stem cells and other residents of cancer. Part II. Molecular genetics, microbiology and virology. Received on Mar. 25, 2015, found on Internet: https//cyberleninka.ru/article/n/vzroslye-stvolvye-kletki-i-drugie-rezidenty-raka-chast-ii, entire document (Dec. 11, 2019). Non-English Only.
Takahashi et al. ("Induced Differentiation of Human Myeloid Leukemia Cells into M2 Macrophages by Combined Treatment with Retinoic Acid and 1.alpha.,25-Dihydroxyvitamin D3" PLOS One, Nov. 2014, vol. 9, issue 11, 1-9).
Tamura, T. et al., Regulation of myelopoiesis by the transcription factor IRF8, Int J. Hematol, 101:342-351 (2015).
Uruno, A. et al., All-trans retinoic acid and a novel synthetic retinoid tamibarotene (Am80) differentially regulate CD38 expression in human leukemia HL-60 cells: possible involvement of protein kinase C-delta, J Leukoc Biol, 90(2):235-47 (2011).
Van De Peppel, J. et al., Monitoring global messenger RNA changes in externally controlled microarray experiments, EMBO Rep, 4(4):387-93 (2003).
Wang, C. et al., Expression of a Retinoic Acid Receptor Gene in Myeloid Leukemia Cells, Leukemia, 3(4):264-269 (1989).
Written Opinion for PCT/US2016/025256, 8 pages (dated Aug. 8, 2016).
Written Opinion for PCT/US2017/026657, 12 pages (dated Aug. 28, 2017).
Yang, J. et al., Cutting edge: IRF8 regulates Bax transcription in vivo in primary myeloid cells, J Immunol, 187(9):4426-30 (2011).
Yuan et al. ("A112, a tamibarotene dimethylaminoethyl ester, may inhibit human leukemia cell growth more potently than tamibarotene" Leukemia & Lymphoma,Feb. 2012, 53, 2, 295-304).
U.S. Appl. No. 15/172,045, filed Jun. 2, 2016, Patented, U.S. Pat. No. 9,845,508.
U.S. Appl. No. 15/582,311, filed Apr. 28, 2017, Patented, U.S. Pat. No. 9,868,994.
U.S. Appl. No. 15/799,519, filed Oct. 31, 2017, Patented, U.S. Pat. No. 10,167,518.
U.S. Appl. No. 15/828,719, filed Dec. 1, 2017, Patented, U.S. Pat. No. 10,240,210.
U.S. Appl. No. 16/247,362, filed Jan. 14, 2019, Pending.

FIG. 3A

| Source | Cell Type | RARA:DIFF | Malat1:DIFF | RARA/MALAT1 | log 10 |
|---|---|---|---|---|---|
| Breast | Metastatic Frozen | 1226.568 | 48.292 | 25.39898948 | 1.404816 |
| AML | Primary | 19.162 | 0.76 | 25.21315789 | 1.401627 |
| Breast | Tumor_Frozen | 256.211 | 12.677 | 20.21069654 | 1.305581 |
| Breast | Normal_Frozen | 1367.235 | 74.627 | 18.32091602 | 1.262947 |
| Blood | Common Myeloid Progenitor (Donor A) | 9.027 | 0.503 | 17.94632207 | 1.253975 |
| Breast | SKBR3 | 594.291 | 43.216 | 13.75164291 | 1.138355 |
| Breast | AU565 | 976.26 | 80.64 | 12.10639881 | 1.083015 |
| Breast | Metastatic Frozen | 263.614 | 25.869 | 10.19034365 | 1.008189 |
| Breast | Tumor_Frozen | 182.584 | 18.866 | 9.67793915 | 0.985783 |
| Breast | Tumor_Frozen | -41.672 | -4.327 | 9.63069101 | 0.983657 |
| Breast | Normal_Frozen | 753.355 | 82.365 | 9.146542828 | 0.961257 |
| Breast | Tumor_Frozen | 275.368 | 30.811 | 8.937327578 | 0.951208 |
| Blood | PBMC | 91.211 | 10.568 | 8.630866768 | 0.936054 |
| Kidney | NHK | 356.034 | 45.17 | 7.882089883 | 0.896641 |
| AML | Patient_Normal | 26.661 | 3.447 | 7.734551784 | 0.888435 |
| Lung | Primary | 236.588 | 33.079 | 7.152211373 | 0.85444 |
| Blood | CD4+ | 348.696 | 49.011 | 7.114647732 | 0.852153 |
| Heart | Right Ventricle | 196.243 | 27.836 | 7.04997126 | 0.848187 |
| Heart | Left Ventricle | 260.413 | 37.24 | 6.99283029 | 0.844653 |
| AML | Primary | 5.943 | 0.881 | 6.745743473 | 0.82903 |
| Blood | PBMC | 66.387 | 9.855 | 6.736377473 | 0.828426 |
| Blood | CD14+ | 289.157 | 43.578 | 6.635389417 | 0.821866 |
| Breast | Tumor_Frozen | 256.522 | 39.023 | 6.573610435 | 0.817804 |
| Adrenal Gland | Primary | 53.29 | 8.421 | 6.328227051 | 0.801282 |
| Breast | Tumor_Frozen | 484.817 | 78.142 | 6.204307543 | 0.792693 |
| Breast | Tumor_Frozen | 308.285 | 50.926 | 6.053587558 | 0.782013 |
| Heart | Right Atrium | 256.582 | 43.002 | 5.966745733 | 0.775738 |
| Blood | CD4+ | 526.263 | 89.042 | 5.910278296 | 0.771608 |
| Blood | CD20+ | 240.5 | 41.031 | 5.861421852 | 0.768003 |
| Pancreas | Primary | 56.661 | 9.844 | 5.755891914 | 0.760113 |
| Prostate | LNCap | 141.113 | 25.097 | 5.622703909 | 0.749945 |
| Adipose | Primary | 55.047 | 9.831 | 5.599328654 | 0.748136 |
| AML | Primary | 217.682 | 39.355 | 5.531241265 | 0.742823 |
| Breast | Tumor_Frozen | 159.878 | 29.302 | 5.456214593 | 0.736891 |
| AML | Primary | 13.51 | 2.492 | 5.421348315 | 0.734107 |
| AML | Primary | 221.635 | 41.032 | 5.40151589 | 0.732516 |
| Blood | CD4+ | 355.44 | 67.525 | 5.263828212 | 0.721302 |
| Gastric | Primary | 91.879 | 17.526 | 5.242439804 | 0.719533 |
| Kidney | ADPKD | 224.768 | 43.161 | 5.207664327 | 0.716643 |
| Bone | MG63 | 184.328 | 35.725 | 5.159636109 | 0.712619 |

FIG. 3B

| Source | Cell Type | RARA:DIFF | Malat1:DIFF | RARA/MALAT1 | log 10 |
|---|---|---|---|---|---|
| Breast | Tumor_Frozen | 350.539 | 68.957 | 5.083443305 | 0.706158 |
| Psoas Muscle | Primary | 381.171 | 75.655 | 5.03827903 | 0.702282 |
| Breast | T47D | 685.887 | 137.14 | 5.00136357 | 0.699088 |
| AML | Patient_Normal | 5.441 | 1.09 | 4.991743119 | 0.698252 |
| Breast | Tumor_Frozen | 275.793 | 55.37 | 4.98091024 | 0.697309 |
| Breast | Tumor_Frozen | 22.855 | 4.624 | 4.942690311 | 0.693963 |
| Breast | Tumor_Frozen | 65.123 | 13.21 | 4.929825889 | 0.692832 |
| AML | Patient_Normal | 132.685 | 27.178 | 4.882073736 | 0.688604 |
| Glioblastoma | U87 MG | 153.109 | 31.802 | 4.814445632 | 0.682546 |
| AML | Primary | 259.92 | 54.831 | 4.740384089 | 0.675814 |
| Breast | Tumor_Frozen | 321.914 | 68.202 | 4.720008211 | 0.673943 |
| Blood | CD8 | 160.677 | 34.145 | 4.705725582 | 0.672627 |
| Kidney | ADPKD | 305.61 | 65.212 | 4.68640741 | 0.67084 |
| Blood | CD8 | 140.292 | 30.512 | 4.597928684 | 0.662562 |
| Blood | CD56 | 181.357 | 39.709 | 4.567151024 | 0.659645 |
| Blood | CD4+ | 162.875 | 35.881 | 4.539310499 | 0.65699 |
| Psoas Muscle | Primary | 261.41 | 57.943 | 4.511502684 | 0.654321 |
| Colon | Primary | 223.387 | 50.268 | 4.443920586 | 0.647766 |
| Small Intestine | Primary | 116.489 | 26.276 | 4.433285127 | 0.646726 |
| Breast | Metastatic Frozen | 56.085 | 12.868 | 4.358486167 | 0.639336 |
| Breast | Tumor_Frozen | 69.718 | 16.029 | 4.349491547 | 0.638438 |
| Bone | MG63 | 138.532 | 32.432 | 4.271460286 | 0.630576 |
| AML | Primary | 196.32 | 46.048 | 4.263377345 | 0.629754 |
| Motor neuron | 1-51N | 56.087 | 13.184 | 4.254171723 | 0.628815 |
| Breast | Metastatic Frozen | 157.07 | 37.059 | 4.238376643 | 0.6272 |
| Breast | Tumor_Frozen | 350.753 | 82.945 | 4.228741937 | 0.626211 |
| AML | Patient_Normal | 58.614 | 13.907 | 4.214712016 | 0.624768 |
| Adrenal Gland | Primary | 86.056 | 21.263 | 4.047218172 | 0.607157 |
| AML | Primary | 342.666 | 84.948 | 4.033832462 | 0.605718 |
| Breast | Normal_Frozen | 228.281 | 56.617 | 4.032022184 | 0.605523 |
| Spleen | Primary | 352.52 | 88.062 | 4.003088733 | 0.602395 |
| AML | Primary | 305.957 | 76.655 | 3.991350858 | 0.60112 |
| Colon | Primary | 165.265 | 41.415 | 3.990462393 | 0.601023 |
| AML | Patient_Normal | 173.067 | 44.163 | 3.918823449 | 0.593156 |
| Breast | Tumor_Frozen | 283.147 | 72.799 | 3.889435294 | 0.589887 |
| AML | Primary | 165.792 | 42.847 | 3.869395757 | 0.587643 |
| cRCC | A704 | 171.59 | 44.535 | 3.852924666 | 0.585791 |
| AML | Primary | 12.359 | 3.251 | 3.801599508 | 0.579966 |
| cRCC | A704 | 213.743 | 56.505 | 3.782727192 | 0.577805 |
| AML | Primary | 307.301 | 81.387 | 3.775799575 | 0.577009 |
| AML | Primary | 152.578 | 40.802 | 3.739473555 | 0.57281 |

FIG. 3C

| Source | Cell Type | RARA:DIFF | Malat1:DIFF | RARA/MALAT1 | log 10 |
|---|---|---|---|---|---|
| AML | Primary | 251.998 | 67.671 | 3.7238699 | 0.570994 |
| Breast | Tumor_Frozen | 57.239 | 15.391 | 3.718991618 | 0.570425 |
| Breast | Tumor_Frozen | 47.184 | 12.712 | 3.711768408 | 0.569581 |
| AML | Primary | 216.742 | 58.621 | 3.697343955 | 0.56789 |
| Breast | Normal_Frozen | 36.832 | 10.155 | 3.626981782 | 0.559545 |
| Breast | Tumor_Frozen | 47.903 | 13.239 | 3.618324647 | 0.558508 |
| AML | Primary | 340.218 | 95.024 | 3.580337599 | 0.553924 |
| Breast | Tumor_Frozen | 159.09 | 45.214 | 3.518600433 | 0.54637 |
| Breast | Normal_Frozen | 194.693 | 55.395 | 3.514631284 | 0.54588 |
| Gastric | Primary | 156.243 | 44.476 | 3.512973289 | 0.545675 |
| AML | Primary | 354.582 | 100.959 | 3.512138591 | 0.545572 |
| Breast | Normal_Frozen | 90.514 | 25.781 | 3.510880106 | 0.545416 |
| AML | Primary | 355.554 | 101.847 | 3.49106012 | 0.542957 |
| AML | Primary | 11.549 | 3.325 | 3.473383459 | 0.540753 |
| Bladder | Primary | 86.006 | 24.835 | 3.463096436 | 0.539465 |
| Blood | CD19 | 157.811 | 45.665 | 3.455841454 | 0.538554 |
| Non-Small Cell Lung Cancer | H358 | 205.661 | 59.647 | 3.447968884 | 0.537563 |
| AML | Primary | 94.545 | 27.577 | 3.428400479 | 0.535092 |
| Kidney | ADPKD | 115.224 | 33.736 | 3.415461228 | 0.533449 |
| Kidney | NHK | 325.362 | 96.465 | 3.372850257 | 0.527997 |
| AML | Primary | 183.529 | 54.601 | 3.361275435 | 0.526504 |
| Breast | Normal_Frozen | 13.184 | 3.957 | 3.331817033 | 0.522681 |
| Breast | Normal_Frozen | 110.841 | 33.67 | 3.291980992 | 0.517457 |
| Breast | Tumor_Frozen | 63.379 | 19.387 | 3.26914943 | 0.514435 |
| Breast | Normal_Frozen | 162.141 | 49.623 | 3.267456623 | 0.51421 |
| Esophagus | Primary | 162.698 | 50.172 | 3.242804752 | 0.510921 |
| Breast | Normal_Frozen | 43.273 | 13.348 | 3.2419089 | 0.510801 |
| Breast | Normal_Frozen | 113.972 | 35.323 | 3.22656626 | 0.508741 |
| AML | Primary | 500.464 | 155.58 | 3.21676308 | 0.507419 |
| Umbilical Vein | HUVEC | 213.408 | 66.408 | 3.213588724 | 0.50699 |
| Breast | Tumor_Frozen | 111.101 | 34.593 | 3.211661319 | 0.50673 |
| Breast | Tumor_Frozen | 128.592 | 40.085 | 3.207983036 | 0.506232 |
| AML | Patient_Normal | 62.864 | 19.618 | 3.204404119 | 0.505747 |
| AML | Primary | 207.42 | 64.742 | 3.203793519 | 0.505665 |
| Lung | Primary | 168.424 | 52.825 | 3.188338855 | 0.503564 |
| Multiple myeloma | MM1.S | 97.703 | 30.652 | 3.187491844 | 0.503449 |
| Heart | Left Ventricle | 201.853 | 63.4 | 3.183801262 | 0.502946 |
| Breast | Normal_Frozen | 143.997 | 45.24 | 3.18295756 | 0.502831 |
| AML | Primary | 58.312 | 18.455 | 3.159685722 | 0.499644 |

FIG. 3D

| Source | Cell Type | RARA:DIFF | Malat1:DIFF | RARA/MALAT1 | log 10 |
|---|---|---|---|---|---|
| Breast | Tumor_Frozen | 385.078 | 122.098 | 3.153843634 | 0.49884 |
| Breast | Normal_Frozen | 90.442 | 28.805 | 3.139802118 | 0.496902 |
| AML | SKM | 12.277 | 3.911 | 3.139094861 | 0.496804 |
| AML | Primary | 437.034 | 140.171 | 3.117863181 | 0.493857 |
| Blood | CD14+ | 154.874 | 49.977 | 3.098905497 | 0.491208 |
| Breast | Normal_Frozen | 86.478 | 28.629 | 3.020643404 | 0.480099 |
| AML | Primary | 517.274 | 172.321 | 3.001804771 | 0.477382 |
| Breast | MCF7 | 53.191 | 17.739 | 2.998534303 | 0.476909 |
| Breast | MCF7 | 52.767 | 17.739 | 2.974632166 | 0.473433 |
| AML | HEL | 126.284 | 42.902 | 2.943545755 | 0.468871 |
| Breast | HCC38 | 367.489 | 125.135 | 2.93674032 | 0.467866 |
| Colon Crypt | Primary Cancer | 171.463 | 58.595 | 2.92623944 | 0.46631 |
| Motor neuron | 1-38G | 60.413 | 20.79 | 2.905868206 | 0.463276 |
| Breast | Normal_Frozen | 74.451 | 25.852 | 2.879893238 | 0.459376 |
| Spleen | Primary | 221.175 | 77.972 | 2.836595188 | 0.452797 |
| Non-Small Cell Lung Cancer | H23 | 226.758 | 80.226 | 2.826490165 | 0.451247 |
| Blood | CD4+ | 337.879 | 119.713 | 2.822408594 | 0.45062 |
| Breast | Normal_Frozen | 167.76 | 59.561 | 2.816608183 | 0.449726 |
| Skeletal Muscle | Primary | 323.724 | 115.304 | 2.807569555 | 0.448331 |
| Breast | Tumor_Frozen | 196.023 | 70.32 | 2.787585324 | 0.445228 |
| Bone | MG63 | 99.811 | 35.939 | 2.777233646 | 0.443612 |
| Breast | Tumor_Frozen | 157.516 | 57.027 | 2.762130219 | 0.441244 |
| AML | Primary | 468.142 | 170.458 | 2.746377407 | 0.43876 |
| Breast | Tumor_Frozen | 17.784 | 6.499 | 2.736420988 | 0.437183 |
| AML | Primary | 357.739 | 131.257 | 2.725485117 | 0.435444 |
| AML | Patient_Normal | 53.016 | 19.715 | 2.689119959 | 0.42961 |
| Multiple myeloma | MM1.S | 183.592 | 68.524 | 2.679236472 | 0.428011 |
| Breast | HCC1954 | 208.277 | 77.865 | 2.674847492 | 0.427299 |
| AML | Primary | 164.283 | 61.891 | 2.6543924 | 0.423965 |
| Blood | JVM-2 | 52.589 | 19.995 | 2.630107527 | 0.419974 |
| Pancreas | Primary | 48.176 | 18.367 | 2.6229651 | 0.418793 |
| Colon Crypt | Primary Cancer | 139.254 | 53.126 | 2.621202424 | 0.418501 |
| Leg Muscle | Primary | 287.067 | 109.824 | 2.613882212 | 0.417286 |
| Breast | Tumor_Frozen | 220.888 | 84.604 | 2.610845823 | 0.416781 |
| AML | Primary | 418.344 | 162.524 | 2.574044449 | 0.410616 |
| AML | MV4-11 | 214.607 | 83.873 | 2.55871377 | 0.408022 |
| Breast | Tumor_Frozen | 133.258 | 52.117 | 2.556900819 | 0.407714 |
| Adipose | Primary | 166.546 | 65.179 | 2.5552095 | 0.407427 |

FIG. 3E

| Source | Cell Type | RARA:DIFF | Malat1:DIFF | RARA/MALAT1 | log 10 |
|---|---|---|---|---|---|
| Multiple myeloma | MM1.S | 218.734 | 85.616 | 2.554826201 | 0.407361 |
| Blood | CD4+ CD25- CD45+ RA+ | 171.378 | 67.654 | 2.533153989 | 0.403662 |
| Blood | CD3+ | 305.314 | 121.703 | 2.508680969 | 0.399445 |
| AML | Primary | 179.266 | 71.682 | 2.500850981 | 0.398088 |
| AML | Primary | 106.375 | 42.689 | 2.49185973 | 0.396524 |
| Breast | ZR-75-1 | 111.06 | 44.659 | 2.486844757 | 0.395649 |
| AML | Primary | 261.074 | 106.429 | 2.453034417 | 0.389704 |
| Breast | HCC70 | 164.534 | 67.251 | 2.44656585 | 0.388557 |
| AML | YNH-1 | 262.591 | 107.882 | 2.434057581 | 0.386331 |
| Gastric | Primary | 65.345 | 27.107 | 2.41063194 | 0.382131 |
| AML | Primary | 169.499 | 70.403 | 2.407553655 | 0.381576 |
| Breast | Metastatic Frozen | 136.647 | 57.073 | 2.39424947 | 0.379169 |
| AML | THP-1 | 142.733 | 59.883 | 2.383531219 | 0.377221 |
| Breast | Tumor_Frozen | 64.168 | 27.082 | 2.369396647 | 0.374638 |
| AML | Primary | 187.293 | 79.958 | 2.342392256 | 0.36966 |
| Breast | HCC1954 | 11.187 | 4.813 | 2.32432994 | 0.366298 |
| AML | Sig-M5 | 210.026 | 90.772 | 2.313775173 | 0.364321 |
| AML | KG-1 | 217.787 | 94.73 | 2.299028819 | 0.361544 |
| AML | Primary | 84.822 | 36.942 | 2.296085756 | 0.360988 |
| AML | Primary | 367.95 | 161.515 | 2.278116584 | 0.357576 |
| AML | Primary | 59.231 | 26.007 | 2.277502211 | 0.357459 |
| Blood | CD4+ | 145.681 | 64.74 | 2.250247142 | 0.35223 |
| Blood | CD4+ | 200.308 | 91.793 | 2.182170754 | 0.338889 |
| Multiple myeloma | MM1.S | 212.216 | 97.802 | 2.169853377 | 0.33643 |
| Small Intestine | Primary | 167.213 | 77.084 | 2.169230969 | 0.336306 |
| AML | Primary | 243.605 | 112.592 | 2.163608427 | 0.335179 |
| Breast | Tumor_Frozen | 23.037 | 10.762 | 2.140587251 | 0.330533 |
| Colon | V9M | 267.689 | 125.318 | 2.136077818 | 0.329617 |
| Blood | CD8+ | 132.788 | 62.307 | 2.131189112 | 0.328622 |
| Breast | Tumor_Frozen | 157.375 | 74.313 | 2.117731756 | 0.325871 |
| Pancreas | PANC-1 | 124.367 | 59.557 | 2.088201219 | 0.319772 |
| Breast | Tumor_Frozen | 158.713 | 76.313 | 2.079763605 | 0.318014 |
| AML | THP-1 | 18.516 | 8.918 | 2.07625028 | 0.31728 |
| AML | Primary | 134.237 | 64.789 | 2.071910355 | 0.316371 |
| Melanoma | SK-MEL-1 | 143.222 | 69.479 | 2.061371062 | 0.314156 |
| AML | Primary | 210.385 | 102.413 | 2.054280218 | 0.31266 |
| Lymphoblastoid | GM18951 | 193.268 | 94.171 | 2.052309097 | 0.312243 |
| Breast | Normal_Frozen | 71.71 | 35.127 | 2.041449597 | 0.309939 |

FIG. 3F

| Source | Cell Type | RARA:DIFF | Malat1:DIFF | RARA/MALAT1 | log 10 |
|---|---|---|---|---|---|
| AML | Primary | 330.63 | 162.514 | 2.034470876 | 0.308451 |
| Breast | 184-A1 | 161.287 | 79.298 | 2.033935282 | 0.308337 |
| Breast | Tumor_Frozen | 125.797 | 61.987 | 2.029409392 | 0.30737 |
| Kidney | NHK | 184.678 | 91.398 | 2.02059126 | 0.305478 |
| Esophagus | Primary | 108.821 | 53.88 | 2.019691908 | 0.305285 |
| Large Intestines | Primary | 156.768 | 78.314 | 2.001787675 | 0.301418 |
| Glioblastoma | U-251 | 99.009 | 49.723 | 1.991211311 | 0.299117 |
| Breast | Tumor_Frozen | 49.816 | 25.059 | 1.987948442 | 0.298405 |
| AML | Primary | 57.419 | 29.06 | 1.975877495 | 0.29576 |
| AML | Primary | 93.9 | 47.837 | 1.962915735 | 0.292902 |
| Duodenum Smooth Muscle | Primary | 78.67 | 40.086 | 1.962530559 | 0.292816 |
| cRCC | RCC4 | 126.134 | 64.512 | 1.955202133 | 0.291192 |
| Breast | Tumor_Frozen | 46.493 | 23.797 | 1.953733664 | 0.290865 |
| Blood | CD133+ | 249.498 | 127.896 | 1.95078814 | 0.29021 |
| AML | Primary | 92.832 | 48.28 | 1.922783761 | 0.28393 |
| Colorectal | 201 | 150.449 | 78.507 | 1.916376884 | 0.282481 |
| AML | Primary | 176.178 | 92.325 | 1.908237206 | 0.280632 |
| Colon Crypt | Primary Cancer | 121.561 | 63.753 | 1.906749486 | 0.280294 |
| AML | Primary | 182.194 | 95.804 | 1.901736879 | 0.27915 |
| AML | Primary | 57.352 | 30.158 | 1.901717621 | 0.279146 |
| AML | Primary | 50.731 | 26.742 | 1.897053324 | 0.27808 |
| Bone | Osteoblasts | 95.817 | 50.806 | 1.885938669 | 0.275528 |
| AML | Primary | 105.278 | 55.885 | 1.883832871 | 0.275042 |
| Ewings Sarcoma | SK-ES1 | 98.578 | 52.624 | 1.873251748 | 0.272596 |
| AML | Primary | 306.286 | 164.192 | 1.865413662 | 0.270775 |
| Lymphoblastoid | GM10847 | 209.689 | 112.709 | 1.860445927 | 0.269617 |
| Lymphoblastoid | SNYDER | 108.086 | 58.953 | 1.833426628 | 0.263264 |
| Blood | CD8+ | 91.086 | 49.814 | 1.828522102 | 0.2621 |
| AML | Primary | 203.442 | 111.333 | 1.827328824 | 0.261817 |
| Ewings Sarcoma | TC71 | 105.905 | 57.957 | 1.827303001 | 0.261811 |
| Lymphoblastoid | SNYDER | 95.56 | 52.304 | 1.827011318 | 0.261741 |
| Breast | Tumor_Frozen | 147.162 | 80.689 | 1.823817373 | 0.260981 |
| Lymphoblastoid | GM19099 | 185.561 | 101.799 | 1.822817513 | 0.260743 |
| AML | Primary | 26.052 | 14.53 | 1.792980041 | 0.253575 |
| Breast | Tumor_Frozen | 216.866 | 121.124 | 1.790446154 | 0.252961 |
| Breast | hTERT_HME1 | 108.937 | 60.894 | 1.788961146 | 0.252601 |
| AML | Primary | 149.672 | 83.853 | 1.784933157 | 0.251622 |
| AML | Primary | 34.955 | 19.619 | 1.781691218 | 0.250832 |
| cRCC | 786O | 80.771 | 45.334 | 1.781687034 | 0.250831 |
| AML | Primary | 175.418 | 98.693 | 1.777410759 | 0.249788 |

FIG. 3G

| Source | Cell Type | RARA:DIFF | Malat1:DIFF | RARA/MALAT1 | log 10 |
|---|---|---|---|---|---|
| AML | Primary | 129.536 | 72.989 | 1.774733179 | 0.249133 |
| AML | Primary | 91.336 | 51.831 | 1.762188652 | 0.246052 |
| AML | Primary | 30.291 | 17.258 | 1.755186001 | 0.244323 |
| AML | Primary | 138.232 | 78.978 | 1.750259566 | 0.243102 |
| Lymphoblastoid | GM19099 | 200.13 | 114.9 | 1.741775457 | 0.240992 |
| Basal Epithelial Cells | A549 | 198.015 | 113.971 | 1.737415658 | 0.239904 |
| Blood | CD4+ | 170.244 | 98.007 | 1.737059598 | 0.239815 |
| Breast | Tumor_Frozen | 166.114 | 95.9 | 1.732158498 | 0.238588 |
| AML | Primary | 173.627 | 101.179 | 1.716037913 | 0.234527 |
| AML | Primary | 27.31 | 15.923 | 1.715129059 | 0.234297 |
| AML | Primary | 162.307 | 95.072 | 1.707200858 | 0.232285 |
| cRCC | 786O | 67.005 | 39.449 | 1.698522143 | 0.230071 |
| AML | Primary | 150.649 | 88.835 | 1.695829347 | 0.229382 |
| Lymphoblastoid | GM19238 | 222.739 | 131.567 | 1.692970122 | 0.228649 |
| Melanoma | SK-MEL-28 | 43.969 | 26.063 | 1.687027587 | 0.227122 |
| Ewings Sarcoma | TC71 | 98.156 | 58.777 | 1.669972949 | 0.222709 |
| AML | Primary | 37.962 | 22.747 | 1.668879413 | 0.222425 |
| AML | Primary | 21.974 | 13.231 | 1.660796614 | 0.220316 |
| AML | Primary | 36.456 | 21.963 | 1.65988253 | 0.220077 |
| Breast | Normal_Frozen | 75.68 | 45.646 | 1.657976603 | 0.219578 |
| Breast | Tumor_Frozen | 68.938 | 41.727 | 1.652119731 | 0.218042 |
| AML | ME1 | 111.457 | 67.836 | 1.643036146 | 0.215647 |
| Lymphoblastoid | GM19238 | 202.272 | 123.184 | 1.642031433 | 0.215381 |
| Ewings Sarcoma | TC71 | 83.781 | 51.239 | 1.635102168 | 0.213545 |
| Melanoma | Hs 605.Sk | 108.467 | 66.818 | 1.623320063 | 0.210404 |
| AML | THP-1 | 128.085 | 78.96 | 1.622150456 | 0.210091 |
| Breast | hTERT_HME1 | 105.441 | 65.132 | 1.618881656 | 0.209215 |
| Breast | Hs739 | 97.86 | 60.784 | 1.609963148 | 0.206816 |
| Lymphoblastoid | GM19193 | 182.952 | 114.194 | 1.602115698 | 0.204694 |
| AML | Primary | 216.401 | 135.579 | 1.596124769 | 0.203067 |
| Blood | CD8+ | 234.955 | 147.836 | 1.589294894 | 0.201204 |
| Colon | V503 | 135.932 | 86.011 | 1.580402507 | 0.198768 |
| Lymphoblastoid | SNYDER | 118.355 | 74.901 | 1.580152468 | 0.198699 |
| AML | Primary | 134.96 | 85.974 | 1.569776909 | 0.195838 |
| Lymphoblastoid | GM2630 | 211.457 | 134.928 | 1.56718398 | 0.19512 |
| AML | Primary | 120.794 | 77.182 | 1.565054028 | 0.194529 |
| Lymphoblastoid | GM10847 | 191.341 | 122.355 | 1.563818397 | 0.194186 |
| Blood | CD19+ | 234.268 | 150.836 | 1.553130552 | 0.191208 |
| AML | Primary | 97.456 | 62.816 | 1.551451859 | 0.190738 |
| Lymphoblastoid | GM2630 | 200.779 | 129.451 | 1.551003855 | 0.190613 |

FIG. 3H

| Source | Cell Type | RARA:DIFF | Malat1:DIFF | RARA/MALAT1 | log 10 |
|---|---|---|---|---|---|
| AML | EOL-1 | 200.982 | 130.342 | 1.541958847 | 0.188073 |
| Breast | HCC-1937 | 241.354 | 156.567 | 1.541538127 | 0.187954 |
| AML | Primary | 164.513 | 106.82 | 1.540095488 | 0.187548 |
| Blood | CD4+ | 63.535 | 41.403 | 1.534550636 | 0.185981 |
| AML | MEGAL | 64.676 | 42.233 | 1.531409088 | 0.185091 |
| AML | Primary | 57.385 | 37.539 | 1.528676843 | 0.184316 |
| Blood | CD8+ | 99.089 | 65.306 | 1.517303157 | 0.181072 |
| Lymphoblastoid | GM18526 | 205.342 | 135.403 | 1.516524745 | 0.18085 |
| Lymphoblastoid | GM19193 | 172.288 | 114.808 | 1.500661975 | 0.176283 |
| AML | Primary | 39.024 | 26.04 | 1.498617512 | 0.175691 |
| Peripheral blood cells | EoL-1 | 207.578 | 139.749 | 1.485363044 | 0.171833 |
| AML | THP-1 | 45.114 | 30.437 | 1.482209153 | 0.170909 |
| Lymphoblastoid | GM2588 | 177.515 | 120.423 | 1.47409548 | 0.168526 |
| AML | Primary | 106.194 | 72.136 | 1.472135965 | 0.167948 |
| AML | OCI-M1 | 9.818 | 6.672 | 1.471522782 | 0.167767 |
| AML | Primary | 92.115 | 62.64 | 1.470545977 | 0.167479 |
| AML | Primary | 83.545 | 56.941 | 1.467220456 | 0.166495 |
| Lymphoblastoid | GM2588 | 159.499 | 108.783 | 1.466212552 | 0.166197 |
| AML | THP-1 | 120.056 | 82.272 | 1.459257098 | 0.164132 |
| AML | Primary | 70.909 | 48.924 | 1.449370452 | 0.161179 |
| Lymphoblastoid | Gm12891 | 218.217 | 150.573 | 1.449243888 | 0.161141 |
| AML | Primary | 46.448 | 32.169 | 1.443874538 | 0.159529 |
| cRCC | RCC4 | 84.187 | 58.357 | 1.442620423 | 0.159152 |
| AML | Primary | 106.22 | 73.64 | 1.442422596 | 0.159093 |
| Lymphoblastoid | GM19239 | 193.212 | 134.737 | 1.433993632 | 0.156547 |
| Lymphoblastoid | GM18505 | 193.464 | 135.384 | 1.42900195 | 0.155033 |
| AML | Primary | 151.591 | 106.234 | 1.426953706 | 0.15441 |
| Lymphoblastoid | GM18526 | 159.498 | 112.248 | 1.420942912 | 0.152577 |
| Skeletal Muscle Myotubes | HSSMtube | 136.677 | 96.452 | 1.417046821 | 0.151384 |
| AML | Primary | 54.631 | 38.592 | 1.41560427 | 0.150942 |
| AML | Primary | 44.251 | 31.278 | 1.414764371 | 0.150684 |
| Lung | NHLF | 145.626 | 103.074 | 1.412829618 | 0.15009 |
| Lymphoblastoid | Gm12891 | 214.427 | 152.007 | 1.410638984 | 0.149416 |
| AML | Primary | 92.08 | 65.753 | 1.400392378 | 0.14625 |
| AML | Primary | 133.2 | 95.538 | 1.394209634 | 0.144328 |
| Lymphoblastoid | GM12890 | 187.514 | 134.537 | 1.393772717 | 0.144192 |
| Breast | MCF10A | 74.576 | 53.56 | 1.392382375 | 0.143759 |
| AML | THP-1 | 42.285 | 30.431 | 1.389536985 | 0.14287 |
| Breast | Tumor_Frozen | 35.707 | 25.702 | 1.389269318 | 0.142786 |

FIG. 3I

| Source | Cell Type | RARA:DIFF | Malat1:DIFF | RARA/MALAT1 | log 10 |
|---|---|---|---|---|---|
| AML | THP-1 | 115.205 | 82.961 | 1.388664553 | 0.142597 |
| Dermis | NHDF-Ad | 67.944 | 49.312 | 1.377839066 | 0.139198 |
| AML | Primary | 101.467 | 73.653 | 1.37763567 | 0.139134 |
| AML | Primary | 226.147 | 164.407 | 1.375531455 | 0.138471 |
| AML | SKNO-1 | 104.948 | 76.531 | 1.371313585 | 0.137137 |
| Lymphoblastoid | GM12890 | 211.929 | 154.984 | 1.367425025 | 0.135904 |
| Multiple myeloma | MM1.S | 65.27 | 47.879 | 1.363228138 | 0.134569 |
| AML | Primary | 101.507 | 74.978 | 1.353823788 | 0.131562 |
| Blood | RPMI-8402 | 49.205 | 36.722 | 1.339932466 | 0.127083 |
| Lymphoblastoid | GM19240 | 181.108 | 135.285 | 1.338714566 | 0.126688 |
| Lymphoblastoid | Gm12891 | 208.716 | 156.212 | 1.336107341 | 0.125841 |
| Lymphoblastoid | GM18505 | 185.867 | 139.537 | 1.332026631 | 0.124513 |
| Lymphoblastoid | GM12878 | 141.435 | 106.33 | 1.330151415 | 0.123901 |
| Colorectal | HCT-116 | 89.927 | 67.681 | 1.328688997 | 0.123423 |
| Breast | MDA-231 | 112.772 | 84.974 | 1.327135359 | 0.122915 |
| Breast | Tumor_Frozen | 53.558 | 40.366 | 1.326809691 | 0.122809 |
| Lymphoblastoid | GM2610 | 139.482 | 105.511 | 1.32196643 | 0.12122 |
| Lymphoblastoid | GM19239 | 232.984 | 176.797 | 1.317805166 | 0.119851 |
| AML | THP-1 | 74.235 | 56.375 | 1.316807095 | 0.119522 |
| AML | Primary | 130.503 | 99.498 | 1.311614304 | 0.117806 |
| Breast | Tumor_Frozen | 21.493 | 16.393 | 1.3111084 | 0.117639 |
| AML | Primary | 69.006 | 52.78 | 1.307427056 | 0.116417 |
| Thymus | Primary | 60.641 | 46.425 | 1.306214324 | 0.116014 |
| Breast | Tumor_Frozen | 27.883 | 21.388 | 1.303674958 | 0.115169 |
| AML | Primary | 35.662 | 27.46 | 1.298689002 | 0.113505 |
| AML | THP-1 | 49.041 | 37.893 | 1.294196817 | 0.112 |
| AML | Primary | 28.089 | 21.897 | 1.282778463 | 0.108152 |
| Lymphoblastoid | GM12878 | 209.656 | 165.331 | 1.268098542 | 0.103153 |
| AML | THP-1 | 124.276 | 98.777 | 1.25814714 | 0.099731 |
| AML | Primary | 94.627 | 75.609 | 1.251530902 | 0.097442 |
| AML | MOLM-13 | 91.202 | 73.027 | 1.248880551 | 0.096521 |
| AML | Primary | 109.815 | 88.012 | 1.247727583 | 0.09612 |
| Lymphoblastoid | SNYDER | 205.506 | 165.775 | 1.239668225 | 0.093305 |
| Lymphoblastoid | GM12892 | 206.614 | 166.749 | 1.239071898 | 0.093097 |
| AML | THP-1 | 78.678 | 63.729 | 1.234571388 | 0.091516 |
| Lymphoblastoid | GM2610 | 117.23 | 95.065 | 1.233156262 | 0.091018 |
| AML | THP-1 | 43.923 | 35.698 | 1.230405065 | 0.090048 |
| AML | THP-1 | 107.533 | 89.397 | 1.202870342 | 0.080219 |
| AML | THP-1 | 114.401 | 95.228 | 1.201337842 | 0.079665 |
| AML | THP-1 | 114.642 | 96.219 | 1.19146946 | 0.076083 |

FIG. 3J

| Source | Cell Type | RARA:DIFF | Malat1:DIFF | RARA/MALAT1 | log 10 |
|---|---|---|---|---|---|
| AML | Primary | 80.605 | 67.802 | 1.188829238 | 0.075119 |
| Lymphoblastoid | GM18486 | 146.544 | 123.387 | 1.187677794 | 0.074699 |
| AML | THP-1 | 56.586 | 47.758 | 1.184848612 | 0.073663 |
| Basal Epithelial Cells | A549 | 140.79 | 119.61 | 1.177075495 | 0.070804 |
| AML | Primary | 103.005 | 87.61 | 1.17572195 | 0.070305 |
| AML | Primary | 113.985 | 97.093 | 1.173977527 | 0.06966 |
| AML | Primary | 106.01 | 90.565 | 1.170540496 | 0.068386 |
| Blood | SU-DHL-5 | 27.521 | 23.834 | 1.154694974 | 0.062467 |
| AML | THP-1 | 90.635 | 79.009 | 1.147147793 | 0.059619 |
| Lymphoblastoid | GM19239 | 188.653 | 164.585 | 1.146234469 | 0.059273 |
| AML | Primary | 120.359 | 105.051 | 1.145719698 | 0.059078 |
| Ectoderm | HMEC | 55.874 | 48.858 | 1.14359982 | 0.058274 |
| Lymphoblastoid | GM18951 | 127.743 | 111.862 | 1.14196957 | 0.057655 |
| Lymphoblastoid | GM2255 | 155.322 | 137.087 | 1.133017719 | 0.054237 |
| Cord Blood | CD34+ | 62.021 | 54.755 | 1.13270021 | 0.054115 |
| Lymphoblastoid | GM19238 | 160.542 | 142.602 | 1.125804687 | 0.051463 |
| Lymphoblastoid | GM18486 | 153.358 | 136.324 | 1.124952319 | 0.051134 |
| AML | HL60 | 234.089 | 209.025 | 1.119909102 | 0.049183 |
| AML | Primary | 193.195 | 173.1 | 1.116088966 | 0.047699 |
| AML | Primary | 34.156 | 30.639 | 1.114788342 | 0.047192 |
| Breast | MDA-MB175 | 84.887 | 76.398 | 1.111115474 | 0.045759 |
| Lymphoblastoid | GM12892 | 188.519 | 171.72 | 1.097827859 | 0.040534 |
| Breast | BT474 | 67.929 | 62.685 | 1.083656377 | 0.034892 |
| Non-Small CellLung Cancer | H820 | 58.418 | 53.966 | 1.082496387 | 0.034426 |
| AML | THP-1 | 63.789 | 58.947 | 1.082141585 | 0.034284 |
| Blood | CD34+ | 45.477 | 42.061 | 1.081215378 | 0.033912 |
| AML | Primary | 58.884 | 54.52 | 1.080044021 | 0.033441 |
| Colon | V400 | 74.984 | 69.824 | 1.073900092 | 0.030964 |
| Lymphoblastoid | GM19240 | 162.639 | 152.45 | 1.066835028 | 0.028097 |
| Ewings Sarcoma | SK-ES1 | 62.652 | 58.859 | 1.064442141 | 0.027122 |
| AML | OCI-AML3 | 99.455 | 93.591 | 1.062655597 | 0.026393 |
| Lymphoblastoid | GM2255 | 151.272 | 142.524 | 1.061379136 | 0.025871 |
| AML | FKH-1 | 61.454 | 57.996 | 1.059624802 | 0.025152 |
| Lymphoblastoid | GM12878 | 123.648 | 117.291 | 1.054198532 | 0.022922 |
| AML | Primary | 143.004 | 136.82 | 1.04519807 | 0.019199 |
| AML | THP-1 | 60.877 | 58.281 | 1.044542818 | 0.018926 |
| Lymphoblastoid | GM12878 | 126.32 | 121.578 | 1.039003767 | 0.016617 |
| Colorectal | SW-1463 | 93.962 | 90.596 | 1.037153958 | 0.015843 |
| AML | Primary | 11.718 | 11.477 | 1.020998519 | 0.009025 |

FIG. 3K

| Source | Cell Type | RARA:DIFF | Malat1:DIFF | RARA/MALAT1 | log 10 |
|---|---|---|---|---|---|
| Ewings Sarcoma | A673 | 50.476 | 49.44 | 1.020954693 | 0.009006 |
| Lymphoblastoid | GM12878 | 196.314 | 194.541 | 1.00911376 | 0.00394 |
| AML | PL21 | 93.871 | 93.058 | 1.008736487 | 0.003778 |
| AML | Primary | 128.6 | 127.61 | 1.007758013 | 0.003356 |
| Lymphoblastoid | GM12878 | 125.245 | 124.338 | 1.007294632 | 0.003157 |
| Breast | Tumor_Frozen | 24.31 | 24.152 | 1.006541901 | 0.002832 |
| AML | Primary | 29.507 | 29.344 | 1.005554798 | 0.002406 |
| Lymphoblastoid | GM12892 | 193.205 | 192.162 | 1.005427712 | 0.002351 |
| AML | Primary | 118.931 | 118.447 | 1.004086216 | 0.001771 |
| Breast | MDA-MB361 | 156.935 | 156.798 | 1.000873736 | 0.000379 |
| Lymphoblastoid | GM12878 | 163.701 | 164.597 | 0.994556401 | -0.00237 |
| Lymphoblastoid | SNYDER | 151.813 | 153.254 | 0.990597309 | -0.0041 |
| Blood | MPP | 24.296 | 24.554 | 0.989492547 | -0.00459 |
| Breast | HCC1143 | 48.543 | 49.463 | 0.981400239 | -0.00815 |
| AML | Primary | 41.214 | 42.107 | 0.978792125 | -0.00931 |
| AML | F-36P | 81.315 | 83.38 | 0.975233869 | -0.01089 |
| AML | Primary | 114.504 | 119.271 | 0.960032196 | -0.01771 |
| Lymphoblastoid | GM12878 | 114.141 | 120.095 | 0.950422582 | -0.02208 |
| Cord Blood | CD34+ | 119.063 | 126.729 | 0.939508715 | -0.0271 |
| Blood | DG-75 | 12.799 | 13.722 | 0.932735753 | -0.03024 |
| cRCC | UMRC2 | 70.272 | 75.549 | 0.930151293 | -0.03145 |
| Induced Pluripotent Stem Cells | 1-38G | 24.245 | 26.207 | 0.925134506 | -0.0338 |
| Lymphoblastoid | GM19240 | 149.271 | 162.443 | 0.918913096 | -0.03673 |
| AML | Primary | 106.49 | 116.98 | 0.910326552 | -0.0408 |
| cRCC | Caki2 | 31.867 | 35.055 | 0.909057196 | -0.04141 |
| Ewings Sarcoma | A673 | 51.911 | 57.203 | 0.90748737 | -0.04216 |
| Breast | Tumor_Frozen | 45.581 | 50.626 | 0.900347647 | -0.04559 |
| Brain | Astrocytes | 60.48 | 67.341 | 0.898115561 | -0.04667 |
| AML | Primary | 150.929 | 170.484 | 0.885297154 | -0.05291 |
| Skeletal Muscle | Myoblasts | 81.494 | 92.649 | 0.879599348 | -0.05572 |
| Ewings Sarcoma | A673 | 46.315 | 53.506 | 0.865603858 | -0.06268 |
| AML | OCI-AML2 | 53.052 | 61.588 | 0.861401572 | -0.06479 |
| Breast | Tumor_Frozen | 40.396 | 46.928 | 0.860808046 | -0.06509 |
| AML | Primary | 33.8 | 39.61 | 0.853319869 | -0.06889 |
| Lung | H2171 | 48.895 | 57.53 | 0.849904398 | -0.07063 |
| Blood | KARPAS-422 | 12.436 | 14.676 | 0.847369856 | -0.07193 |
| Cord Blood | CD34+ | 40.3 | 48.385 | 0.832902759 | -0.07941 |
| Breast | MDA-MB453 | 25.532 | 31.169 | 0.81914723 | -0.08664 |
| AML | HL60 | 47.668 | 59.728 | 0.79808465 | -0.09795 |

FIG. 3L

| Source | Cell Type | RARA:DIFF | Malat1:DIFF | RARA/MALAT1 | log 10 |
|---|---|---|---|---|---|
| AML | MKPL-1 | 14.397 | 18.359 | 0.784193039 | -0.10558 |
| AML | Primary | 28.294 | 36.538 | 0.774371887 | -0.11105 |
| AML | Primary | 18.277 | 23.63 | 0.773465933 | -0.11156 |
| Cervical Cancer | HeLA-S3 | 114.391 | 148.197 | 0.771884721 | -0.11245 |
| AML | OCI-AML3 | 94.275 | 122.821 | 0.767580463 | -0.11488 |
| AML | KG-1a | 93.708 | 124.774 | 0.751021848 | -0.12435 |
| AML | HL60 | 30.485 | 42.342 | 0.719970715 | -0.14269 |
| AML | Nomo-1 | 39.812 | 57.231 | 0.69563698 | -0.15762 |
| cRCC | Caki2 | 27.178 | 39.141 | 0.694361411 | -0.15841 |
| Ewings Sarcoma | SK-ES1 | 21.851 | 31.472 | 0.694299695 | -0.15845 |
| AML | Primary | 15.938 | 22.999 | 0.692986652 | -0.15928 |
| AML | Primary | 40.007 | 57.893 | 0.691050732 | -0.16049 |
| Breast | Normal_Frozen | 7.76 | 11.606 | 0.668619679 | -0.17482 |
| Breast | MCF7 | 61.334 | 91.792 | 0.668184591 | -0.1751 |
| Blood | HSC | 9.108 | 14.103 | 0.645820038 | -0.18989 |
| AML | GF-D8 | 137.604 | 219.024 | 0.628259917 | -0.20186 |
| Breast | MDA-MB468 | 46.579 | 76.637 | 0.607787361 | -0.21625 |
| AML | Primary | 7.706 | 12.881 | 0.598245478 | -0.22312 |
| AML | CMK | 76.354 | 128.344 | 0.594916786 | -0.22554 |
| AML | Primary | 71.392 | 122.074 | 0.584825598 | -0.23297 |
| Breast | MCF7 | 150.16 | 257.798 | 0.582471547 | -0.23473 |
| Breast | MCF10A | 41.647 | 71.603 | 0.581637641 | -0.23535 |
| AML | NB-4 | 54.351 | 94.727 | 0.573764608 | -0.24127 |
| Kidney | HEK293T | 35.566 | 62.985 | 0.564674129 | -0.2482 |
| Blood | CMP | 10.877 | 20.114 | 0.540767625 | -0.26699 |
| Non-Small CellLung Cancer | H1650 | 49.689 | 92.244 | 0.538669182 | -0.26868 |
| Breast | MDA-MB435 | 6.58 | 12.627 | 0.521105567 | -0.28307 |
| AML | AP-1060 | 85.906 | 164.943 | 0.520822345 | -0.28331 |
| Blood | MEP | 23.885 | 46.553 | 0.513071123 | -0.28982 |
| Breast | HCC1569 | 99.475 | 213.219 | 0.466539098 | -0.33111 |
| CML | K562 | 50.797 | 110.837 | 0.458303635 | -0.33885 |
| Breast | Tumor_Frozen | 3.606 | 7.946 | 0.453813239 | -0.34312 |
| Blood | U-266 | 44.43 | 117.889 | 0.376879946 | -0.4238 |
| AML | HL60 | 9.63 | 25.657 | 0.375336166 | -0.42558 |
| CML | K562 | 50.4 | 140.969 | 0.357525413 | -0.44669 |
| Peripheral blood cells | Myeloblast | 84.072 | 250.244 | 0.335960103 | -0.47371 |
| Liver | HepG2 | 38.671 | 115.216 | 0.335639147 | -0.47413 |
| Thymus | Primary | 51.823 | 155.982 | 0.332237053 | -0.47855 |
| Blood | DND-41 | 21.598 | 66.322 | 0.325653629 | -0.48724 |

FIG. 3M

| Source | Cell Type | RARA:DIFF | Malat1:DIFF | RARA/MALAT1 | log 10 |
|---|---|---|---|---|---|
| AML | MOLM-16 | 31.431 | 102.225 | 0.307468819 | -0.5122 |
| Breast | 184-B5 | 24.943 | 85.98 | 0.290102349 | -0.53745 |
| Embryonic stem cells | H1 | 3.233 | 13.125 | 0.24632381 | -0.60849 |
| Breast | MCF10A | 9.915 | 42.509 | 0.233244725 | -0.63219 |
| AML | Kasumi-1 | 48.524 | 209.535 | 0.23157945 | -0.6353 |
| Motor neuron | BJ | 5.058 | 29.726 | 0.170154074 | -0.76916 |
| Peripheral blood cells | Jurkat | 14.588 | 112.438 | 0.129742614 | -0.88692 |
| T-ALL cell line | Molt-3 | 13.67 | 113.677 | 0.120252998 | -0.9199 |
| Peripheral blood cells | Jurkat | 15.8 | 134.515 | 0.117459019 | -0.93011 |
| Embryonic stem cells | H1 | 2.118 | 18.616 | 0.113773098 | -0.94396 |
| cRCC | UMRC2 | 7.475 | 82.941 | 0.090124305 | -1.04516 |
| Embryonic stem cells | H1 | 0.089 | 30.747 | 0.002894591 | -2.53841 |
| Blood | GMP | -0.599 | 23.134 | -0.025892626 | N/A |
| Breast | Tumor_Frozen | -0.789 | 13.104 | -0.060210623 | N/A |
| Induced Pluripotent Stem Cells | BJ-RiPS | -1.02 | 9.478 | -0.107617641 | N/A |
| Breast | Tumor_Frozen | -4.689 | 20.137 | -0.232854944 | N/A |
| Breast | Tumor_Frozen | -9.605 | 18.162 | -0.528851448 | N/A |
| Breast | Normal_Frozen | -4.858 | 6.535 | -0.74338179 | N/A |
| Induced Pluripotent Stem Cells | 1-51N | -14.694 | 10.92 | -1.345604396 | N/A |
| AML | Patient_Normal | 3.699 | -1.847 | -2.002707093 | N/A |
| AML | Primary | -3.243 | 1.547 | -2.096315449 | N/A |
| AML | Primary | -3.795 | 1.27 | -2.988188976 | N/A |
| AML | Patient_Normal | 7.089 | -0.587 | -12.07666099 | N/A |
| Breast | Tumor_Frozen | -18.375 | 1.253 | -14.66480447 | N/A |
| Breast | Tumor_Frozen | -42.457 | 2.197 | -19.32498862 | N/A |
| AML | Patient_Normal | 14.177 | -0.729 | -19.44718793 | N/A |
| AML | MV4-11 | -4.87 | 0.13 | -37.46153846 | N/A |
| Ovary | Primary | 123.209 | -2.289 | -53.82656182 | N/A |
| Blood | Common Myeloid Progenitor, Donor B | 13.362 | -0.247 | -54.09716599 | N/A |
| AML | HL60 | -212.597 | 2.283 | -93.1217696 | N/A |
| AML | Primary | -10.351 | 0.055 | -188.2 | N/A |

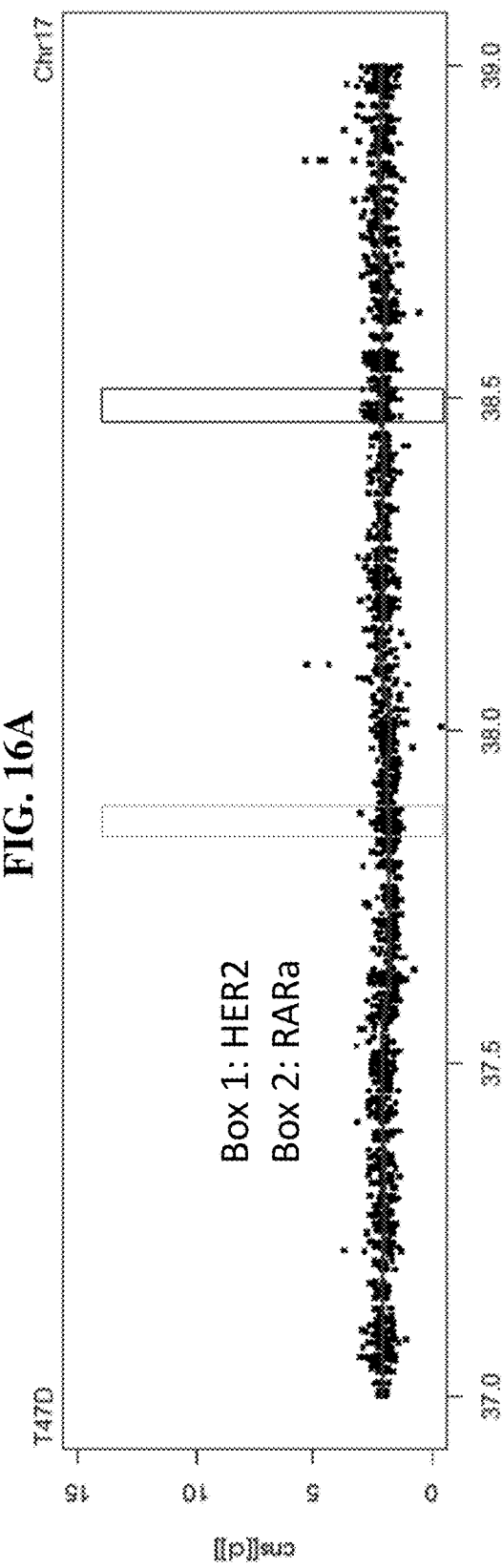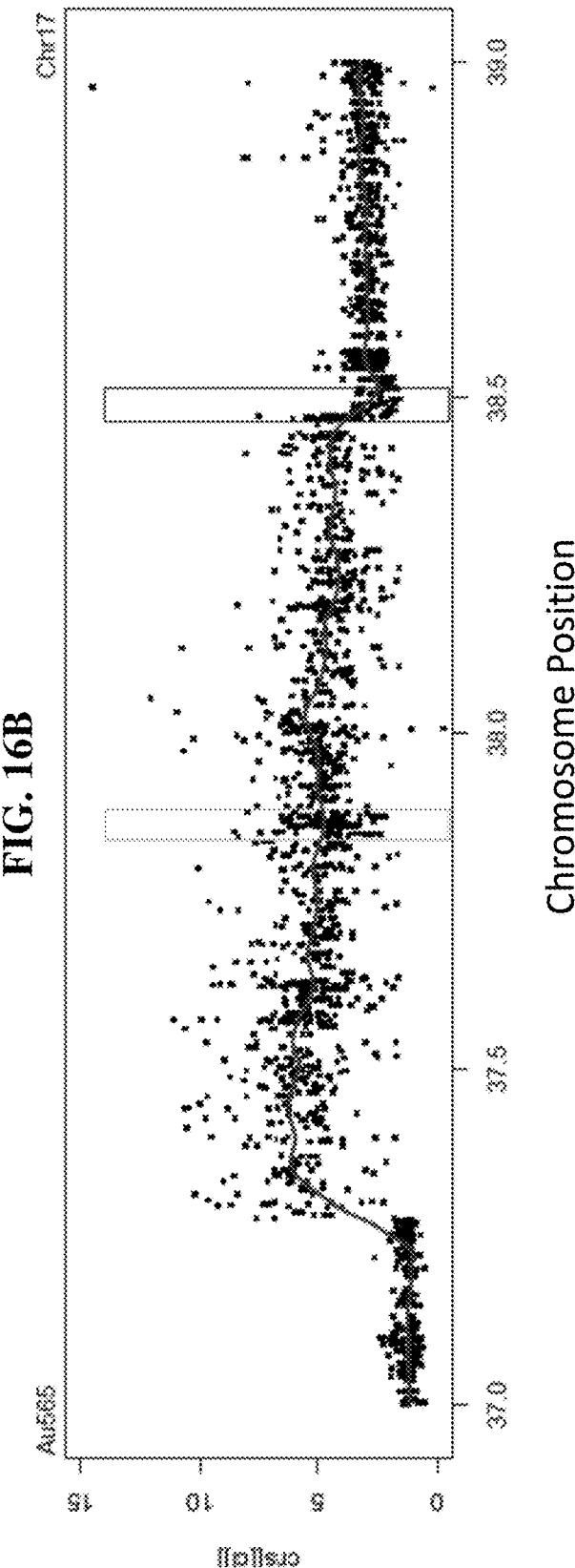
FIG. 16A
FIG. 16B
Box 1: HER2
Box 2: RARa

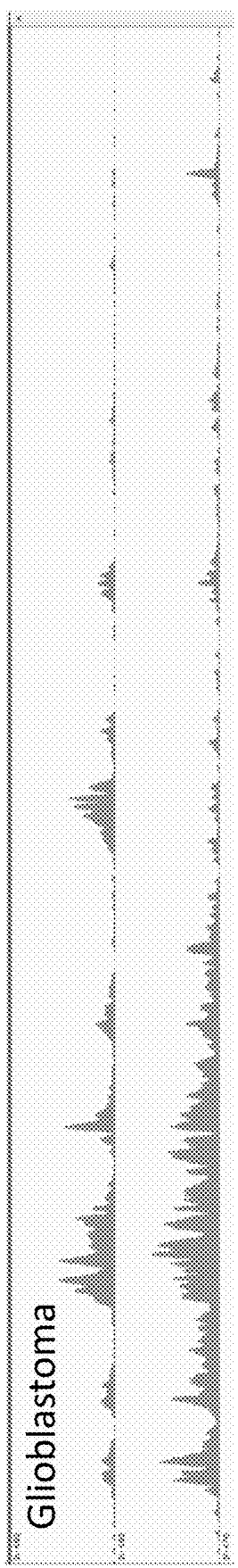
FIG. 17A Glioblastoma
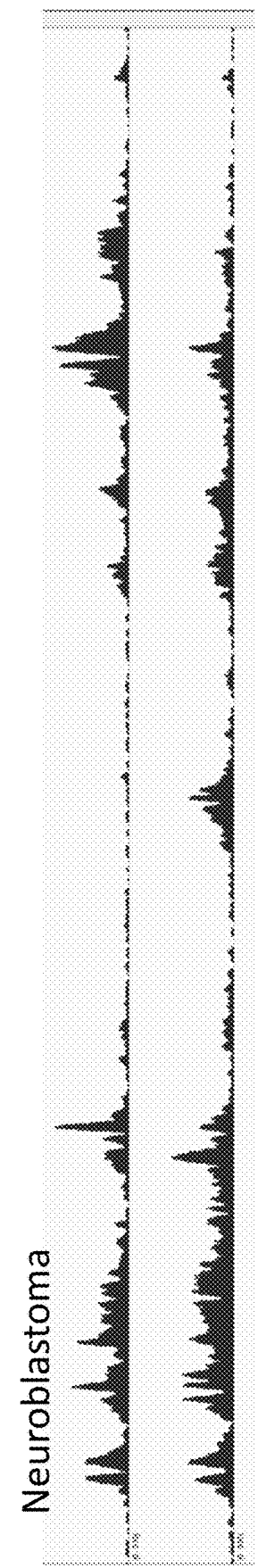
FIG. 17B Neuroblastoma
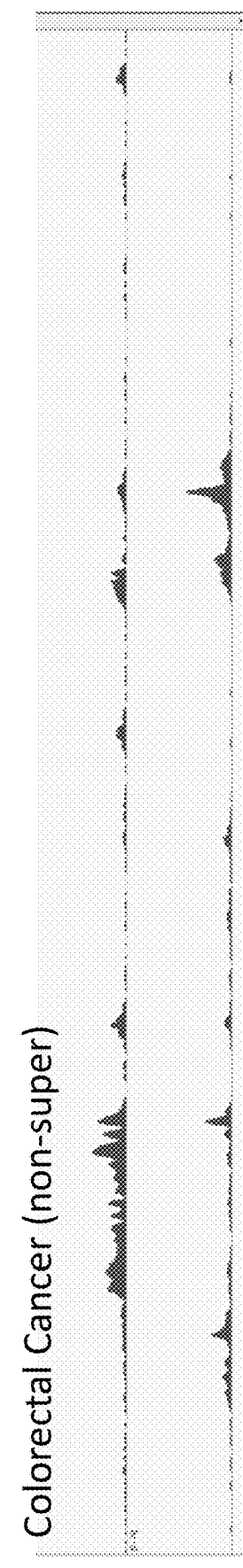
FIG. 17C Colorectal Cancer (non-super)

FIG. 30

| Cancer Type | Percent RARA mRNA above 2 SDs |
|---|---|
| AML | 6.94 |
| Brain lower grade glioma | 5.47 |
| Breast carcinoma | 9 |
| Cervical and Endocervical Carcinoma | 5.23 |
| Colon and rectal adenocarcinoma | 6.54 |
| Head and neck squamous carcinoma | 7.47 |
| Kidney renal papillary cell carcinoma | 15.5 |
| Lung adenocarcinoma | 7.74 |
| Pancreatic adenocarcinoma | 5.59 |
| Pheochromocytoma and Paraganglioma | 5.43 |
| Skin cutaneous melanoma | 6.79 |
| Uterine carcinoma | 19.3 |

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaacgtgtcc ccacctctc                                                    19

<210> SEQ ID NO 2
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagccaggc acataggg                                                    18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtcaccgcac tcacttccat                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaatagcgct cggtggagaa                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcctagtgg tccccttcc                                                   20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgaagattgt ttgcaccccc t                                                21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgctggtac ccagaagtga g                                                21

<210> SEQ ID NO 8
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgttgagttt tgccagtctc tt                                              22
```

METHODS OF STRATIFYING PATIENTS FOR TREATMENT WITH RETINOIC ACID RECEPTOR-ALPHA AGONISTS

CLAIM OF PRIORITY

This application is a continuation of U.S. patent application Ser. No. 15/799,519, filed Oct. 31, 2017, which is a continuation of U.S. patent application Ser. No. 15/172,045, filed Jun. 2, 2016, which is a continuation of International Application No. PCT/US2016/025256, filed Mar. 31, 2016, which claims the benefit of U.S. Provisional Application No. 62/268,203, filed Dec. 16, 2015, and U.S. Provisional Application No. 62/140,999, filed Mar. 31, 2015. The contents of each of the foregoing applications are incorporated herein by reference in their entirety.

BACKGROUND OF THE INVENTION

Retinoids are a class of compounds structurally related to vitamin A, comprising natural and synthetic compounds. Several series of retinoids have been found clinically useful in the treatment of dermatological and oncological diseases. Retinoic acid and its other naturally occurring retinoid analogs (9-cis retinoic acid, all-trans 3,4-didehydro retinoic acid, 4-oxo retinoic acid and retinol) are pleiotropic regulatory compounds that modulate the structure and function of a wide variety of inflammatory, immune and structural cells. They are important regulators of epithelial cell proliferation, differentiation and morphogenesis in lungs. Retinoids exert their biological effects through a series of hormone nuclear receptors that are ligand inducible transcription factors belonging to the steroid/thyroid receptor super family.

The retinoid receptors are classified into two families, the retinoic acid receptors (RARs) and the retinoid X receptors (RXRs), each consisting of three distinct subtypes ($\alpha$, $\beta$, and $\gamma$). Each subtype of the RAR gene family encodes a variable number of isoforms arising from differential splicing of two primary RNA transcripts. All-trans retinoic acid is the physiological hormone for the retinoic acid receptors and binds with approximately equal affinity to all the three RAR subtypes, but does not bind to the RXR receptors for which 9-cis retinoic acid is the natural ligand. Retinoids have anti-inflammatory effects, alter the progression of epithelial cell differentiation, and inhibit stromal cell matrix production. These properties have led to the development of topical and systemic retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis.

A limitation in the therapeutic use of retinoids has stemmed from the relative toxicity observed with the naturally occurring retinoids, all-trans retinoic acid and 9-cis retinoic acid. These natural ligands are non-selective in terms of RAR subtype and therefore have pleiotropic effects throughout the body, which are often toxic.

Various retinoids have been described that interact selectively or specifically with the RAR or RXR receptors or with specific subtypes ($\alpha$, $\beta$, $\gamma$) within a class. RARA specific agonists have held high promise for the treatment of cancers and many have entered human clinical trials. However, only one RARA specific agonist, tamibarotene, has ever been approved for the treatment of cancer. Moreover, tamibarotene is only approved in Japan and only for the treatment of acute promyelocytic leukemia, despite trials in the US and Europe. The disconnect between the theoretical efficacy of RARA agonists in cancer and the dearth of regulatory approvals for such agents raises the question of why such agonists are not effective and safe in humans. Therefore, there is a need to better understand why RARA agonists have not met their therapeutic potential.

Recent advances in genomic technology and the understanding of gene regulatory circuits has led to the discovery of super enhancers. Whereas many genes in a given tissue or cancer type may be regulated by the presence of enhancers in proximity to the gene coding region, a small minority of these represent a highly asymmetric and disproportionately large loading of transcriptional marks and machinery relative to all other active genes. Recent discoveries suggest that such enhancers are tied to genes of special relevance to the function and survival of the cell harboring them. As such, an association of a super enhancer with a gene indicates the relative significance of said gene to the survival of that cell. These observations may be useful in predicting the efficacy of various therapies.

SUMMARY OF THE INVENTION

The present disclosure provides technologies for detecting one or more of RARA super enhancer strength or ordinal rank, or RARA mRNA level that is equal to or above a threshold value. The present disclosure demonstrates that cells (e.g., cancer cells or cells from a subject suffering from MDS, e.g., AML cells, MDS cells, breast cancer cells) containing one or more of a RARA super enhancer strength or ordinal rank or a RARA mRNA level that is equal to or above a threshold value are more sensitive to the anti-cancer effect of a RARA agonist (e.g., a gain-of-function RARA agonist; or a RARA-specific agonist (e.g., an agonist that is at least 10×, 100×, 1000×, 10000× or more specific for RAR-$\alpha$, than for either of RAR-$\beta$ or RAR-$\gamma$)) than cells that are below such threshold value.

The various embodiments, aspects and alternatives of this invention solve the problem of defining which cellular populations are sensitive to agonists of retinoic acid receptor alpha ("RARA"), identifying patient subgroups that will benefit from treatment with RARA agonists (e.g., stratifying patients for treatment with a RARA agonist; separating RARA agonist responders from non-responders) and providing treatment therapies directed at such patient subgroups. The solution is based, at least in part, upon our discovery that a super-enhancer having a strength or ordinal rank equal to or above a threshold value and associated with a gene encoding retinoic acid receptor alpha ("RARA") in certain cancer cells is indicative that such cell will respond to treatment with a RARA agonist. We have also discovered that RARA primary RNA transcript levels, in particular mRNA levels, equal to or above a threshold level in certain cancer cells are also indicative that such cancer cells will respond to treatment with a RARA agonist. In both cases, the threshold values associated with these parameters appear to be significantly more predictive than RARA protein levels.

In a first embodiment, the invention relates to a method of treating a subject suffering from cancer, wherein cancer cells in the subject have been determined to have one or more of:

a. a super enhancer associated with a RARA gene, wherein the super enhancer has a strength, or ordinal rank that is equal to or above a pre-determined threshold level; or b. a level of primary RNA transcript from the RARA gene and/or a portion of the super enhancer associated therewith that is equal to or above a pre-determined threshold level, wherein the method comprises the step of administering to the subject an agonist of RARA.

In some aspects of the first embodiment an agonist of RARA is only administered if the super enhancer has a strength or ordinal rank that is equal to or above a pre-determined threshold level; or the level of primary RNA transcript is equal to or above a pre-determined threshold level.

In some aspects of the first embodiment, when the cancer cells in the subject have been determined to have:
 a. an enhancer or super enhancer associated with a RARA gene, wherein the enhancer or super enhancer has a strength, or ordinal rank that is below a pre-determined threshold level; or
 b. a level of primary RNA transcript from the RARA gene and/or a portion of the super enhancer associated therewith that is below a pre-determined threshold level, the method comprises the step of administering to the subject a therapeutic other than an agonist of RARA.

In some aspects of the first embodiment, the cancer cells in the subject have been determined to have a super enhancer associated with a RARA gene that is at least 1.75-fold stronger than a portion of a super enhancer associated with MALAT1 as measured by ChIP-seq, wherein the portion is located at chr11:65263724-65266724 in genome build hg19, or at least an equivalent amount stronger than another reference enhancer or super enhancer locus.

In other aspects of the first embodiment, when the cancer cells in the subject have been determined to meet either a. or b., the method comprises administering to the subject a therapeutic (e.g., a therapeutic agent or standard of care) other than an agonist of RARA, e.g., a chemotherapeutic agent or transplantation. In some embodiments, the subject has a cancer, e.g., a leukemia (e.g., acute myeloid leukemia). Exemplary therapeutics include chemotherapeutic agents (e.g., cytarabine, gemcitabine, azacitidine, decitabine, fluorouracil, or an anthracycline (e.g., daunorubicin, doxorubicin, epirubicin, or idarubicin)) or transplantation (e.g., stem cell transplantation).

In alternate aspects of the first embodiment, the cancer cells in the subject have been determined to have one of the following:
 a. a super enhancer associated with a RARA gene that is at least 1.5-fold higher in strength than a corresponding enhancer associated with a RARA gene in a human cell or human cell line known to be non-responsive to a RARA agonist; and/or
 b. a RARA RNA primary transcript level that is at least 1.5-fold higher than a corresponding RARA RNA primary transcript level in a human cell or human cell line known to be non-responsive to a RARA agonist.

In other alternate aspects of the first embodiment, the cancer cells in the subject have been determined to have one the following:
 a. a super enhancer associated with a RARA gene that has a strength corresponding to a prevalence rank that is equal to or above a pre-determined prevalence cutoff for RARA gene super enhancer strength; and/or
 b. a super enhancer associated with a RARA gene that has a strength that is equal to or above a pre-determined RARA gene strength cutoff; and/or
 c. a super enhancer associated with a RARA gene that has an ordinal of strength corresponding to a prevalence rank that is equal to or above a pre-determined RARA gene strength ordinal prevalence cutoff; and/or d. a super enhancer associated with a RARA gene that has an ordinal of strength that is equal to or above a pre-determined RARA gene strength ordinal cutoff; and/or
 e. a RARA mRNA level that is equal to or above a pre-determined mRNA level cutoff; and or
 f. a RARA mRNA level corresponding to a prevalence rank that is equal to or above a pre-determined RARA mRNA prevalence cutoff.

In certain more specific aspects, any of the pre-determined prevalence cutoffs set forth above is determined:
 a. from a rank ordering of RARA super-enhancer strength in a population of samples from the same type of cancer cells, wherein at least one sample has been determined to be responsive to the RARA agonist; and/or
 b. from a rank ordering of RARA super-enhancer strength ordinal in a population of samples from the same type of cancer cells, wherein at least one sample has been determined to be responsive to the RARA agonist; and/or
 c. from a rank ordering of RARA mRNA levels in a population of samples of the same type of cancer cells wherein at least one sample has been determined to be responsive to the RARA agonist.

In a second embodiment, the invention provides a method of treating a subject suffering from cancer comprising the steps of:
 a. receiving information related to one or more of:
  i. strength, ordinal rank or prevalence rank of a super enhancer associated with a RARA gene in a cancer cell from the subject; or
  ii. level of primary RNA transcript from the RARA gene and/or a portion of the super enhancer associated therewith in a cancer cell from the subject; and
 b. administering to the subject an agonist of RARA if the information indicates one or more of:
  i. the super enhancer has a strength, ordinal rank, or prevalence rank that is equal to or above a pre-determined threshold level; or
  ii. the level of RNA transcript is equal to or above a pre-determined threshold level.

In one aspect of the second embodiment, the subject is administered a therapeutic other than an agonist of RARA if the information indicates:
 iii. the super enhancer has a strength, ordinal rank, or prevalence rank that is below a pre-determined threshold level; or
 iv. the level of RNA transcript is below a pre-determined threshold level.

In one aspect of the second embodiment, step a. comprises receiving information related to one or more of:
 i. the strength of a super enhancer associated with a RARA gene compared to a control enhancer or super enhancer in the same cancer; and/or
 ii. the level of a RARA RNA primary transcript level compared to a corresponding RARA RNA primary transcript level in a human cell or human cell line known to be non-responsive to a RARA agonist.

In one aspect of the second embodiment, step b comprises administering to the subject an agonist of RARA if the information indicates one or more of:
 i. the super enhancer associated with a RARA gene is at least 1.75-fold stronger than a portion of a super enhancer associated with MALAT1 located at chr11: 65263724-65266724 in genome build hg19, or at least an equivalent amount stronger than another reference enhancer or super enhancer locus; and/or
 ii. a RARA RNA primary transcript level that is at least 1.5-fold higher than a corresponding RARA RNA primary transcript level in a human cell or human cell line known to be non-responsive to a RARA agonist.

In an alternate aspect of the second embodiment, step a. comprises receiving information related to one or more of:
  i. the strength of a super enhancer associated with a RARA gene and/or the prevalence rank of RARA gene super enhancer strength in a population to which the strength corresponds; and/or
  ii. the ordinal rank of the strength of a super enhancer associated with a RARA gene as compared to other super enhancers in the cell and/or the prevalence rank of a RARA gene super enhancer strength ordinal in a population to which the ordinal rank corresponds; and/or
  iii. RARA mRNA level and/or the prevalence rank of RARA mRNA level in a population to which the mRNA level corresponds; and
step b. comprises administering to the subject an agonist of RARA if the information indicates one or more of:
  i. the strength of a super enhancer associated with a RARA gene is equal to or above a pre-determined cutoff value of RARA gene super enhancer strength in a population; and/or
  ii. the strength of a super enhancer associated with a RARA gene corresponds to a prevalence rank that is equal to or above a pre-determined prevalence cutoff of RARA gene super enhancer strength in a population; and/or
  iii. the ordinal rank of the strength of a super enhancer associated with a RARA gene is equal to or above a pre-determined ordinal cutoff value of RARA gene super enhancer strength ordinal in a population; and/or
  iv. the ordinal rank of strength of a super enhancer corresponds to a prevalence rank that is equal to or above a pre-determined prevalence cutoff of RARA gene super enhancer strength ordinal in a population; and/or
  v. the level of RARA mRNA is equal to or above a RARA mRNA level that corresponds to a pre-determined cutoff value of RARA mRNA level in a population; and/or
  vi. the RARA mRNA level corresponds to a prevalence rank that is equal to or above a pre-determined prevalence cutoff of RARA mRNA level in a population.

In a third embodiment, the invention provides a packaged pharmaceutical composition comprising:
  a. a RARA agonist; and
  b. a written insert or label comprising instructions to use the RARA agonist in a subject suffering from a cancer, and whose cancer cells have been determined to have one or more of:
    i. a super enhancer associated with a RARA gene, wherein the super enhancer has a strength, ordinal rank or prevalence rank that is equal to or above a pre-determined threshold level; or
    ii. a level of primary RNA transcript from the RARA gene and/or a portion of the super enhancer associated therewith that is equal to or above a pre-determined threshold level.

In some aspects of the third embodiment, the written insert or label comprises instructions to use the RARA agonist in a subject whose cancer cells that have been determined to have one or more of:
  i. a super enhancer associated with a RARA gene that is at least 1.75-fold stronger than a portion of a super enhancer associated with MALAT1 located at chr11: 65263724-65266724 in genome build hg19, or at least an equivalent amount stronger than another reference enhancer or super enhancer locus; and/or
  ii. a RARA RNA primary transcript level that is at least 1.5-fold higher than a corresponding RARA RNA primary transcript level in a human cell or human cell line known to be non-responsive to a RARA agonist.

In some aspects of the third embodiment, the written insert or label comprises instructions to use the RARA agonist in a subject whose cancer cells that have been determined to have one or more of:
  i. a super enhancer associated with a RARA gene that has a strength that is equal to or above a a pre-determined cutoff value of RARA gene super enhancer strength in a population; and/or
  ii. super enhancer associated with a RARA gene that has a strength corresponding to a prevalence rank that is equal to or above a pre-determined prevalence cutoff of RARA gene super enhancer strength in a population; and/or
  iii. a super enhancer associated with a RARA gene that has an ordinal rank of the strength that is equal to or above a pre-determined cutoff value of RARA gene super enhancer strength ordinal in a population; and/or
  iv. a super enhancer associated with a RARA gene that has an ordinal rank of strength corresponding to a prevalence rank of that is equal to or above a pre-determined RARA gene super enhancer strength ordinal prevalence cutoff of in a population; and/or
  v. a level of RARA mRNA that is equal to or above a pre-determined RARA mRNA level cutoff value in a population; and/or
  vi. a RARA mRNA level corresponding to a prevalence rank that is equal to or above a pre-determined of RARA mRNA prevalence cutoff in a population.

In a fourth embodiment, the invention provides a method of predicting the efficacy of a RARA agonist in a treatment of a cancer in a subject comprising the step of determining if, having determined if, or receiving information that:
  a. a super enhancer associated with a RARA gene in the cancer has a strength, ordinal rank or prevalence rank that is equal to or above a pre-determined threshold level; or
  b. a level of primary RNA transcript from the RARA gene and/or a portion of the super enhancer associated therewith in the cancer is equal to or above a pre-determined threshold level, wherein any of a. or b. is predictive of RARA agonist efficacy in the treatment.

In some aspects of the fourth embodiment predicting the efficacy of a RARA agonist in the treatment of the cancer in a subject comprises the step of determining if the cancer is characterized by one or more of:
  a. a super enhancer associated with a RARA gene is at least 1.75-fold stronger than a portion of a super enhancer associated with MALAT1 located at chr11: 65263724-65266724 in genome build hg19, or at least an equivalent amount stronger than another reference enhancer or super enhancer locus; and/or
  b. a RARA RNA primary transcript level that is at least 1.5-fold higher than a corresponding RARA RNA primary transcript level in a human cell or human cell line known to be non-responsive to a RARA agonist;
wherein any of a. or b. is predictive of RARA agonist efficacy in the treatment.

In some aspects of the fourth embodiment predicting the efficacy of a RARA agonist in the treatment of the cancer in a subject comprises the step of determining if the cancer is characterized by one or more of:

a. a super enhancer associated with a RARA gene that has a strength that is equal to or above a pre-determined cutoff value of RARA gene super enhancer strength in a population; and/or
b. a super enhancer associated with a RARA gene that has a strength corresponding to a prevalence rank that is equal to or above a pre-determined prevalence cutoff of RARA gene super enhancer strength in a population; and/or
c. a super enhancer associated with a RARA gene that has an ordinal rank of the strength of that is equal to or above a pre-determined cutoff value of RARA gene super enhancer strength ordinal in a population; and/or
d. a super enhancer associated with a RARA gene that has an ordinal rank of strength corresponding to a prevalence rank of that is equal to or above a pre-determined prevalence cutoff of RARA gene super enhancer strength ordinal in a population; and/or
e. a level of RARA mRNA that is equal to or above a pre-determined cutoff value of RARA mRNA level in a population; and/or
f. a level of RARA mRNA that corresponds to a prevalence rank that is equal to or above a pre-determined prevalence cutoff of RARA mRNA level in a population.

In a fifth embodiment, the invention provides a method of diagnosing, prognosing or treating a subject suffering from a cancer comprising the steps of:
a. obtaining a sample of cancer cells from the subject;
b. determining, having determined, or receiving information about one or more of:
  i. the strength, ordinal rank or prevalence rank of a super enhancer associated with a RARA gene in the sample; or
  ii. the level of primary RNA transcript from the RARA gene and/or a portion of the super enhancer associated therewith in the sample; and
c. administering a therapeutic composition comprising a RARA agonist if one or more of:
  i. the super enhancer has a strength, ordinal rank or prevalence rank that is equal to or above a pre-determined threshold level; or
  ii. the level of primary RNA transcript is equal to or above a pre-determined threshold level.

In one aspect of the fifth embodiment, step b. comprises determining in the sample one or more of:
  i. the strength of a super enhancer associated with a RARA gene compared to a control enhancer or super enhancer in the same cancer; and/or
  ii. the level of a RARA RNA primary transcript level compared to a corresponding RARA RNA primary transcript level in a human cell or human cell line known to be non-responsive to a RARA agonist.

In another aspect of the fifth embodiment, step c. comprises administering or recommending the administration of a therapeutic composition comprising a RARA agonist if one or more of:
  i. the super enhancer associated with a RARA gene is at least 1.75-fold stronger than a portion of a super enhancer associated with MALAT1 located at chr11: 65263724-65266724 in genome build hg19, or at least an equivalent amount stronger than another reference enhancer or super enhancer locus;
  ii. a RARA RNA primary transcript level that is at least 1.5-fold higher than a corresponding RARA RNA primary transcript level in a human cell or human cell line known to be non-responsive to a RARA agonist; and/or
  iii. the RARA mRNA level is at least 1.5-fold higher than the RARA mRNA level in a human cell or human cell line known to be non-responsive to a RARA agonist.

In another aspect of the fifth embodiment, step b. comprises determining in the sample one or more of:
  i. strength of a super enhancer associated with a RARA gene and/or the prevalence rank of strength of a super enhancer associated with a RARA gene in a population to which the strength corresponds; and/of
  ii. ordinal rank of the strength of a super enhancer associated with a RARA gene as compared to other super enhancers in the cell and/or the prevalence rank of the ordinal rank of the strength of a super enhancer associated with a RARA gene in a population to which the ordinal rank corresponds; and/or
  iii. RARA mRNA primary transcript level and/or the prevalence rank of the RARA mRNA primary transcript in a population to which the mRNA level corresponds.

In another aspect of the fifth embodiment, step c. comprises administering or recommending the administration of a therapeutic composition comprising a RARA agonist if one or more of:
a. a super enhancer associated with a RARA gene had a strength that is equal to or above a pre-determined cutoff value of RARA gene super enhancer strength in a population; and/or
b. a super enhancer associated with a RARA gene that has a strength corresponding to a prevalence rank that is equal to or above a pre-determined prevalence cutoff of RARA gene super enhancer strength in a population; and/or
c. a super enhancer associated with a RARA gene that has an ordinal rank of strength that is equal to or above a pre-determined cutoff value of RARA gene super enhancer strength ordinal in a population; and/or
d. a super enhancer associated with a RARA gene that has an ordinal rank of strength corresponding to a prevalence rank of that is equal to or above a pre-determined prevalence cutoff of RARA gene super enhancer strength ordinal in a population; and/or
e. a level of RARA mRNA is equal to or above a a pre-determined cutoff value of RARA mRNA level in a population; and/or
f. a level of RARA mRNA that corresponds to a prevalence rank that is equal to or above a pre-determined prevalence cutoff of RARA mRNA level in a population.

In a sixth embodiment, the invention provides a method of determining the level of RARA mRNA in a subject, comprising the steps of: a) obtaining total mRNA from a biological sample from the subject; b) appending to each mRNA molecule additional nucleotides not naturally appended to such mRNA molecules to enable the mRNA molecules to bind to a solid support; c) sequencing the mRNA molecules; and d) determining the level of RARA mRNA.

In an alternate sixth embodiment the invention provides a method of determining the level of RARA mRNA in a subject, comprising the steps of: a) obtaining total mRNA from a biological sample from the subject; b) creating a cDNA library from the total mRNA; and c) combining the cDNA library with (i) a primer pair that is specific for cDNA created from RARA mRNA; (ii) a DNA polymerase; and (iii) a component for detection of any DNA molecules produced from the primer pair and the DNA polymerase. In some aspects of this alternate sixth embodiment, the component for detection is a dye. In other aspects of this alternate sixth embodiment, the component for detection is a labelled (e.g., radiolabelled or dye-labelled, oligonucleotide.

In some aspects of any of the sixth embodiments, the level of mRNA detected in the subject is compared to a pre-determined threshold level.

In some aspects of any of the sixth embodiments, the patient is suffering from a cancer selected from AML, breast cancer or MDS. In more specific aspects, the subject is suffering from one of the above diseases and is administered a RARA agonist (e.g., tamibarotene) if the determined RARA mRNA level is equal to or above the pre-determined threshold.

In some aspects of any of the sixth embodiments, the pre-determined threshold is a RARA mRNA cutoff level determined by measuring RARA mRNA levels in a population or population of samples having or representing the same cancer; and identifying at least one population member that is responsive to a RARA agonist. In some aspects of this sixth embodiment, the pre-determined threshold is a RARA mRNA cutoff level that is determined by calculating a prevalence cutoff based on RARA super-enhancer ordinal rank in a population or population of samples wherein at least one population member is identified as being responsive to a RARA agonist; and using the calculated prevalence cutoff to determine a cutoff level of RARA mRNA levels in the same or a different population or population of samples.

In a seventh embodiment, the invention provides a composition comprising (i) cDNA reversed transcribed from mRNA obtained from a population of cancer cells in a subject (e.g., bone marrow cells from a subject suffering from AML or MDS, breast cancer cells, etc.); (ii) a primer pair specific for cDNA transcribed from RARA mRNA; (iii) a DNA polymerase; and (iv) a component for detection of any DNA molecules produced from the primer pair and the DNA polymerase. In some aspects of this seventh embodiment, the component for detection is a dye. In other aspects of this seventh embodiment, the component for detection is a labelled (e.g., radiolabelled or dye-labelled, oligonucleotide. In some aspects of this seventh embodiment, the composition is used to determine RARA mRNA level in the subject. In more specific aspects of this seventh embodiment, the determined RARA mRNA levels are compared to a cutoff value and the comparison is utilized to determine whether the patient should be administered a RARA agonist (e.g., tamibarotene).

In an eighth embodiment, the invention provides a differential method of treating a set of subjects suffering from cancer comprising administering a RARA agonist to a subset of subjects whose cancer is characterized by a RARA mRNA level that is equal to or above a pre-determined threshold; and not administering a RARA agonist to a subset of subjects whose cancer is characterized by a RARA mRNA level that is below a pre-determined threshold.

In some aspects of this eighth embodiment, the set of subjects is suffering from the same cancer and the cancer is selected from AML, breast cancer or MDS. In some aspects of the seventh embodiment, the RARA agonist is tamibarotene. In some aspects of this seventh embodiment, the pre-determined threshold is an mRNA cutoff level determined by measuring RARA mRNA levels in a population or population of samples having or representing the same cancer; and identifying at least one population member that is responsive to a RARA agonist. In some aspects of this seventh embodiment, the pre-determined threshold is a mRNA cutoff level determined by calculating a prevalence cutoff based on RARA super-enhancer ordinal rank in a population or population of samples wherein at least one population member is identified as being responsive to a RARA agonist; and using the calculated prevalence cutoff to determine a cutoff level of RARA mRNA levels in the same or a different population or population of samples.

In a ninth embodiment, the invention provides a method comprising the steps of:
a. obtaining cancer cells from a subject suffering from cancer; and
b. measuring in the cancer cells:
   i. the strength, ordinal rank or prevalence rank of a super enhancer associated with a RARA gene in the sample; or
   ii. the level of primary RNA transcript from the RARA gene and/or a portion of the super enhancer associated therewith in the sample; and
c. comparing the measurement obtained in step b. to a threshold value.

In any and all embodiments, in some aspects, the present invention features a pharmaceutical composition for use in treating a subject suffering from cancer, wherein the composition comprises an agonist of RARA.

The details of one or more embodiments of the invention are set forth herein. Other features, objects, and advantages of the invention will be apparent from the Detailed Description, the Figures, the Examples, and the Embodiments.

BRIEF DESCRIPTION OF THE DRAWINGS

FIGS. 3A-3M are listings of ChIP-seq results for a wide variety of cell lines and patient samples. It shows the relative strength of the RARA super enhancer as compared to a portion of the MALAT1 super enhancer in each of these cells or patient samples.

FIGS. 16A-16B depict the HER2 and RARA gene copy numbers in a tamibarotene weakly responsive (T47D, FIG. 16A) and a highly responsive (AU565, FIG. 16B) breast cancer cell line.

FIGS. 17A-17C depict the level of H3K27Ac reads across the RARA locus as determined by ChIP-seq for glioblastoma (FIG. 17A), neuroblastoma (FIG. 17B), and colorectal (FIG. 17C) cancer patient samples.

FIG. 30 is a table of different cancer types where greater than 5% of the samples tested had RARA mRNA levels at least 2 standard deviations above the mean.

DEFINITIONS

Figure 1B:
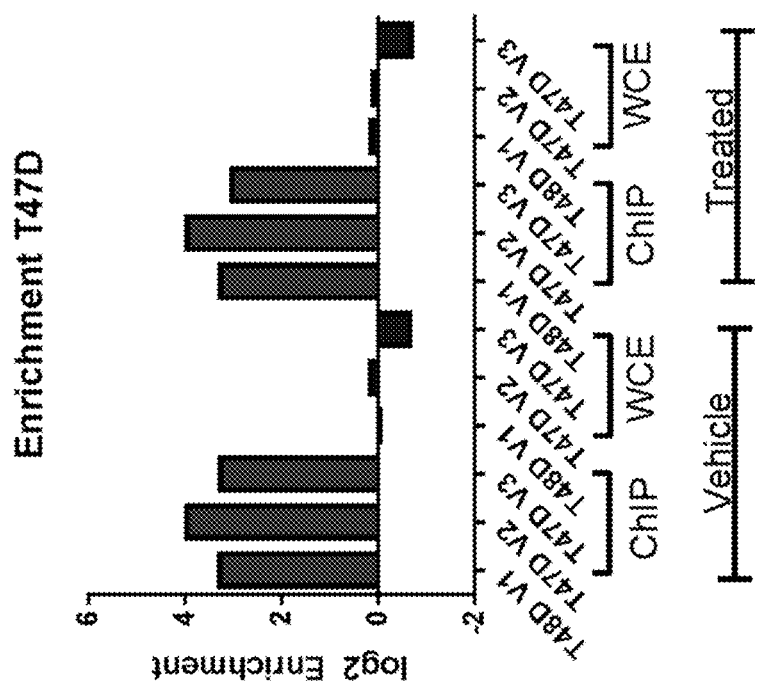
FIGS. 1A-1B graphically depict the log 2 enrichment of RARA super enhancer as measured by ChIP-qPCR.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, MALAT1e, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein, such as of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal. In certain embodiments, the subject is a human.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat," and "treating" require that signs or symptoms of the disease disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound described herein, such as of Formula (I) refers to an amount sufficient to elicit the desired biological response, i.e., treating the condition. As will be appreciated by those of ordinary skill in this art, the effective amount of a compound described herein, such as of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound described herein, such as of Formula (I) is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm (*Stedman's Medical Dictionary*, 25th ed.; Hensly ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus. In some aspect, a biological sample from a subject suffering from AML or MDS is a bone marrow aspirate.

The term "RARA gene" refers to a genomic DNA sequence that encodes a functional retinoic acid receptor-α and specifically excludes gene fusions that comprise all or a portion of the RARA gene. In some embodiments, the RARA gene is located at chr17:38458152-38516681 in genome build hg19.

The term "enhancer" refers to a region of genomic DNA acting to regulate genes up to 1 Mbp away. An enhancer may overlap, but is often not composed of, gene coding regions. An enhancer is often bound by transcription factors and designated by specific histone marks.

The term "super enhancer" refers to a subset of enhancers that contain a disproportionate share of histone marks and/or transcriptional proteins relative to other enhancers in a particular cell. Because of this, a gene regulated by a super enhancer is predicted to be of high importance to the function of that cell. Super enhancers are typically determined by rank ordering all of the enhancers in a cell based on strength and determining using available software such as ROSE (https://bitbucket.org/young_computation/rose), the subset of enhancers that have significantly higher strength than the median enhancer in the cell (see, e.g., U.S. Pat. No. 9,181,580, which is herein incorporated by reference.

The term "primary RNA transcript" as used herein refers to the RNA transcription product from the DNA sequence that include one or more of the gene coding region, and an enhancer, or a super enhancer associated with that gene. In some embodiments, the term "primary RNA transcript" is interchangeable with the term "eRNA" or "enhancer RNA" when such RNA includes RNA derived from the DNA corresponding to the enhancer region. In other embodiments, the term "primary RNA transcript" refers to the mRNA transcribed from the gene coding region.

The term "strength" when referring to a portion of an enhancer or a super enhancer, as used herein means the area under the curve of the number of H3K27Ac or other genomic marker reads plotted against the length of the genomic DNA segment analyzed. Thus, "strength" is an integration of the signal resulting from measuring the mark at a given base pair over the span of the base pairs defining the region being chosen to measure.

The term "prevalence rank" for a specified value (e.g., the strength of a super enhancer associated with a RARA gene) means the percentage of a population that are equal to or greater than that specific value. For example a 35% prevalence rank for the strength of a super enhancer associated with a RARA gene in a test cell means that 35% of the population have a RARA gene enhancer with a strength equal to or greater than the test cell.

The term "prevalence cutoff" for a specified value (e.g., the strength of a super enhancer associated with a RARA gene) means the prevalence rank that defines the dividing line between two subsets of a population (e.g., responders and non-responders). Thus, a prevalence rank that is equal to or higher (i.e., a lower percentage value) than the prevalence cutoff defines one subset of the population; and a prevalence rank that is lower (e.g., a higher percentage value) than the prevalence cutoff defines the other subset of the population.

The terms "cutoff" and "cutoff value" mean a value measured in an assay that defines the dividing line between two subsets of a population (e.g., responders and non-responders). Thus, a value that is equal to or higher than the cutoff value defines one subset of the population; and a value that is lower than the cutoff value defines the other subset of the population.

The terms "threshold" and "threshold level" mean a level that defines the dividing line between two subsets of a population (e.g., responders and non-responders). A threshold level may be a prevalence cutoff or a cutoff value.

The term "population" or "population of samples" means a sufficient number (e.g., at least 30, 40, 50 or more) of different samples that reasonably reflects the distribution of the value being measured in a larger group. Each sample in a population of samples may be a cell line, a biological sample obtained from a living being (e.g., a biopsy or bodily fluid sample), or a sample obtained from a xenograft (e.g., a tumor grown in a mouse by implanting a cell line or a patient sample), wherein each sample is from a living being suffering from or from a cell line or xenograft representing, the same disease, condition or disorder.

The term "ordinal rank" of a specified value means the rank order of that value as compared to a set of other values. For example, an ordinal rank of 100 in terms of the strength of a super enhancer associated with a RARA gene in a test cell as compared to other super enhancers in the test cell means that 99 other super enhancers in the test cell had greater strength than the super enhancer associated with a RARA gene.

The term "rank ordering" means the ordering of values from highest to lowest or from lowest to highest.

DETAILED DESCRIPTION OF CERTAIN EMBODIMENTS OF THE INVENTION

RARA Super-Enhancer Identification and Determination of Threshold Levels

The identification of an enhancer or super enhancer may be achieved by various methods known in the art, for example as described in Cell 2013, 155, 934-947 and PCT/US2013/066957, both of which are incorporated herein by reference. In some embodiments, the identification of a super enhancer is achieved by obtaining cellular material and DNA from a cancer sample in a patient (e.g., from a biopsy). The important metrics for enhancer measurement occur in two dimensions—the length of the DNA over which genomic markers (e.g., H3K27Ac) are contiguously detected—and the compiled incidence of genomic marker at each base pair along that span of DNA constituting the magnitude. The measurement of the area under the curve ("AUC") resulting from integration of length and magnitude analysis determines the strength of the enhancer. It is the strength of the RARA super enhancer relative to a control that is used in one aspect of the present invention to determine whether or not a subject will be responsive a RARA agonist. It will be readily apparent to those of skill in the art that if the length of DNA over which the genomic markers is detected is the same for both RARA and the control, then the ratio of the magnitude of the RARA super enhancer relative to the control will be equivalent to the strength and may also be used to determine whether or not a subject will be responsive a RARA agonist.

We have determined through H3K27Ac ChIP-seq methods that there is a super-enhancer locus associated with the RARA gene at chr17:38458152-38516681 (genome build hg19). This locus actually overlaps the RARA gene locus itself and therefore was considered to be a super-enhancer locus associated with that gene because of proximity/overlap. Thus, in some embodiments, determination of the strength of a super-enhancer associated with the RARA gene according to the present invention only requires analysis of this specific portion of the genome, as opposed to requiring an analysis of the entire genome.

ChIP-sequencing, also known as ChIP-seq, is used to analyze protein interactions with DNA. ChIP-seq combines chromatin immunoprecipitation (ChIP) with massively parallel DNA sequencing to identify the binding sites of DNA-associated proteins. It can be used to map global binding sites precisely for any protein of interest. Previously, ChIP-on-chip was the most common technique utilized to study these protein-DNA relations. Successful ChIP-seq is dependent on many factors including sonication strength and method, buffer compositions, antibody quality, and cell number; see, e.g., T. Furey, Nature Reviews Genetics 13, 840-852 (December 2012); M. L. Metzker, Nature Reviews Genetics 11, 31-46 (January 2010); and P. J Park, Nature Reviews Genetics 10, 669-680 (October 2009)). Genomic markers other that H3K27Ac that can be used to identify super enhancers using ChIP-seq include, P300, CBP, BRD2, BRD3, BRD4, components of the mediator complex (J Loven, et al., Cell, 153(2):320-334, 2013), histone 3 lysine 4 monomethylated (H3K4me1), or other tissue specific enhancer tied transcription factors (E Smith & A Shilatifard, Nat Struct Mol Biol, 21(3):210-219, 2014) (S Pott & Jason Lieb, Nature Genetics, 47(1):8-12, 2015).

In some embodiments, H3K27ac or other marker ChIP-seq data super-enhancer maps of the entire genome of a cell line or a patient sample already exist. In these embodiments, one would simply determine whether the strength, or ordinal rank of the enhancer or super-enhancer in such maps at the chr17:38458152-38516681 (genome build hg19) locus was equal to or above the pre-determined threshold level.

In some embodiments, determination of whether or not the strength of the enhancer or super-enhancer at the chr17:38458152-38516681 locus requires a comparison of the ChIP-seq reads in this region to a region known to comprise a ubiquitous super-enhancer or enhancer that is present at similar levels in all cells. One example of such a ubiquitous super-enhancer region is the MALAT1 super-enhancer locus (chr11:65263724-65266724). By comparing the ChIP-seq reads at the RARA locus with that at the MALAT1 locus, one can determine whether or not the strength of a super-enhancer at the RARA locus is equal to or above the predetermined threshold level and whether or not the cells therein will respond to a RARA agonist.

In some embodiments of the present invention, the threshold level is when $\log_{10}$ (AUC of ChIP-seq reads at the RARA locus ("R")/AUC of ChIP-seq reads at the MALAT1 super-enhancer locus ("M")) is 0.25 or greater. In some aspects of these embodiments, the threshold level for identifying responders to a RARA agonist is $\log_{10}$ (R/M) of 0.3 or greater, 0.35 or greater, or 0.4 or greater.

In some embodiments of the present invention, the threshold level is when (AUC of ChIP-seq reads at the RARA locus ("R")/AUC of ChIP-seq reads at the MALAT1 super-enhancer locus ("M")) is 1.75 or greater. In some aspects of these embodiments, the threshold level for identifying responders to a RARA agonist is $\log_{10}$ (R/M) of 2.0 or greater, 2.25 or greater, or 2.75 or greater.

In some embodiments of the present invention R, as defined above, is compared to a control enhancer or super enhancer locus other than MALAT1 (the number of ChIP-seq reads at this other control enhancer or super enhancer is referred to as "C"). When another control enhancer or super enhancer locus, C, is utilized, the threshold values expressed as $\log_{10}$ ("V"), referred to above for comparison to M, e.g., $\log_{10}(R/M) \geq 0.25$, $\log_{10}(R/M) \geq 0.3$, $\log_{10}(R/M) \geq 0.35$, or $\log_{10}(R/M) \geq 0.4$, must be adjusted to an equivalent value to compare to C in order to account for the relative strength of C as compared to M. This "equivalent adjusted threshold value" ("A") is calculated as follows:

$$A = \log_{10}(M/C) + V$$

As a non-limiting example, if the calculated strength of the MALAT1 super enhancer (M) is 10-fold greater than the control enhancer or super enhancer used as a comparator (C), and the threshold value (V) is 0.25, then $A = \log_{10}(10) + 0.25 = 1.25$ and the adjusted threshold value is 1.25. For this example, when C is used as the comparator, then $\log_{10}(R/C)$ equal or greater than 1.25 is considered the equivalent to a $\log_{10}(R/M)$ equal to or greater than 0.25 when M is used as the comparator. It will be readily apparent that an adjusted threshold value can be calculated in a similar manner for any additional comparator based on its relative strength to either MALAT1 or any other comparator for which an adjusted threshold value has already been determined.

The same adjustments above can be made when linear values compared to M are used as threshold levels (e.g., ≥1.75-fold, ≥2.0-fold, ≥2.25-fold, or 2.5-fold). In this case, one obtains the ratio of M to C, and then multiplies the threshold value by that ratio to obtain appropriate threshold values when comparing R to C (i.e., (threshold value)$_C$=(M/C)(threshold value)$_M$)

It should be understood that the specific chromosomal location of both RARA and MALAT1 may differ for different genome builds and/or for different cell types. However, one of skill in the art can determine such different locations by locating in such other genome builds, specific sequences corresponding to the RARA and/or MALAT1 loci in genome build hg 19.

Other methods for identifying super enhancers include chromatin immunoprecipitation (JE Delmore, et al., Cell, 146(6)904-917, 2011) and chip array (ChIP-chip), and chromatin immunoprecipitation followed by qPCR (ChIP-qPCR) using the same immunoprecipitated genomic markers and oligonucleotide sequences that hybridize to the chr17:38458152-38516681 (genome build hg19) RARA locus. In the case of ChIP-chip, the signal is typically detected by intensity fluorescence resulting from hybridization of a probe and input assay sample as with other array based technologies. For ChIP-qPCR, a dye that becomes fluorescent only after intercalating the double stranded DNA generated in the PCR reaction is used to measure amplification of the template.

In some embodiments, determination of whether a cell has a RARA super enhancer above a requisite threshold level is achieved by comparing RARA enhancer strength in a test cell to the corresponding RARA strength in a cell known to not respond to RARA (a "control cell"). Preferably the control cell is the same cell type as the test cell. In one aspect of these embodiments, the control cell is such cell in a HCC1143. In another aspect of these embodiments, the control cell is any cell listed in FIGS. 3A-3M, wherein $\log_{10}$(RARA/MALAT1) less than 0.25, less than 0.2, less than 0.15, less than 0.1, or less than 0.

In some embodiments, a subject is determined to be responsive to a RARA agonist if the strength of a RARA super enhancer in a cell in the subject is at least 1.5-fold greater than the strength of a corresponding RARA enhancer/super enhancer in a control cell. In some aspects of these embodiments, the threshold level is at least a 2.0 fold greater, at least a 2.5 fold greater, at least a 3 fold greater, at least a 4 fold greater, or at least a 5 fold greater strength than in the control cell. In some aspects of these embodiments, the strength of a RARA super enhancer in both the test cell and the control cell are normalized before comparison. Normalization involves adjusting the determined strength of a RARA super-enhancer by comparison to either another enhancer or super enhancer that is native to and present at equivalent levels in both of the cells (e.g., MALAT1), or to a fixed level of exogenous DNA that is "spiked" into samples of each of the cells prior to super-enhancer strength determination (DA Orlando et al., Cell Rep. 2014 Nov. 6, 9(3): 1163-70 (2014); N Bonhoure et al., Genome Res, 24:1157-68 (2014)).

In some embodiments, determination of whether a cell has a RARA super enhancer strength above a requisite threshold level is achieved by comparing RARA enhancer strength in a test cell to the corresponding RARA strength in a population of cell samples, wherein each of the cell samples is obtained from a different source (i.e., a different subject, a different cell line, a different xenograft). In some aspects of these embodiments, only primary tumor cell samples from subjects are used to determine the threshold level. In some aspects of these embodiments, at least some of the samples in the population will have been tested for responsiveness to a specific RARA agonist in order to establish: a) the lowest RARA enhancer strength of a sample in the population that responds to that specific RARA agonist ("lowest responder"); and, optionally, b) the highest RARA enhancer strength of a sample in the population that does not respond to that specific RARA agonist ("highest non-responder"). In these embodiments, a cutoff of RARA enhancer strength above which a test cell would be considered responsive to that specific RARA agonist is set: i) equal to or up to 5% above the RARA enhancer strength in the lowest responder in the population; or ii) equal to or up to 5% above the RARA enhancer strength in the highest non-responder in the population; or iii) a value in between the RARA enhancer strength of the lowest responder and the highest non-responder in the population.

It should be understood that in the above embodiments typically not all of the samples in a population need to be tested for responsiveness to the RARA agonist, but all samples are measured for RARA enhancer strength. In some embodiments, the samples are rank ordered based on RARA enhancer strength. The choice of which of the three methods set forth above to use to establish the cutoff will depend upon the difference in RARA enhancer strength between the lowest responder and the highest non-responder in the population and whether the goal is to minimize the number of false positives or to minimize the chance of missing a potentially responsive sample or subject. When the difference between the lowest responder and highest non-responder is large (e.g., when there are many samples not tested for responsiveness that fall between the lowest responder and the highest non-responder in a rank ordering of RARA enhancer strength), the cutoff is typically set equal to or up to 5% above the RARA enhancer strength in the lowest responder in the population. This cutoff maximizes the number of potential responders. When this difference is small (e.g., when there are few or no samples untested for responsiveness that fall between the lowest responder and the highest non-responder in a rank ordering of RARA enhancer strength), the cutoff is typically set to a value in between the RARA enhancer strength of the lowest responder and the highest non-responder. This cutoff minimizes the number of false positives. When the highest non-responder has a RARA enhancer strength that is greater than the lowest responder, the cutoff is typically set to a value equal to or up to 5% above the RARA enhancer strength in the highest non-responder in the population. This method also minimizes the number of false positives.

In some embodiments, determination of whether a cell has a RARA super enhancer above a requisite threshold level is achieved by comparing the ordinal of RARA enhancer strength in a test cell to the ordinal of RARA enhancer strength in a population of cell samples, wherein each of the cell samples is obtained from a different source (i.e., a different subject, a different cell line, a different xenograft). In these embodiments, at least some of the samples in the population will have been tested for responsiveness to a specific RARA agonist in order to establish: a) the lowest RARA enhancer strength ordinal of a sample in the population that responds to that specific RARA agonist ("lowest ordinal responder"); and, optionally, b) the highest RARA enhancer strength ordinal of a sample in the population that does not respond to that specific RARA agonist ("highest ordinal non-responder"). In these embodiments, a cutoff of RARA enhancer strength ordinal above which a test cell would be considered responsive to that specific RARA agonist is set: i) equal to or up to 5% above the RARA enhancer strength ordinal in the lowest ordinal responder in the population; or ii) equal to or up to 5% above the RARA enhancer strength ordinal in the highest ordinal non-responder in the population; or iii) a value in between the RARA enhancer strength ordinal of the lowest ordinal responder and the highest ordinal non-responder in the population.

It should be understood in the above embodiments, that typically not all of the samples in a population need to be tested for responsiveness to the RARA agonist, but all samples are measured for RARA enhancer strength and the ordinal of RARA enhancer strength compared to other enhancers in the same sample is established. The ordinal is typically obtained by measuring the strength of all other enhancers in the cell and determining what rank (i.e., the ordinal) in terms of strength the RARA enhancer has as compared to the other enhancers.

In some embodiments, the samples are rank ordered based on the ordinal of RARA enhancer strength. The choice of which of the three methods set forth above to use to establish the cutoff will depend upon the difference in ordinal of RARA enhancer strength between the lowest ordinal responder and the highest ordinal non-responder in the population and whether the cutoff is designed to minimize false positives or maximize the number of responders. When this difference is large (e.g., when there are many samples not tested for responsiveness that fall between the lowest ordinal responder and the highest ordinal non-responder in a rank ordering of ordinals of RARA enhancer strength), the cutoff is typically set equal to or up to 5% above the ordinal of RARA enhancer strength in the lowest ordinal responder in the population. When this difference is small (e.g., when there are few or no samples untested for responsiveness that fall between the lowest ordinal responder and the highest ordinal non-responder in a rank ordering of ordinal of RARA enhancer strength), the cutoff is typically set to a value in between the ordinal of RARA enhancer strength of the lowest ordinal responder and the highest ordinal non-responder. When the highest ordinal non-responder has an ordinal of RARA enhancer strength that is greater than that of the lowest responder, the cutoff is typically set to a value equal to or up to 5% above the ordinal of RARA enhancer strength in the highest ordinal non-responder in the population.

In some aspects of embodiments where a test cell or sample is compared to a population, the cutoff value(s) obtained for the population (e.g., RARA enhancer strength or RARA enhancer ordinal) is converted to a prevalence rank and the cutoff is expressed as a percent of the population having the cutoff value or higher, i.e., a prevalence cutoff. Without being bound by theory, applicants believe that the prevalence rank of a test sample will be similar regardless of the methodology used to determine RARA enhancer strength. Thus, a prevalence cutoff determined for one parameter (e.g., RARA enhancer strength ordinal) is portable and can be applied to another parameter (e.g., RARA mRNA level) to determine the cutoff value for that other parameter. This allows the determination of a cutoff value for any parameter without having to experimentally determine the correlation between levels of such parameter and responsiveness to the RARA agonist. All that needs to be determined is what level of such other parameter corresponds to the prior determined prevalence cutoff in a population.

RARA mRNA Level Determination

Our identification of the RARA super enhancer locus allows one to use RNA transcripts to determine sensitivity instead of super-enhancer level to determine sensitivity to a RARA agonist. RNA transcripts from the super-enhancer locus itself may be quantified and correlate very well with super-enhancer levels at that locus. We have also shown that mRNA transcripts encoding RARA also correlate with sensitivity to RARA agonists, and thus mRNA levels can be used to identify cells that will respond to RARA agonists.

In some embodiments, the RNA transcript level from the super-enhancer locus is quantified using quantitative techniques that compare RARA enhancer RNA transcript levels in a sample with corresponding RARA enhancer RNA transcript levels in a cell or cell line known to be non-responsive to a RARA agonist. Such methods include RNA array or sequencing based methods for reading the eRNA associated with enhancer read through (N Hah et al., PNAS, 112(3):E297-302, 2015), as well as RNA qPCR.

In some aspects of these embodiments, at least a 1.5 fold higher RARA RNA transcript level as compared to that of a corresponding RARA enhancer RNA transcript level in a cell or cell line known to be non-responsive to a RARA agonist is used as a threshold to identify sensitivity to a RARA agonist. In other aspects of these embodiments, the threshold for identifying RARA agonist responders is at least a 2.0 fold higher, at least a 2.5 fold higher, at least a 3 fold higher, at least a 4 fold higher, or at least a 5 fold higher RARA RNA transcript level as compared to that in the control cell.

In some embodiments, the mRNA levels of RARA are used to identify RARA agonist responders. In one aspect of these embodiments, mRNA levels are quantified using RNA-Seq or RNA-qPCR techniques. In each of these techniques the RARA mRNA level is determined in a test cell and compared to the RARA mRNA is a cell that is known to be non-responsive to a RARA agonist (the "control cell"), e.g., HCC1143 cells. In one aspect of these embodiments, an at least 1.5 fold higher RARA mRNA level in the test cell as compared to the control cell indicates responsiveness to RARA agonist (i.e., the pre-determined threshold value is at least 1.5-fold higher compared to the control cell). In other aspects of these embodiments an at least 2 fold, an at least 2.5 fold, an at least 3 fold, an at least 4 fold or an at least 5 fold higher RARA mRNA level in the test cell as compared to the control cell indicates responsiveness to RARA agonist. In another aspect of these embodiments, the control cell is any cell listed in FIGS. 3A-3M, wherein $\log_{10}$(RARA/MALAT1) less than 0.25, less than 0.2, less than 0.15, less than 0.1, or less than 0.

In alternate embodiments, the RARA mRNA levels in a subject (i.e., in a tumor sample, in a cancer cell sample, in a blood sample, etc.) are compared, using the same assay, to the RARA mRNA levels in a population of subjects having the same disease or condition to identify RARA agonist responders. In these embodiments, at least some of the samples in the population will have been tested for responsiveness to a specific RARA agonist in order to establish: a) the lowest RARA mRNA level of a sample in the population that responds to that specific RARA agonist ("lowest mRNA responder"); and, optionally, b) the highest RARA mRNA level of a sample in the population that does not respond to that specific RARA agonist ("highest mRNA non-responder"). In these embodiments, a cutoff of RARA mRNA level above which a test cell would be considered responsive to that specific RARA agonist is set: i) equal to or up to 5% above the RARA mRNA level in the lowest mRNA responder in the population; or ii) equal to or up to 5% above the RARA mRNA level in the highest mRNA non-responder in the population; or iii) a value in between the RARA mRNA level of the lowest mRNA responder and the highest mRNA non-responder in the population.

In some embodiments not all of the samples in a population need to be tested for responsiveness to the RARA agonist, but all samples are measured for RARA mRNA levels. In some embodiments, the samples are rank ordered based on RARA mRNA levels. The choice of which of the three methods set forth above to use to establish the cutoff will depend upon the difference in RARA mRNA levels between the lowest mRNA responder and the highest mRNA non-responder in the population and whether the cutoff is designed to minimize false positives or maximize the potential number of responders. When this difference is large (e.g., when there are many samples not tested for responsiveness that fall between the lowest mRNA responder and the highest mRNA non-responder in a rank ordering of RARA mRNA levels), the cutoff is typically set equal to or up to 5% above the RARA mRNA level in the lowest mRNA responder in the population. When this difference is small (e.g., when there are few or no samples untested for responsiveness that fall between the lowest mRNA responder and the highest mRNA non-responder in a rank ordering of RARA mRNA levels), the cutoff is typically set to a value in between the RARA mRNA levels of the lowest mRNA responder and the highest mRNA non-responder. When the highest mRNA non-responder has a RARA mRNA levels that is greater than the lowest mRNA responder, the cutoff is typically set to a value equal to or up to 5% above the RARA mRNA levels in the highest mRNA non-responder in the population.

In some embodiments the population is rank ordered based on RARA mRNA level. In these embodiments, the RARA mRNA level in each sample is measured and compared to the mRNA levels of all other mRNAs in the cell to obtain an ordinal ranking of the RARA mRNA level. A cutoff based on RARA mRNA ordinal ranking is then determined based on samples in the population tested for responsiveness to a RARA agonist in the same manner as described previously for determining a RARA super enhancer strength ordinal cutoff. The determined RARA mRNA ordinal cutoff is then used either directly or to determine a prevalence cutoff, either of which is then used to stratify additional samples for potential responsiveness to the RARA agonist.

In some embodiments, the cutoff for RARA mRNA levels is determined using the prevalence cutoff established based on RARA enhancer strength or RARA enhancer strength ordinal, as described above. In some aspects of these embodiments, a population is measured for mRNA levels and the prior determined prevalence cutoff is applied to that population to determine a mRNA cutoff level. In some aspects of these embodiments a rank-order standard curve of RARA mRNA levels in a population is created, and the pre-determined prevalence cutoff is applied to that standard curve to determine the RARA mRNA cutoff level.

In some aspects of embodiments where a test cell or sample is compared to a population, the cutoff mRNA level value(s) obtained for the population is converted to a prevalence rank and the mRNA level cutoff is expressed as a percent of the population having the cutoff value or higher, i.e., a prevalence cutoff.

Without being bound by theory, applicants believe that the prevalence rank of a test sample and the prevalence cutoff in a population will be similar regardless of the methodology used to determine RARA mRNA levels.

In some aspects of these embodiments, a subject is identified as a RARA agonist responder if its RARA mRNA level corresponds to a prevalence rank in a population of 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 43%, 42%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, or 20% as determined by RARA mRNA levels in the population. In one aspect of these embodiments, the cutoff value is established based on the prevalence cutoff established for RARA enhancer strength. In an alternate aspect of these embodiments, the cutoff value is established based on the prevalence cutoff established for RARA enhancer strength ordinal. In another alternate aspect of these embodiments, the cutoff value is established based on RARA mRNA levels. In more specific aspects of these embodiments, a cutoff value for breast cancer patients is established based on the prevalence cutoff determined for RARA enhancer strength ordinal, and that prevalence cutoff value is used as to determine the cutoff value for RARA mRNA levels In even more specific aspects of these embodiments, the cutoff value for breast cancer patients is the value determined using a prevalence value of between 50% and 60%, e.g., 50-55%, 55-60%, 50-56%, 50-57%, 51-55%, 51-56%, 51-57%, 52-55%, 52-56%, 52-57%, 53-55%, 54-56%, 53-56%, or 54-55%. In still other more specific aspects of these embodiments, the cutoff value is set using a prevalence value of 55% or of 56%. In other more specific aspects of these embodiments, a cutoff value for AML patients is established based on the prevalence value determined for RARA enhancer strength ordinal, and that prevalence value is used to determine the cutoff value for RARA mRNA levels In even more specific aspects of these embodiments, the cutoff value for AML patients is determined using a prevalence cutoff of between 25-45%, e.g., between 25-30%, 25-35%, 25-40%, 30-35%, 30-40%, 35-45%, 35-40%, 31-35%, 32-35%, 33-35%, 34-35%, 31-36%, 32-36%, 33-36%, 34-36%, or 35-36%. In other even more specific aspects of these embodiments, the cutoff value for AML patients is determined using a prevalence value of 36%. In yet other even more specific aspects of these embodiments, the cutoff value for AML patients is determined using a prevalence value of 25%.

In still other embodiments, a population may be divided into three groups—responders, partial responders and non-responders and two cutoff values or prevalence cutoffs are set. The partial responder group may include responders and non-responders, as well as those population members whose response to a RARA agonist was not as high as the responder group. In these embodiments, two cutoff values or prevalence cutoffs are determined. This type of stratification may be particularly useful when in a population the highest RARA mRNA non-responder has a RARA mRNA levels that is greater than the lowest RARA mRNA responder. In this scenario the cutoff level or prevalence cutoff between responders and partial responders is set equal to or up to 5% above the RARA mRNA level of the highest RARA mRNA non-responder; and the cutoff level or prevalence cutoff between partial responders and non-responders is set equal to or up to 5% below the RARA mRNA level of the lowest RARA mRNA responder. The determination of whether partial responders should be administered the RARA agonist will depend upon the judgment of the treating physician and/or approval by a regulatory agency.

Methods of quantifying specific RNA sequences in a cell or biological sample are known in the art and include, but are not limited to, fluorescent hybridization such as utilized in services and products provided by NanoString Technologies, array based technology (Affymetrix), reverse transcriptase qPCR as with SYBR® Green (Life Technologies) or TaqMan® technology (Life Technologies), RNA sequencing (e.g., RNA-seq), RNA hybridization and signal amplification as utilized with RNAscope® (Advanced Cell Diagnostics), or northern blot.

In some aspects of these embodiments, the level of RNA transcript (either mRNA or another RARA transcript) in both the test cell and the control cell or all members of the population are normalized before comparison. Normalization involves adjusting the determined level of a RARA RNA transcript by comparison to either another RNA transcript that is native to and present at equivalent levels in both of the cells (e.g., GADPH mRNA, 18S RNA), or to a fixed level of exogenous RNA that is "spiked" into samples of each of the cells prior to super-enhancer strength determination (J Loven et al., Cell, 151(3):476-82 (2012); J Kanno et al., BMC Genomics 7:64 (2006); J Van de Peppel et al., EMBO Rep 4:387-93 (2003)).

Cancers and Other Diseases

The methods and packaged pharmaceuticals of the present invention are theoretically useful to treat any cancer that is characterized by the association of a super enhancer with a RARA gene in such cancer. Super enhancer-associated RARA genes may be more prevalent in certain types of cancers than others. The inventors have discovered RARA associated super enhancers in cancers of the skin, breast, blood, bone, cervix, colon, rectum, esophagus, lymph node, lung, ovary, uterus, pancreas, prostate, kidney, and spleen; and in particular in AML (especially in non-APL AML and in other forms of AML that are not characterized by a chromosomal translocation involving a RARA gene), myelodysplastic syndrome (MDS), colorectal, HER2+ breast, ER+ breast, triple-negative breast cancer, glioblastoma, glioma, gastric cancer, renal clear cell carcinoma, non-small cell lung cancer, melanoma, multiple myeloma, pancreatic carcinoma, pheochromocytoma, paraganglioma, and prostate adenocarcinoma. Without being bound by theory, the inventors believe that SE-associated RARA genes will be found in subsets of all cancers and that subjects within those subsets will be more responsive to a RARA agonist than other subjects having the same type of cancer without a SE-associated RARA gene.

We also believe that the discovery of SE-associated RARA in tissues in non-cancer disease suggests potential for the effective use of RARA agonists to treat such diseases. We have detected the presence of the RARA super enhancer in adipose tissue suggesting a method of identifying patients suffering from diabetes or obesity who may be effectively treated with a RARA agonist. Retinoic acid has an established role in the differentiation of adipose tissue (J Mercader, et al., Endocrinology, 147(100):5325-5332, 2006). In addition, a relationship between PPAR-γ and RARA has been shown (A Redonnet, et al., Int J Obesity, (26)920-927, 2002).

A super enhancer associated with the RARA locus has also been detected in numerous types of hematological cells. This includes $CD133^+$ hematopoietic stem cells, $CD14^+$ monocytes, $CD19^+$ early B-cells, CD20 B-cells, $CD3^+$ mature T-cells, $CD34^+$ hematopoietic progenitors, $CD4^+$ T helper cells, CD56 Natural Killer cells, and $CD8^+$ cytotoxic T cells. The presence of RARA associated super-enhancers in these cells suggest that RARA agonists may be useful to treat subsets of patients suffering from certain autoimmune diseases, including but not limited to psoriasis, multiple sclerosis, rheumatoid arthritis, ankylosing spondylitis, celiac disease, myasthenia gravis, systemic lupus erythematosus and scleroderma.

Cell from patients suffering from Autosomal Dominant Polycystic Kidney Disease also has been found to have a RARA associated super enhancer and thus could be candidates for effective treatment with RARA agonist. There is some evidence that ADPKD can respond to retinoids (Q Qian, et al., Kidney International, (59): 2005-2022, 2001), so identifying those patients who also have a SE associated with the RARA locus may be used as a stratification method to better select those patients who are more likely to respond to a RARA selective agonist.

In some embodiments, the disease to be treated in the methods and by the packaged pharmaceutical compositions of the invention is cancer. In some aspects of these embodiments, the disease to be treated is selected from breast cancer, glioblastoma, neuroblastoma and AML. In some more specific aspects of these embodiments, the disease to be treated is selected from breast cancer, glioma, cervical and endocervical carcinoma, colon and rectal adenocarcinoma, head and neck squamous carcinoma, kidney renal papillary cell carcinoma, lung adenocarcinoma, pancreatic adenocarcinoma, pheochromocytoma, paraganglioma, skin cutaneous melanoma, uterine carcinoma, MDS and AML. In some more specific aspects of these embodiments, the disease to be treated is selected from breast cancer, MDS and AML. In some more specific aspects of these embodiments, the disease to be treated is selected from breast cancer and AML. In even more specific aspects of these embodiments, the disease to be treated is non-APL AML or an AML that is not characterized by a chromosomal translocation involving a RARA gene.

In some embodiments, the subject to be treated with a RARA agonist (e.g., tamibarotene) is suffering from relapsed or refractory AML. A subject is classified as having relapsed or refractory AML if they: a) do not demonstrate a partial response after a first cycle of induction chemotherapy; or b) do not demonstrate a complete response after a second cycle of induction chemotherapy; or c) relapse after conventional chemotherapy; or d) relapse are undergoing a single stem cell transplantation.

In some embodiments, the subject to be treated with a RARA agonist (e.g., tamibarotene) is suffering from refractory MDS. A subject is classified as having refractory MDS if they: a) are categorized as having high risk or intermediate-2 MDS (as determined using the International Prognostic Staging System ("IPPS")) and have failed to achieve any hematologic improvement (as measured by IWG 2006 criteria) after at least 4 cycles of induction therapy with hypomethylating agents (e.g., azacitidine, decitabine), or has relapsed after any duration of complete or partial response; or b) are categorized as IPSS intermediate-1 or low-risk MDS and are either transfusion dependent or have failed treatment with erythropoiesis stimulating agents (ESA).

In other embodiments, the subject to be treated with a RARA agonist (e.g., tamibarotene) is an elderly unfit subject. The term "elderly unfit" as used herein means the subject is a human at least 60 years of age and who is determined by a physician to not be a candidate for standard induction therapy.

RARA Agonists

The choice of RARA agonist with which to treat a patient identified as having a super enhancer associated with a RARA gene may be made from any RARA agonist known in the art. It is preferable that the RARA agonist utilized in the methods of the invention be specific for RARA and have significantly less (at least 10× less, at least 100× less, at least 1,000× less, at least 10,000× less, at least 100,000× less) agonistic activity against other forms of RaR, e.g., RaR-8 and RaR-γ.

In some embodiments, the RARA agonist is selected from a compound disclosed in or any compound falling within the genera set forth in any one of the following United States patents: U.S. Pat. Nos. 4,703,110, 5,081,271, 5,089,509, 5,455,265, 5,759,785, 5,856,490, 5,965,606, 6,063,797, 6,071,924, 6,075,032, 6,187,950, 6,355,669, 6,358,995, and 6,387,950, each of which is incorporated by reference.

In some embodiments, the RARA agonist is selected from any of the following known RARA agonists set forth in Table 1, or a pharmaceutically acceptable salt thereof, or a solvate or hydrate of the foregoing:

TABLE 1
Exemplary RARA Agonists useful in the invention.
| Structure | Code Name(s) |
|---|---|
| 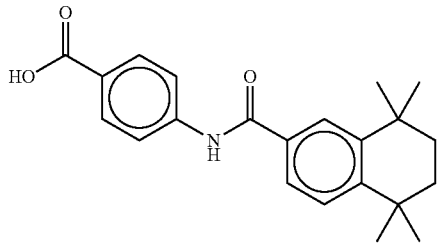 | Am-580; CD-336; Ro-40-6055 |
| 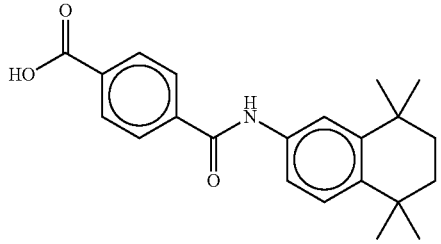 | AM-80; INNO-507; NSC-608000; OMS-0728; TM-411; TOS-80; TOS-80T; Z-208; tamibarotene |
| 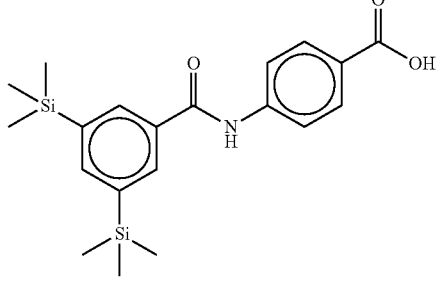 | Am-555S; TAC-101; amsilarotene |
| 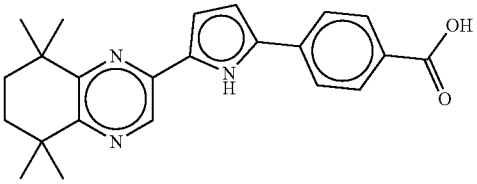 | ER-34617 |
| 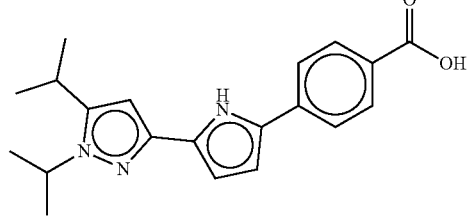 | ER-38930 |
| 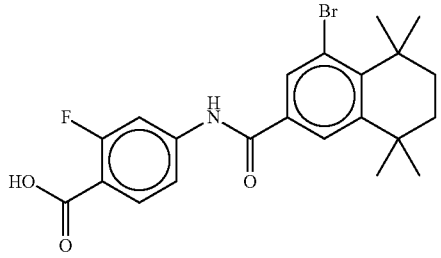 | |

TABLE 1-continued
Exemplary RARA Agonists useful in the invention.
| Structure | Code Name(s) |
|---|---|
| 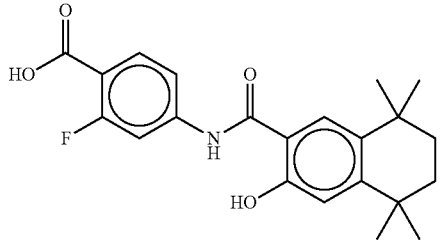 | |
| 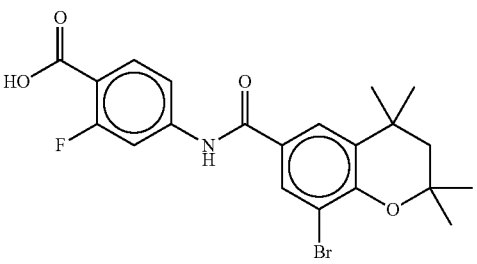 | |
| 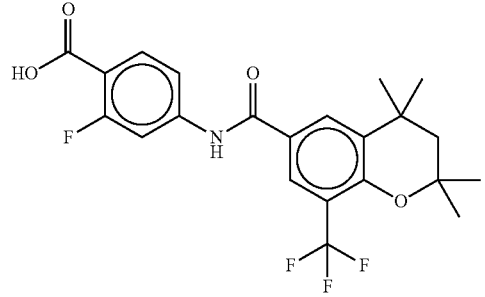 | |
| 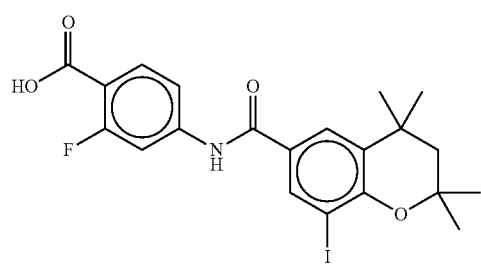 | |
| 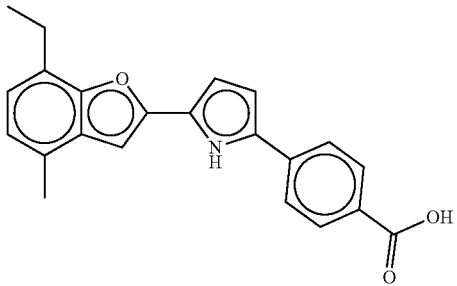 | ER-65250 |

TABLE 1-continued

Exemplary RARA Agonists useful in the invention.

| Structure | Code Name(s) |
|---|---|
| 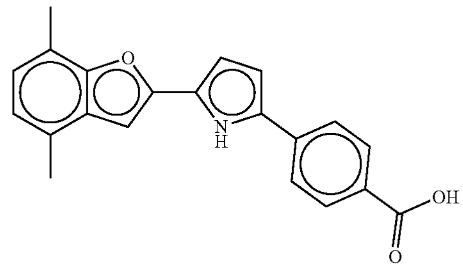 | ER-38925 |
| 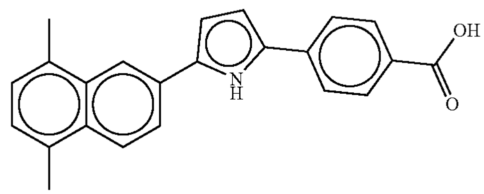 | ER-35368 |
| 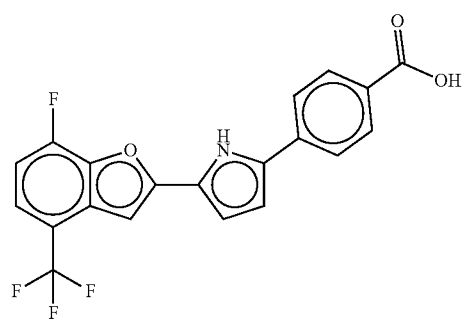 | E-6060 |
| 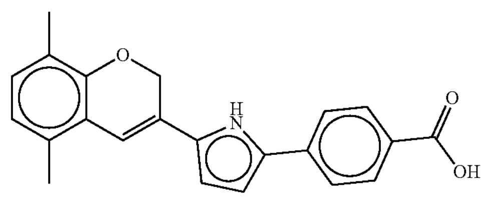 | ER-41666 |
|  | AGN-195183;<br>NRX-195183;<br>VTP-195183;<br>VTP-5183<br>IRX-5183 |
| 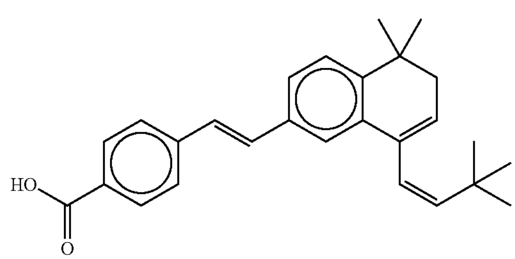 | BMS-228987 |

TABLE 1-continued

Exemplary RARA Agonists useful in the invention.

| Structure | Code Name(s) |
|---|---|
| 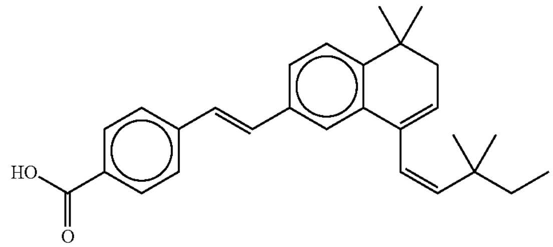 | BMS-276393 |
| 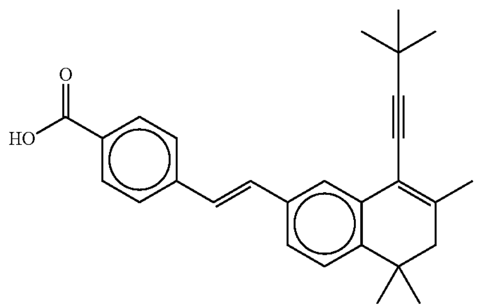 | BMS-231974 |
| 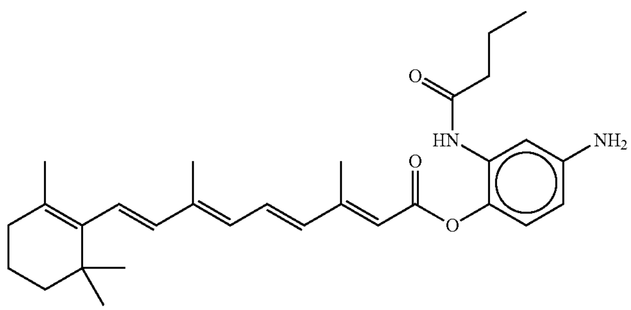 | ABPN; CBG-41 |
| 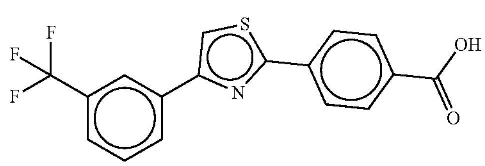 | PTB |
| | |
| | |

TABLE 1-continued

Exemplary RARA Agonists useful in the invention.

| Structure | Code Name(s) |
|---|---|

TABLE 1-continued

Exemplary RARA Agonists useful in the invention.

| Structure | Code Name(s) |
|---|---|

TABLE 1-continued

Exemplary RARA Agonists useful in the invention.

| Structure | Code Name(s) |
|---|---|
| | |
| | |
| | |
| 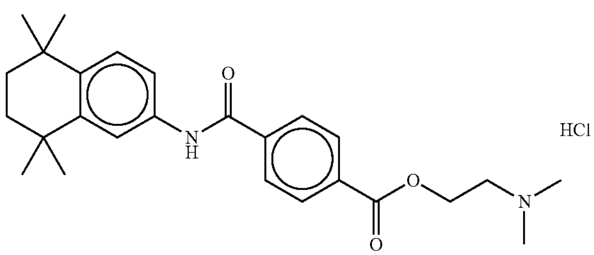 | A-112 |
| 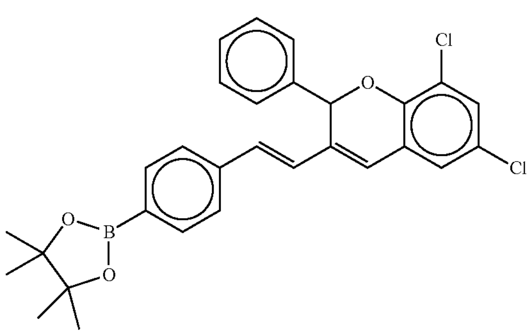 | BD-4; BJ-1 |

TABLE 1-continued

Exemplary RARA Agonists useful in the invention.

| Structure | Code Name(s) |
|---|---|
| 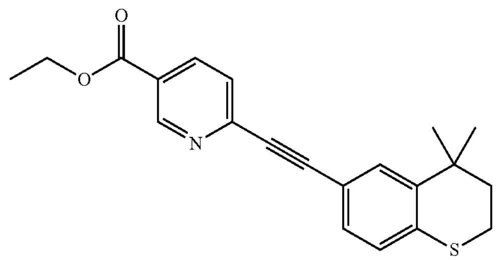 [SMILES: CCOC(=O)c1ccc(C#Cc2ccc3c(c2)C(C)(C)CCS3)nc1] | Tazarotene; AGN-190168 |
| 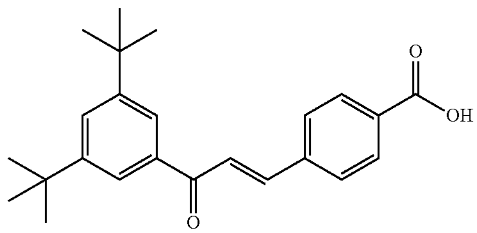 [SMILES: CC(C)(C)c1cc(C(=O)/C=C/c2ccc(C(=O)O)cc2)cc(C(C)(C)C)c1] | Ch-55 |

Packaged Pharmaceutical Compositions

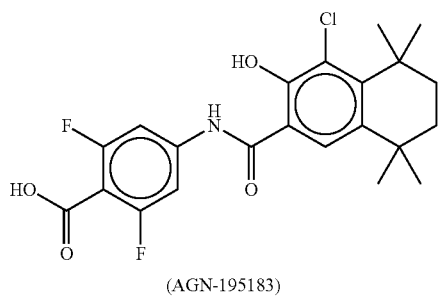

(AGN-195183)

The packaged pharmaceutical compositions of the present invention comprise a written insert or label comprising instructions to use the RARA agonist in a subject suffering from a cancer and who has been determined to have a super enhancer associated with a RARA gene having a strength, or ordinal rank equal to or above a threshold level, or a RARA mRNA level equal to or above a threshold level. As described in detail above, the threshold level is determined in a population of samples from either subjects diagnosed as suffering from the same disease or cell lines or xenograft models of the same disease as that for which the pharmaceutical composition is indicated for treatment. The instructions may be adhered or otherwise attached to a vessel comprising the RARA agonist. Alternatively, the instructions and the vessel comprising the RARA agonist will be separate from one another, but present together in a single package, box or other type of container.

The instructions in the packaged pharmaceutical composition will typically be mandated or recommended by a governmental agency approving the therapeutic use of the RARA agonist. The instructions may comprise specific methods of determining whether a super enhancer is associated with a RARA gene, as well as quantification methods to determine whether an enhancer associated with a RARA gene is a super enhancer, quantification methods to determine RARA mRNA levels; and/or threshold levels of super enhancers or RARA mRNA at which treatment with the packaged RARA agonist is recommended and/or assumed therapeutically effective. In some aspects, the instructions direct that the composition be administered to a subject whose RARA mRNA level falls in at least the $30^{th}$ percentile of a population whose RARA mRNA levels have been measured. In some aspects of these embodiments, a subject is identified as a RARA agonist responder if its RARA mRNA level prevalence rank is 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 43%, 42%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, or 20% in a population whose RARA mRNA levels have been measured. In some aspects, the instructions direct that the composition be administered to a subject whose RARA mRNA level as measured by a specific assay The instructions may optionally comprise dosing information, the types of cancer for which treatment with the RARA agonist was approved, physicochemical information about the RARA agonist; pharmacokinetic information about the RARA agonist, drug-drug interaction information. In some aspects, the instructions direct that the composition be administered to a subject diagnosed as suffering from non-APL AML. In other aspects, the instructions direct that the composition be administered to a subject diagnosed as suffering from breast cancer. In some aspects, the instructions direct that the composition be administered to a subject diagnosed as suffering from MDS. In some aspects, the pharmaceutical composition comprises tamibarotene. In some aspects, the pharmaceutical composition comprises AGN-195183.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. ChIP-seq Analysis to Identify RARA Associated Super Enhancer

I. Cross-Linking of Cells.

For cultured cells, we typically cross-link between $5 \times 10^7$ and $1 \times 10^8$ cells at a time (equivalent to 70-80% confluency for adherent cells in 8-12 15 $cm^2$ plates or suspension cells in 8-12 175 $cm^2$ flasks). We use 20-50 million cells for each location analysis reaction. For adherent cells, we add 1/10 volume of fresh 11% formaldehyde solution (0.1M NaCl, 1 mM EDTA, pH 8, 0.5 mM EGTA pH 8, 50 mM Hepes) to plates, swirl the plates briefly and let them sit at room temperature ("RT") for 8 min. We then add 1/20 volume of 2.5M glycine or 1/2 volume of 1M Tris pH 7.5 to quench formaldehyde and incubate for at least 1 min. We then rinse the cells 3× with 20 ml cold 1× phosphate-buffered saline ("PBS"); harvest the cells using silicon scraper; and spin the cells at 2 k for 10 minutes at 4° C. in tabletop centrifuge. Cells are then transferred to 15 ml conical tubes and spun at 2 k for 10 minutes at 4° C. The pelleted cells are flash frozen in liquid nitrogen and stored at −80° C.

For cells in suspension we add 1/10 volume of fresh 11% formaldehyde solution to cell suspension, mix and let the mixture sit at RT for 8 min. We then add 1/20 volume of 2.5M glycine or 1/2 volume of 1M Tris pH 7.5 to quench formaldehyde and incubate for at least 1 min. We then rinse the cells 3× with 20-50 ml cold 1×PBS, centrifuging for 5 min at 2,000 RPM to pellet the cells before and after each wash. Cells are then transferred to 15 ml conical tubes and spun at 2 k for 5 minutes at 4° C. The supernatant is removed, residual liquid is removed by dabbing with a Kimwipe and then the pelleted cells are flash frozen in liquid nitrogen and stored at −80° C.

For cells derived from primary blood, we cross-link between $2 \times 10^5$ and $1 \times 10^7$ cells per sample by addition of 1/10 volume of fresh 11% formaldehyde solution (0.1M NaCl, 1 mM EDTA, pH 8, 0.5 mM EGTA pH 8, 50 mM Hepes), cross linking is allowed to proceed at RT for 8 min. We then add 1/20 volume of 2.5M glycine or 1/2 volume of 1M Tris pH 7.5 to quench formaldehyde and incubate for at least 1 min. We then rinse the cells 3× with 1-2 ml cold 1×PBS; and harvest the cells by centrifugation. Cell pellets are then directly subjected to ChIP-seq analysis as described.

For cells derived from primary solid tissue, we use 250-500 ug of frozen tissue per ChIP. Frozen tissues are diced with razor blade (on cold surface, <−80 C) and scissors for 2 min in 1% Formaldehyde solution (1% Formaldehyde; 0.1M NaCl, 1 mM EDTA, pH 8, 0.5 mM EGTA pH 8, 50 mM Hepes). Tissues are chopped to a fine slurry for 2 min and to the slurry is added 9 ml of 1% formaldehyde solution. Crosslinking is allowed to proceed to a total time of 8 min. We then add 1/20 volume of 2.5M glycine or 1/2 volume of 1M Tris pH 7.5 to quench formaldehyde and incubate for at least 1 min. We then rinse the cells 3× with 1-2 ml cold 1×PBS; and harvest the cells by centrifugation. Cells are resuspended in 6 ml PBS (Containing Complete™ protease inhibitors) and dounce homogenized ~40× with loose pestle homogenizer. Cells are recovered by centrifugation at 3,000 RPM for 2 min. Supernatant is removed and pelleted cells flash frozen in liquid nitrogen for ChIP-seq analysis as described.

II. Binding of Antibody to Magnetic Beads.

We use 60 μL of Dynabeads® Protein G per 2 ml immunoprecipitate (Invitrogen). Beads are washed 3 times for 5 minutes each with 1.0 ml blocking buffer (0.5% BSA w/v in PBS) in a 1.5 ml Eppendorf tube. A magnet (Invitrogen) is used to collect the beads (we allow magnet binding for at least 1 full minute) after each wash and the supernatant is then aspirated. The washed beads are resuspended in 250 ul blocking buffer to which 6 μg of antibody is added and the mixture is allowed to incubate with end-over-end mixing overnight (minimum 6 hours). The antibody-bound-beads are washed 3× for 5 min each with 1 ml blocking buffer and resuspended in blocking buffer (60 ul per IP). These last washes and resuspensions are done once the cells have been sonicated (see next step) and just prior to overnight immunoprecipitation.

III. Cell Prep and Genomic Fragmentation.

We add 1× protease inhibitors (Complete, Roche; prepare by dissolving one tablet in 1 ml $H_2O$ for 50× solution and store in aliquots at −20° C.) to all lysis buffers before use. Each tube of cells (approximately $5 \times 10^7$ cells) is resuspended in 5-10 ml of lysis buffer 1 (LB1; 140 mM NaCl, 1 mM EDTA, 10% glycerol, 0.5% NP-40, 0.25% Triton X-100) and rocked at 4° C. for 10 minutes. The cells are centrifuged at 2,000 RPM×5 min in tabletop centrifuge at 4° C. and the supernatant aspirated off. The cells are resuspended in 5 ml Lysis Buffer 2 (LB2; 200 mM NaCl, 1 mM EDTA, 0.5 mM EGTA, 10 mM Tris pH 8) and incubated end over end at 4° C. for 10 minutes. The cells are again pelleted at 2,000 RPM×5 min in tabletop centrifuge at 4° C. and washed in 2-5 ml Covaris sonication buffer (10 mM Tris pH 8.0, 1 mM EDTA, 0.1% SDS). Pellets are spun down at 2,000 RPM×5 min in tabletop centrifuge at 4° C. The cells are pelleted at 2,000 RPM×5 min in tabletop centrifuge at 4° C. and resuspended at a concentration of 20-50 million cells/1 ml of Covaris sonication buffer.

One ml of cell lysate is put into 12×12 Covaris micro tubes and sonicated for 5 minutes total (Peak power 140, duty factor 5.0, cycles/burst 200). We recombine sonicates into one 15 ml tube, add 1 volume of 2× Dilution mix (300 mM NaCl, 2 mM EDTA, 50 mM Tris pH 8.0, 1.5% Triton-X, 0.1% SDS), pellet the insoluble fraction at 14,000 RPM for 10 min at 4° C. and collect the supernatant into a single tube. The supernatant is used as ChIP input for chromatin immunoprecipitations. We also collect 50 μL of the cell lysate for whole cell extract ("INPUT") sample control.

IV. Chromatin Immunoprecipitation.

Fifty L of antibody-conjugated beads from step II is added to cleared cellular extract (Prepared in Step III) solution in 1.5 ml tubes and rocked overnight at 4° C. (minimum 8 hours) to immunoprecipitate DNA-protein complexes.

V. Wash, Elution, and Cross-Link Reversal.

All buffers used in these steps are ice cold. We use a magnetic stand to precipitate magnetic beads, washed 3 times 5 minutes each with gentle end over end mixing with 1 ml Wash Buffer 1 (50 mM HEPES pH 7.5; 140 mM NaCl; 1 mM EDTA; 1 mM EGTA; 0.75% Triton-X; 0.1% SDS; 0.05% DOC); wash once for 5 minutes with 1 ml Wash Buffer 2 (50 mM HEPES pH 7.5; 500 mM NaCl; 1 mM EDTA; 1 mM EGTA; 0.75% Triton-X; 0.1% SDS; 0.05% DOC); and once for 5 minutes with 1 ml Wash Buffer 3 (10 mM Tris pH 8.0; 1 mM EDTA; 50 mM NaCl). We aspirate all residual wash buffer, spin the beads gently at 2,000 RPM for 1 min; put tubes back onto the magnet and remove all traces of buffer. We then add 210 μl of Elution buffer (50 mM Tris pH8; 10 mM EDTA; 1% SDS) and elute at 65° C.

for 60 min with brief vortexing to resuspend beads every 15 min. We separate the beads from the supernatant using the magnet; remove 200 μL of supernatant and place in a clean tube for reverse cross-linking. We reverse x-link both IP and whole cell extract fractions overnight at 65° C. (minimum 8 hours, but maximum 18 hours). We then use heating to separately reverse cross-linked both the sample for immunoprecipitation and the whole cell extract fractions by incubating overnight at 65° C. (minimum 8 hours, but maximum 18 hours). The heating facilitates the hydrolysis of the formaldehyde cross-links.

V. Cleanup and Purification of DNA.

We add 200 μl of TE (50 mM Tris pH8; 1 mM EDTA) and 2.7 μl of 30 mg/ml RNaseA (0.2 mg/ml final concentration) to each sample, mixed and incubate at 37° C. for 2 hours. We then add 5 μl of calcium chloride solution (300 mM $CaCl_2$ in 10 mM Tris pH8.0) to each sample along with 4 μL of 20 mg/ml proteinase K (0.2 mg/ml final concentration), mix and incubate at 55° C. for 60 minutes. We then add 400 μl of phenol:chloroform:isoamyl alcohol at 25:24:1 ratio (Sigma Aldrich # P3803) to each tube, mix on a vortex mixer on low setting (5/10) and invert each tube to mix further.

We prepare a PhaseLock Gel™ tube (Qiagen, 3 Prime) for each sample by spinning the tube at room temperature for 30 seconds at 10,000 RPM. We next add the sample DNA sample in phenol:chloroform:isoamyl alcohol to the PhaseLock Gel™ tube and spin at 12,000-16,000×g for 2 minutes at room temperature. We transfer the aqueous solution to a new 1.6 ml tube (top fraction), add 20 ul of 5M NaCl, and 1.5 ul of 20 ug/ul glycogen (30 ug total), then add 1 ml of EtOH and mix by vortex or inversions. The sample is then incubated at −20° C. overnight (6-16 hours). We then spin the mixture at 20,000×g for 20 minutes at 4° C. to pellet the DNA, remove the supernatant with 1 ml pipette tip, wash the pellets in 800 μl of 80% EtOH, spin at 20,000×g for 20 minutes at 4° C. and remove the supernatant with 1 ml pipette tip. We again spin the sample for 1 min at 20,000×g, remove all traces of the supernatant and let air dry for 5-20 minutes. The pellets should not have a halo of water around them and should be glassy or flaky dry. We then dissolve the pellet in 60 μl of water, using 10 μl for qPCR validation and 50 μl for sequencing. For ChIP-qPCR, amplification is performed using 1 uL of the sample per well with 0.8 uM of forward (F) and reverse (R) primers each mixed with 2× Power SYBR Green PCR Master Mix from Life Technologies following the manufacturer's protocol. Primers to use are as shown in the table below, where V1, V2, and V3 are primer pairs designed to hybridize to different regions within the RARA enhancer and "down" is a primer pair designed to hybridize to downstream non-acetylated, non-gene coding control region.

| V1 | | V3 | |
|---|---|---|---|
| F | AAACGTGTCCCCACCTCTC (SEQ ID NO: 1) | F | TTCCTAGTGGTCCCCCTTCC (SEQ ID NO: 5) |
| R | CCAGCCAGGCACATAGGG (SEQ ID NO: 2) | R | TGAAGATTGTTTGCACCCCT (SEQ ID NO: 6) |
| V2 | | down | |
| F | GTCACCGCACTCACTCCATT (SEQ ID NO: 3) | F | CTGCTGGTACCCAGAAGTGAG (SEQ ID NO: 7) |
| R | AAATAGCGCTCGGTGGAGAA (SEQ ID NO: 4) | R | TGTTGAGTTTTGCCAGTCTT (SEQ ID NO: 8) |

Figure 1A:
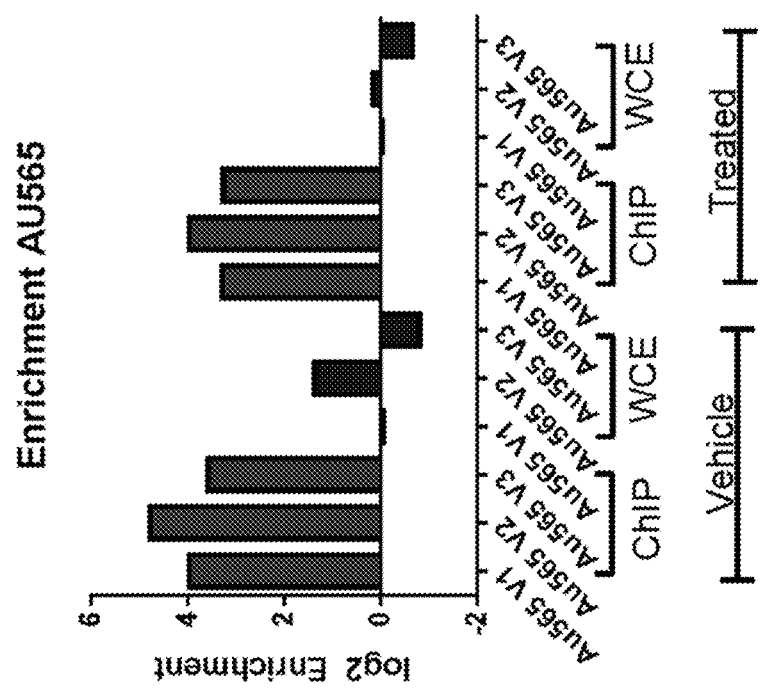

The results of ChIP-qpCR for a strongly responsive (Au565) and a weakly responsive ("T47D) cell line as compared to a whole cell extract ("WCE") from each cell is shown in FIGS. 1A-B. This figure illustrates that these primers are effective at measuring a strong enrichment for the H3K27ac mark at the enhancer for these cell lines in the pull down but not WCE after normalization to a nearby intergenic control region.

VII. ChIP Seq Analysis and Quantification of RARA Super Enhancer.

We use the above-described methodology using H3K27ac ChIP-seq to identify a super enhancer locus overlapping the RARA gene at chr17:38458152-38516681 (genome build hg19). This chromosome region was designated by consensus over the samples that are examined, but could vary somewhat based on which genomic marker is being detected or the type of tissue being used. To assess the strength of this super-enhancer locus across different samples we perform H3K27ac ChIP-seq in each sample and also sequence a match ChIP Input sample. All H3K27ac and input samples are aligned to the hg19 genome using Bowtie2 (using the -sensitive parameter). The gene track visualization shown in FIG. 2 demonstrates a representative sample of cells showing the counts of aligned reads in 1 bp bins, where each read is extended 200 bp in the direction of the alignment. Read counts are in number of aligned reads-per-million aligned reads (RPM). AUC is calculated by summing the reads at each base pair within a defined locus. Based on the location of the RARA super enhancer locus, we also assessed the level of RARA super enhancer relative to the MALAT1 super enhancer locus in existing H3K27ac ChIP-seq maps from various cell lines and patient samples.

For each H3K27Ac/Input sample pair (rows in the table in FIGS. 3A-3M), the number of H3K27Ac or Input reads aligning to either the RARA super-enhancer (chr17: 38458152-38516681) or the positive control super-enhancer at MALAT1 (chr11:65263724-65266724) are counted. All read counts are in RPM. We then subtract the Input signal from the H3K27Ac signal at both loci to get the enrichment of H3K27ac ChIP-seq reads over background (DIFF column). Finally, to assess the strength of the RARA super-enhancer relative to the MALAT1 positive control super-enhancer, we calculate the ratio of the RARA super-enhancer H3K27Ac enrichment signal to the H3K27Ac enrichment signal at the MALAT1 super-enhancer and report this ratio in the RARA/MALAT1 column. A higher value indicated a stronger RARA super-enhancer score. We also calculate the $\log_{10}$(RARA/MALAT1) ratio. All of these values for each sample tested are shown in FIGS. 3A-3M.

Figure 4B:
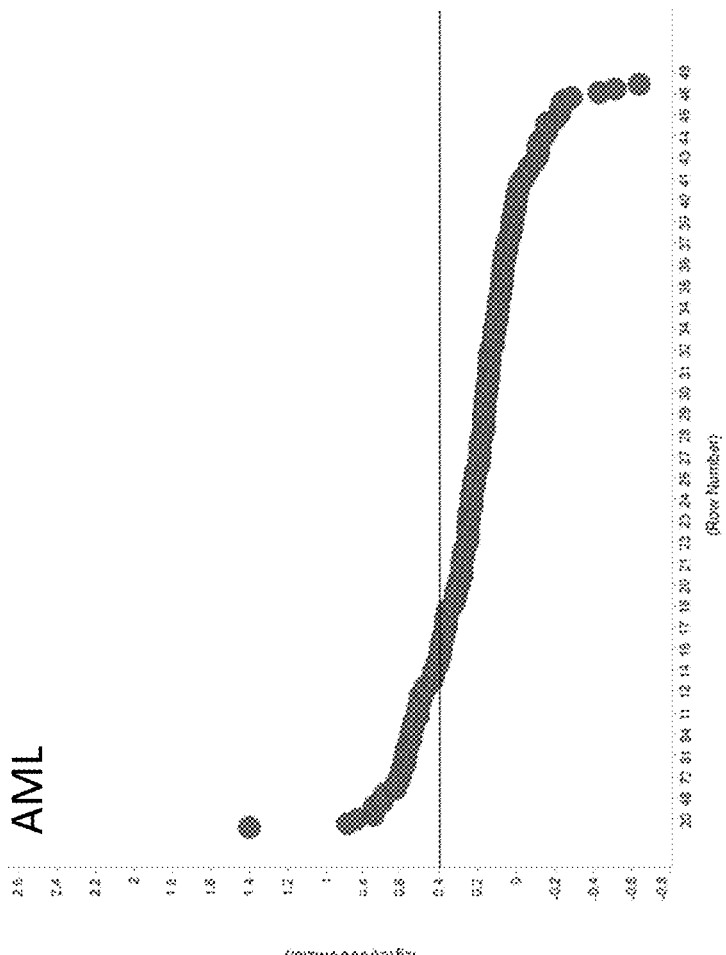
FIG. 4B shows the rank ordering of RARA SE strength, expressed as $\log_{10}$ RARA/MALAT1 for all AML cancer cell lines and patient samples analyzed by ChIP-seq in FIG. 3.
Figure 4A:
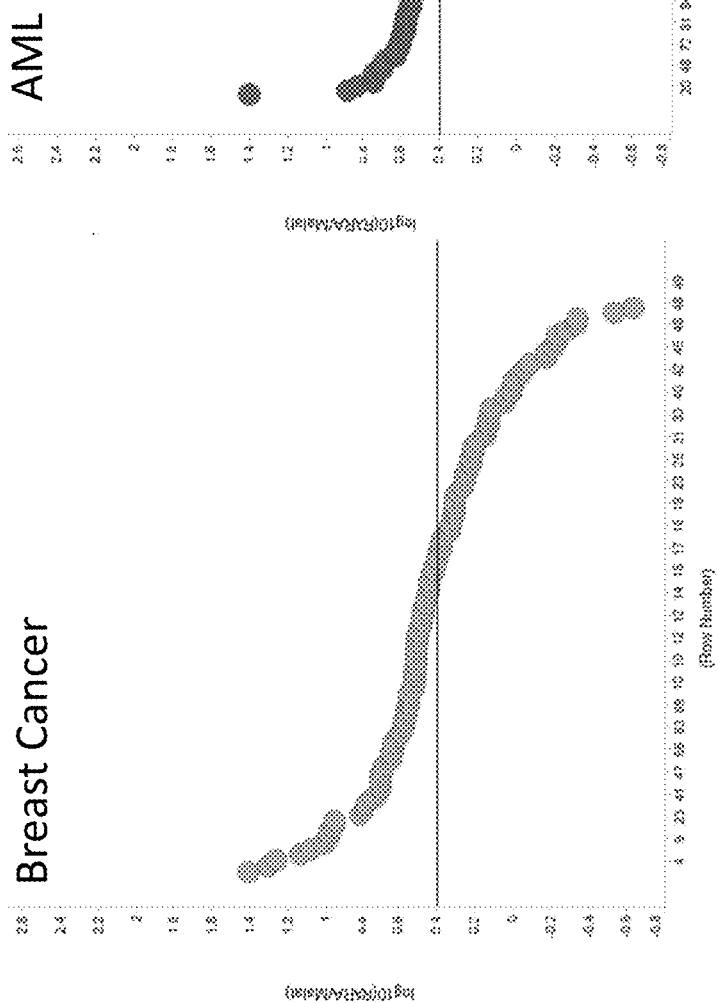
FIG. 4A shows the rank ordering of RARA SE strength, expressed as $\log_{10}$ RARA/MALAT1 for all breast cancer cell lines and patient samples analyzed by ChIP-seq in FIG. 3.
Figure 5:
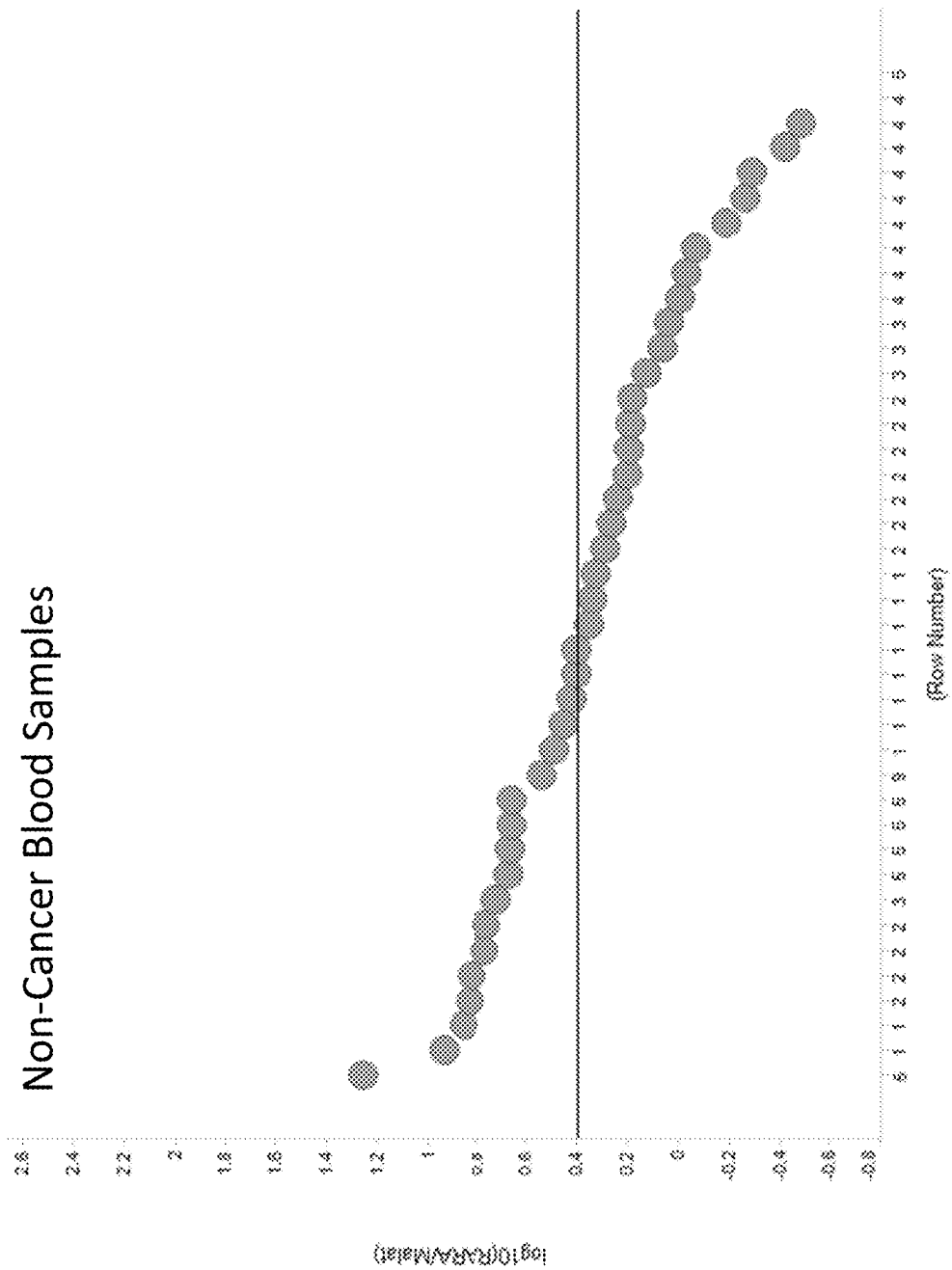
FIG. 5 shows the rank ordering of RARA SE strength, expressed as $\log_{10}$ RARA/MALAT1 for all normal hematological cell lines and patient samples analyzed by ChIP-seq in FIG. 3.

The $\log_{10}$ ratio of RARA/MALAT1 for all of the breast cancer and AML cell lines and patient samples are graphed as shown in FIGS. 4A and 4B, respectively. The 0.4 $\log_{10}$ threshold shown in each graph is the lowest SE strength found to be sensitive to tamibarotene in in vitro cell lines. As can be seen in these graphs, a certain percentage of samples of each cancer type falls above this threshold. FIG. 5 shows the $\log_{10}$ ratio of RARA/MALAT1 for normal hematological cell lines and patient samples tested. As can be seen, a certain percentage of samples of each hematological cell tested falls above the threshold, suggesting that this type of patient stratification would be useful to identify subjects with hematological disorders that would be responsive to a RARA agonist.

RARA SE rank is calculated using ROSE as described in U.S. Pat. No. 9,181,580, the disclosure of which is herein incorporated by reference. First, ROSE is used to calculate the enhancer scores for all of the breast cancer and AML cell lines and patient samples. Within each sample, the enhancers are ranked by score, and the rank of the RARA super-enhancer is the rank of the enhancer overlapping the RARA gene (chr17:38465444-38513094) with the highest score.

Figure 6:
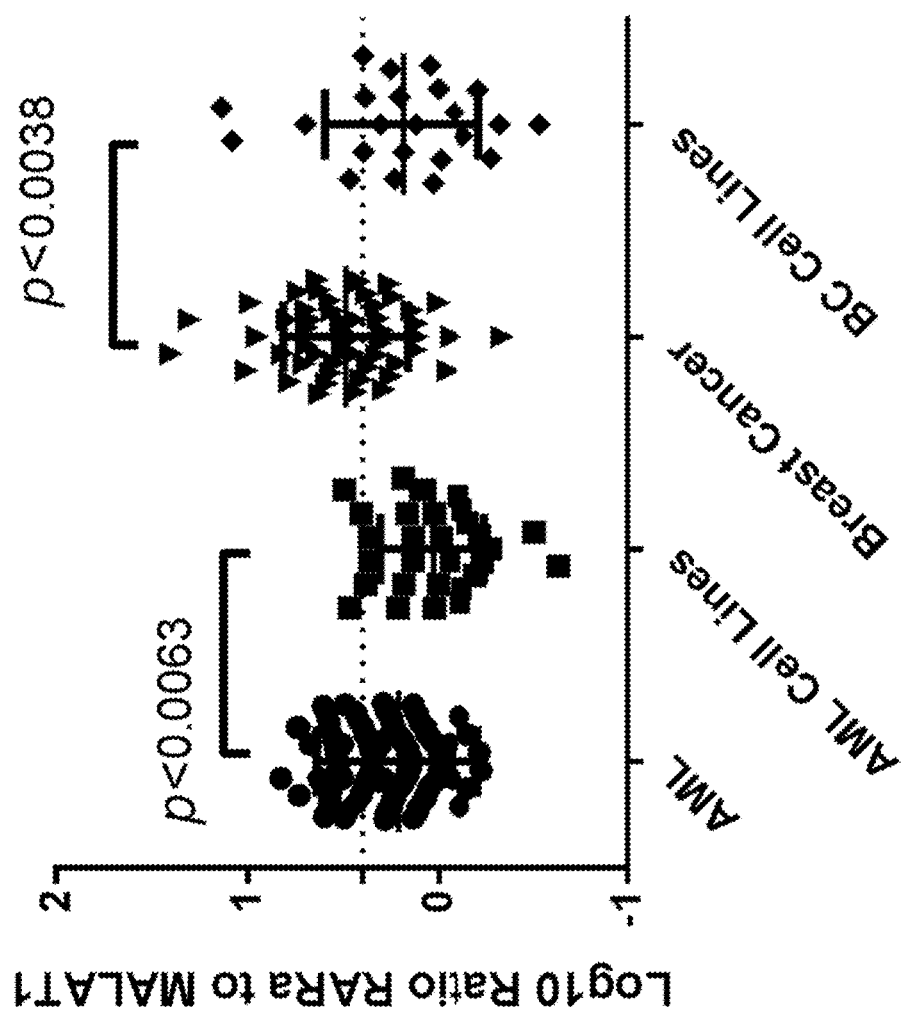
FIG. 6 shows a scatter plot of RARA SE strength, expressed as $\log_{10}$ RARA/MALAT1 for patient samples versus cell lines in the various AML and breast cancer cells analyzed by ChIP-seq in FIG. 3.

FIG. 6 shows a comparison of the $\log_{10}$ ratio of RARA/MALAT1 for cell lines versus patient samples in breast cancer and AML. As can be seen in this figure, patient samples in both cancer types have a statistically significant higher level RARA than corresponding cell lines. This demonstrates that high RARA super enhancer levels are not an in vitro phenomenon limited to cell lines. In addition, this illustrates that a higher proportion of the patient samples would be expected to show a response to RARA agonist than cell lines.

Example 2. Screening of Various RaR Modulator Compounds Against Breast Cell Cancer Panel I. Materials All cell lines are obtained from ATCC and cultured at 37° C. in 5% $CO_2$. All are grown in RPMI1640 supplemented with 10 mM HEPES buffer, 2 mM L-glutamine, 50 U/mL penicillin, 50 U/mL streptomycin and 10% fetal bovine serum (FBS, all from Invitrogen). Cells lines included AU565, SKBR3, T47D, HCC1143, MCF7, ZR-75-1, and HCC1569.

Tamibarotene, AM580, and tretinoin are obtained from Sigma Aldrich. Tazarotenic acid is obtained from Carbosynth. Adapalene, BMS195614, BMS493, BMS961 is obtained from Tocris. Etretinate is obtained from Santa Cruz. Tazarotene is obtained from Selleckchem.

The agonist specificity of the various test compounds for each type of RaR is assessed at Life Technologies using their SelectScreen® Nuclear Profiling Services. Obtained values are shown in the table below:

arrayed in 10 point quadruplicate dose response in DMSO stock in 384-well compound plates. After addition of compound, plates are incubated for five or ten days in a 37° C. incubator.

Cell viability is read out using ATPlite (Perkin Elmer) or CyQuant (Life Technologies). For ATPlite, plates are removed from the incubator and brought to room temperature prior to use. Lyophilized powder of ATPlite reagent is resuspended in lysis buffer and diluted 1:2 with distilled water. 25 µL of this solution is added to each well using the Biotek liquid handler. Plates are incubated for 15 min at room temperature before the luminescence signal was read on an Envision Plate Reader (Perkin Elmer). For CyQuant, reagents are mixed as per manufacturer's instructions in PBS (Gibco). Reagent are added using a multichannel pipet and plates are replaced in incubator for 30 minutes prior to readout on an Envision Plate Reader (Perkin Elmer).

Data acquired as described is stored and grouped in Microsoft's Excel and analyzed using GraphPad Prism Software. Curve fits to calculate EC50 and Emax are done in GraphPad Prism version 6.0 using four parameter (Hill slope not assumed to be equal to 1) non-linear regressions with the log 10 transformed data of the compound concentrations plotted against the percent viability of the cells when normalized to DMSO only treated wells included on the plate. Edge wells were excluded.

Figure 2:
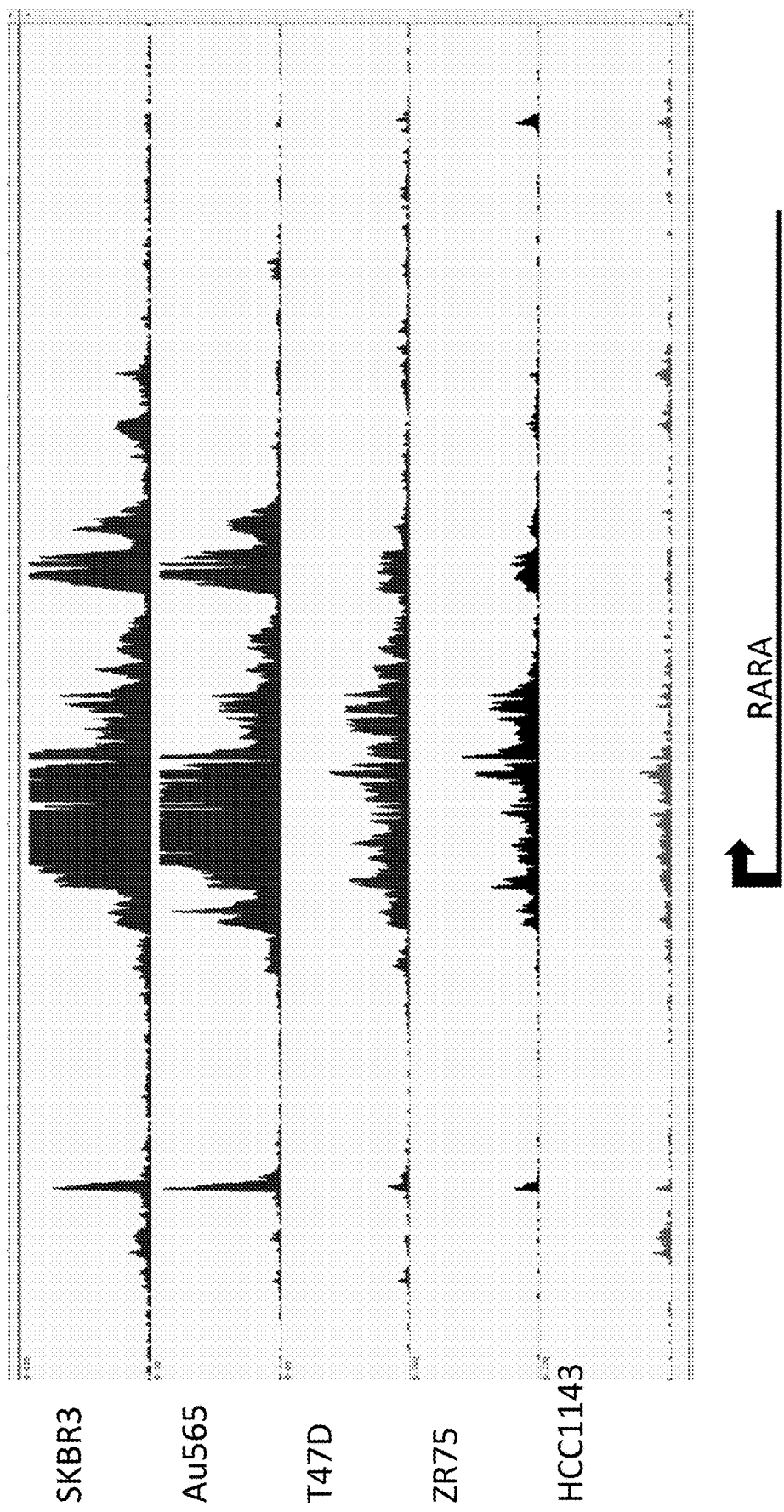
FIG. 2 depicts the level of H3K27Ac reads across the RARA locus as determined by ChIP-seq in 5 different breast cancer cell lines. "RARA" indicates the location of the RARA gene in the fragment of DNA analyzed.
Figure 7:
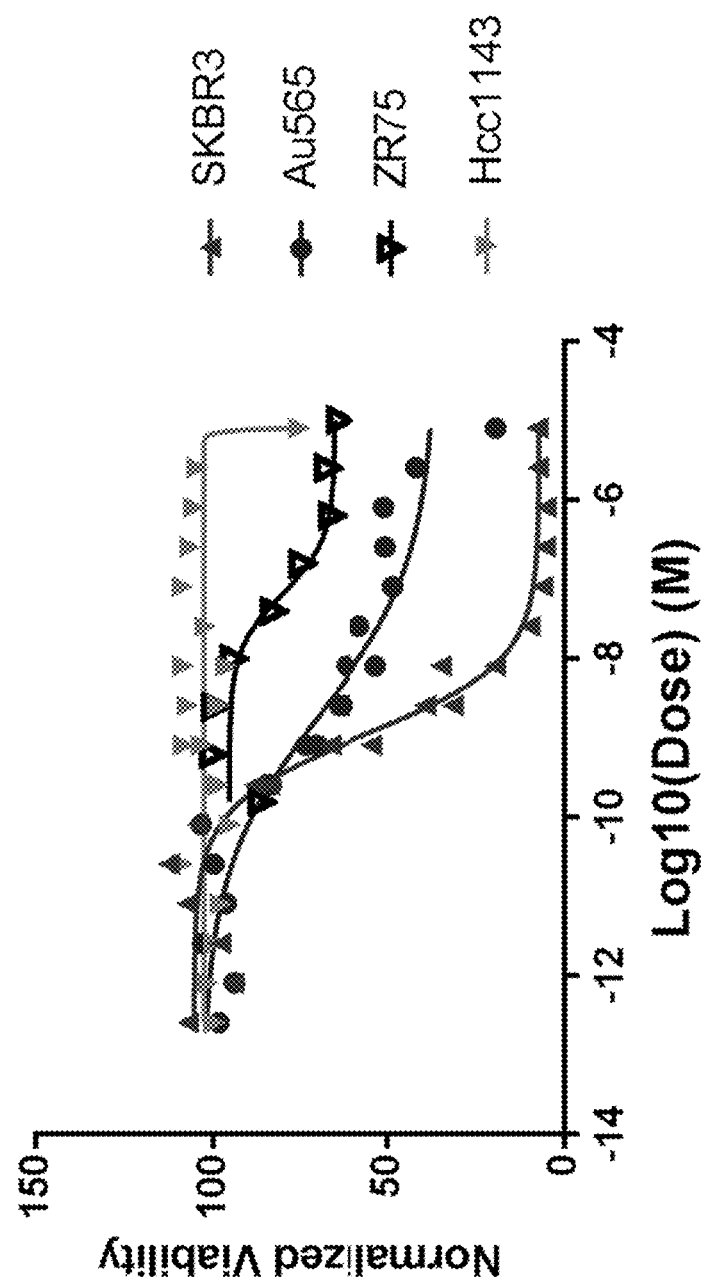
FIG. 7 shows the viability of various breast cancer cell lines in the presence of varying doses of tamibarotene after 5 days of treatment.

As shown in FIG. 7, four different breast cell cancer lines exhibit different responses to tamibarotene, with a sensitivity order of SKBR3>Au565>ZR75>Hcc1143. This correlates very well with the level of super-enhancer at the RARA site as shown in FIG. 2. The correlation of sensitivity to tamibarotene to super-enhancer strength ($\log_{10}$ $EC_{50}$ vs RARA/MALAT1 super enhancer ratio) for 7 different breast

| Compound | Stated specificty | RAR alpha | | RAR beta | | RAR gamma | | RAR-a/RAR-g Selectivity | |
|---|---|---|---|---|---|---|---|---|---|
| | | EC50 | % max | EC50 | % max | EC50 | % max | EC50 | % max |
| Adapalene | RAR | 5.011 | 102.2 | 9.732 | 69.36 | 17.26 | 87.7 | 3.4444 | 1.1653 |
| BMS753 | RARa | 1.434 | 122.2 | 700.8 | 6 | 136 | 19.83 | 94.8396 | 6.1624 |
| Tannibarotene | RARa | 0.2334 | 187.6 | 417.8 | 114.9 | 48.59 | 106.1 | 208.1834 | 1.7681 |
| AM580 | RARa | 0.2515 | 199 | 144.8 | 78.24 | 4.951 | 87.06 | 19.6859 | 2.2858 |
| Tazarotenic | RAR | 0.3532 | 121.4 | 5.171 | 71.88 | 1.101 | 78.33 | 3.1172 | 1.5499 |
| Tretinoin | RA | 1.095 | 149.4 | 1.076 | 92.77 | 1.732 | 99.37 | 1.5817 | 1.5035 |
| BMS961 | RARg | 1169 | 53.22 | 33510 | 149.8 | 3.74 | 114.2 | 0.0032 | 0.4660 |
| BMS493 | Antagonist | 27.42 | −3.417 | 0 | 0 | 511.5 | −13.41 | | |
| BMS195614 | Antagonist | 1339 | −31.01 | 0 | 0 | 433.6 | −14.57 | | |

As can be seen in the above table tamibarotene, BMS753 and AM580 have the greatest specificity for RARA over RaR-γ, thus confirming their status as RARA specific agonists. This specificity is important because agonism of RaR-γ is associated with toxicity. Agonism of RaR-ß is not known to contribute to efficacy or toxicity and therefore should not affect the therapeutic potential of an agonist.

II. Medium Throughput Screening.

Figure 8:
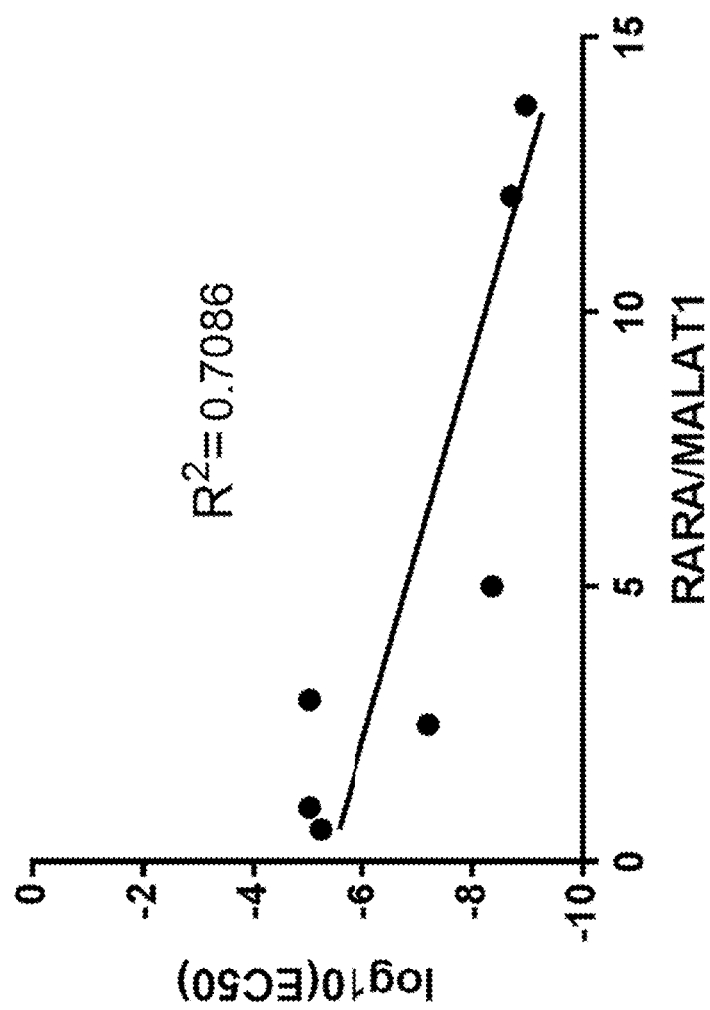
FIG. 8 shows the correlation between the $\log_{10}$ of tamibarotene $EC_{50}$ versus RARA SE strength (RARA/MALAT1 fold enrichment) for seven different breast cell cancer lines.

On the day of the experiment, cells are homogenized using Accumax (EMD Millipore), counted, and adjusted to 40,000 cells/ml for breast cancer lines and 60,000 cells/mL for AML in appropriate growth media. Using a Biotek EL406, 50 µl of cells are distributed into white (ATPlite) or black (CyQuant) 384-well plates (Thermo). Cells are returned to 37° C. incubator to allow adhesion. After three hours, compounds are added to plates using a 20 nl 384-well pin transfer manifold on a Janus workstation. Stocks are cell cancer lines is shown in FIG. 8 to have a correlation ($R^2$) value of 0.7086.

Figure 9:
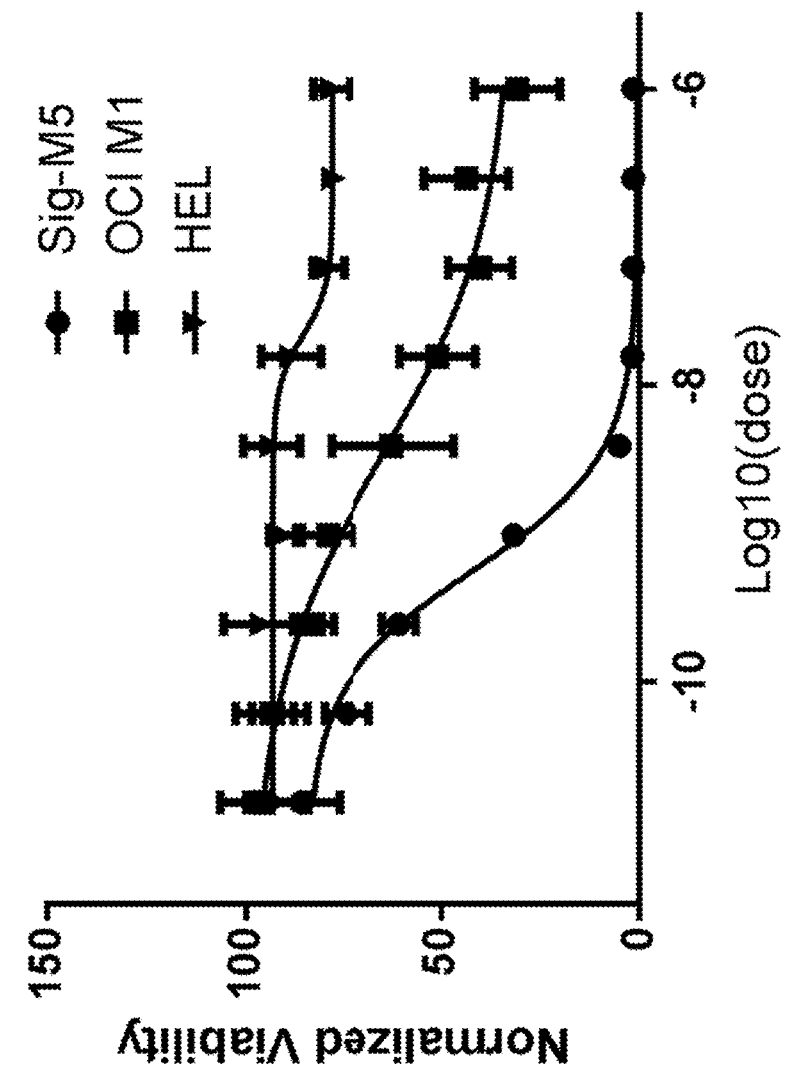
FIG. 9 shows the viability of various AML cell lines in the presence of varying doses of tamibarotene after 5 days of treatment.
Figure 10:
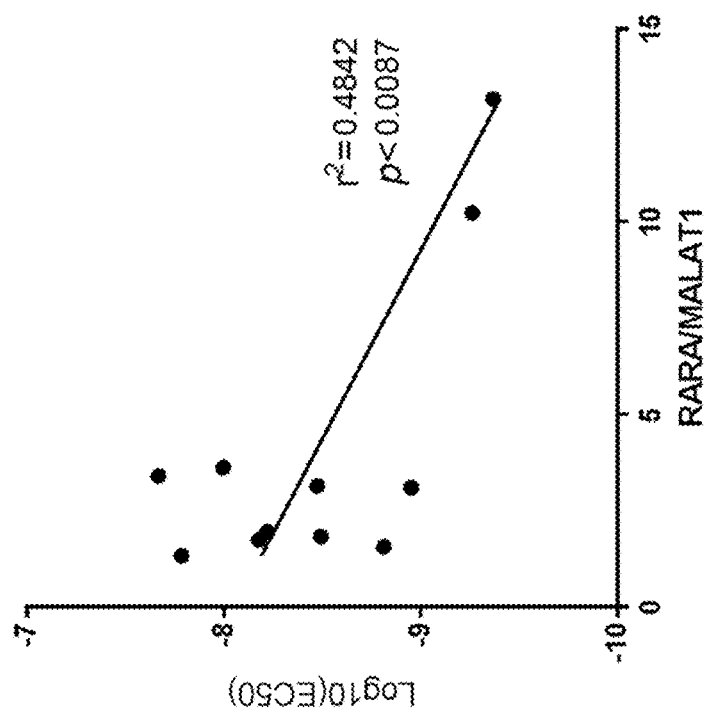
FIG. 10 shows the correlation between the $\log_{10}$ of tamibarotene $EC_{50}$ versus for eleven different AML cell lines.
Figure 23B:
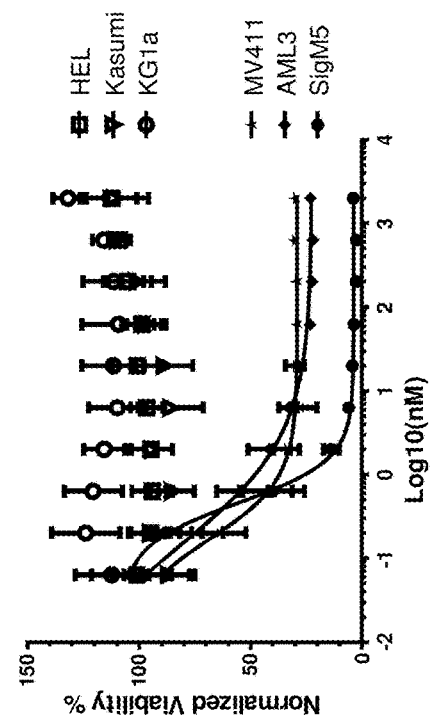
FIG. 23B depicts the responsiveness of those same 6 AML cell lines to tamibarotene treatment.
Figure 23A:
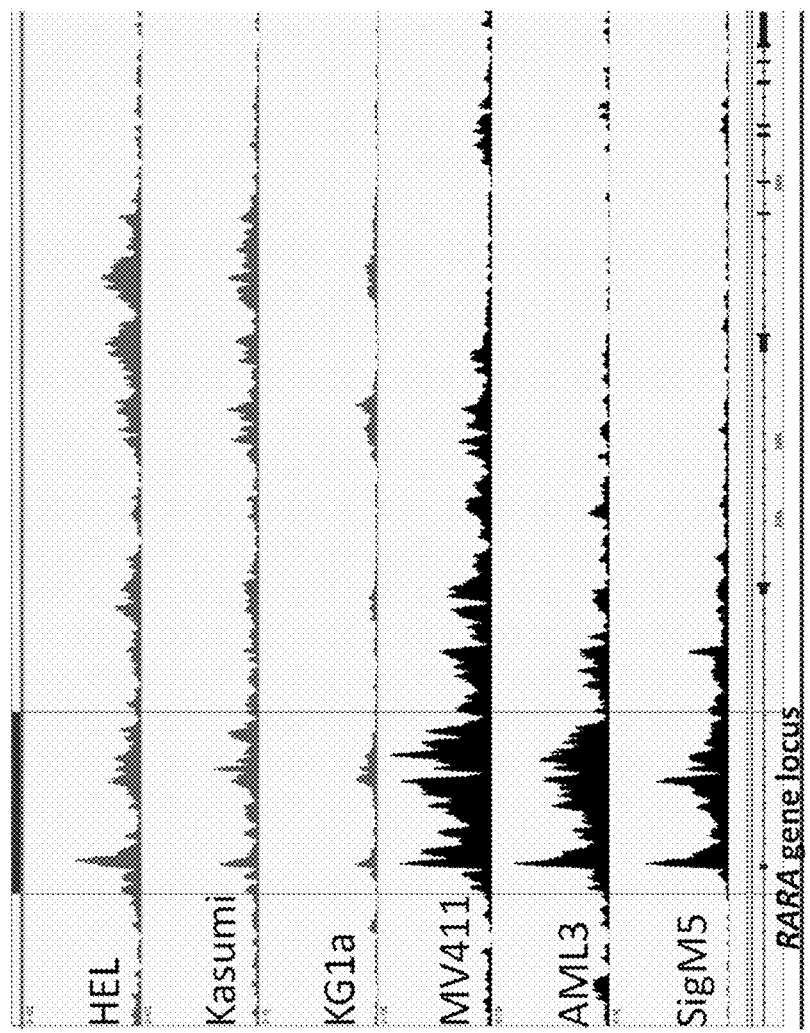
FIG. 23A depicts RARA super enhancer strength in 6 AML cell lines.

As shown in FIG. 9, three different AML cell lines exhibit different responses to tamibarotene, with a sensitivity order of SigM5>OCI M1>HEL. As shown in FIGS. 23A-B, two additional AML cell lines, MV411 and Kasumi, are assayed along with SigM5 and HEL for sensitivity to tamibarotene and demonstrated a sensitivity order of SigM5>MV411>HEL=Kasumi. The correlation of sensitivity to tamibarotene to super enhancer strength ($\log_{10}$ $EC_{50}$ vs RARA/MALAT1 super enhancer ratio ("IEA") for 11 different AML cell lines is shown in FIG. 10 to have a correlation ($R^2$) value of 0.3635, but that value increases to 0.5680 when one cell line that shows significant deviation from the norm (higher SE but lower than expected sensitivity), HEL, is not taken into account.

Example 3. Measurement of RARA RNA and Protein Expression Levels

Expression level measurements are employed to ascertain the level of mRNA for the RARA gene tagged. mRNA levels correlate well with enhancer levels and therefore are also predictive sensitivity to RARA agonists. We use various means of measuring RNA as set forth below.

I. Array-Based Technology.

Expression levels in HCC1143 and AU565 are assessed with triplicate batches of $1 \times 10^6$ cells. RNA is extracted from cells using Trizol® and purified using the mirVana™ RNA purification kit (both from Life Technologies), following the manufacturer's protocol. RNA levels are read out on Affymetrix PrimeView™ arrays at the Dana Farber Cancer Institute Microarray Core (http://mbcf.dfci.harvard.edu/).

Figure 11:
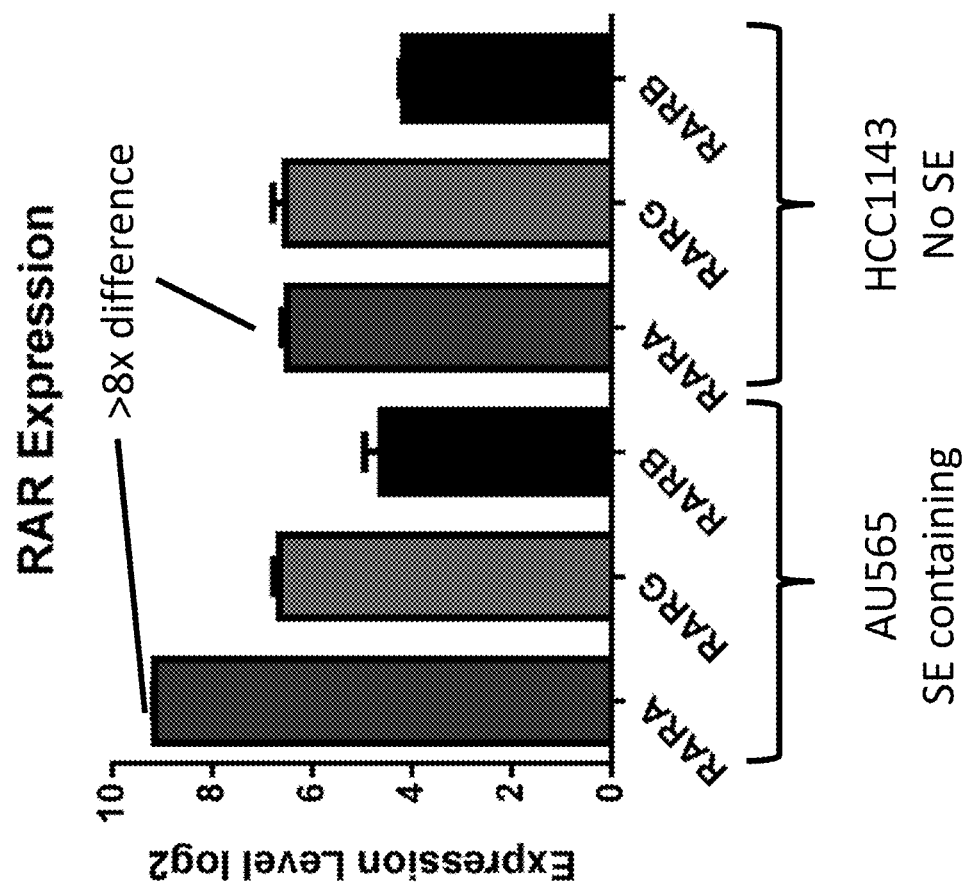
FIG. 11 shows the mRNA expression levels of the three different RAR subtypes (RaR-α ("RARA"); RaR-β ("RARB"); and RaR-γ ("RARG")), as measured by Affymetrix Array-Based analysis for a tamibarotene responsive (Au565) and non-responsive (HCC1143) breast cancer cell line.

FIG. 11 shows the levels of mRNA expression of various RaR subtypes in a tamibarotene responsive (Au565) and non-responsive (HCC1143) cell line measured using the above protocol. Expression of RARA mRNA is 8-fold higher in the responsive cell line versus the non-responsive cell line, while expression of RaR-ß and RaR-γ is not significantly different between the cell lines. This confirms that RARA mRNA expression analysis correlates with RARA super enhancer strength and sensitivity to an RARA agonist, as well as demonstrating that RARA mRNA level can be used to predict sensitivity to such agonist.

Figure 12:
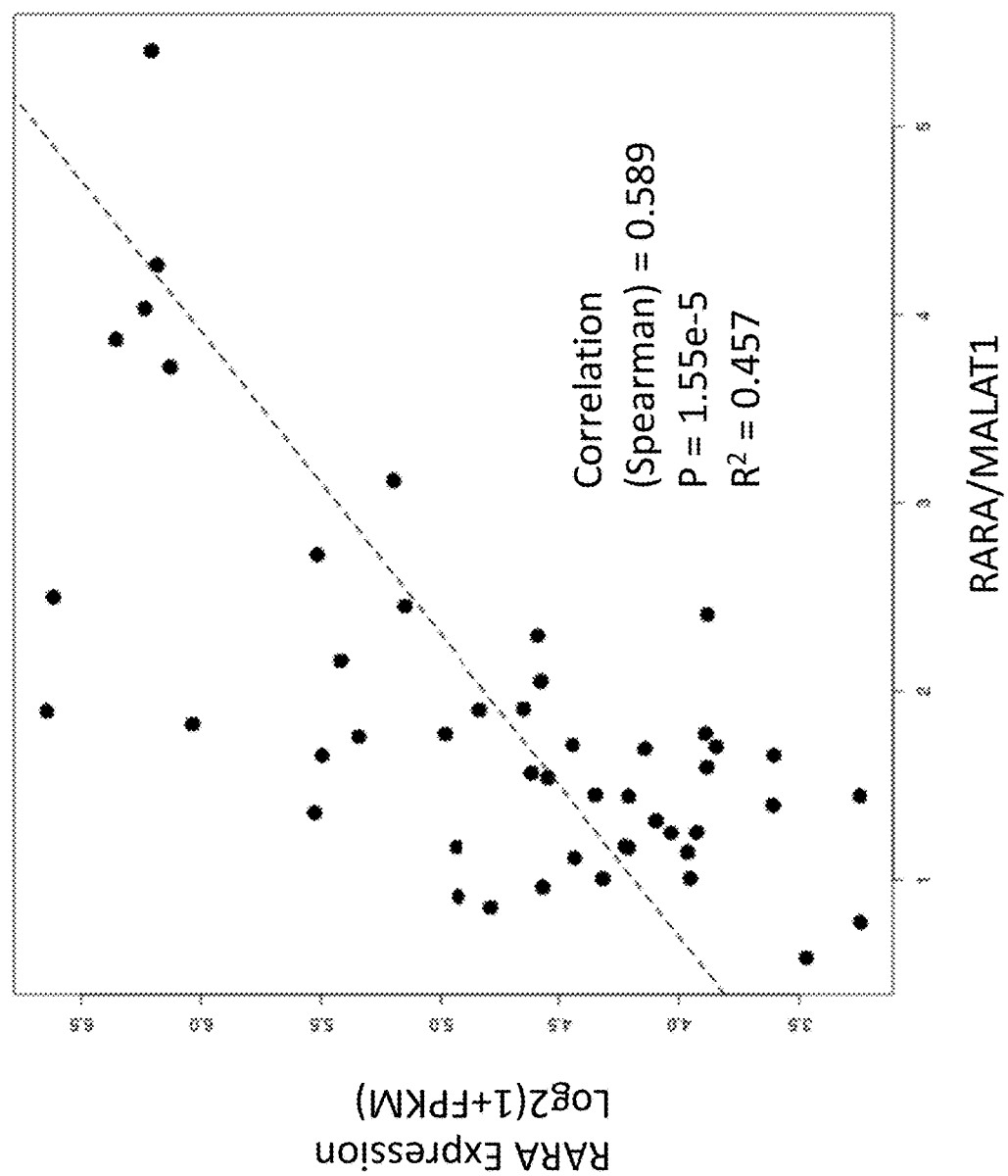
FIG. 12 show the correlation between mRNA expression ($\log_2(1+\text{FPKM})$) and RARA SE strength (RARA/MALAT1 fold enrichment) for 48 different AML patient samples using RNA-Seq.

II. RNA-Seq. RARA expression levels are quantified by RNA-Seq. Poly-A RNA-Seq is performed and reads are aligned to the HG19 transcriptome using RSEM software (parameters=--samtools-sort-mem 3G --ci-memory 3072 --bowtie-chunkmbs 1024 --quiet --output-genome-bam --bowtie2 --strand-specific) and then mRNA quantification is done using RSEM and reported in Transcripts Per Million (TPM). The plotted values show the log 2(FPKM+1) levels for RARA (y-axis) versus the super-enhancer score (RARA/MALAT1) for 48 primary AML patients (FIG. 12) have a Spearman Correlation of 0.589 and a $R^2$ value of 0.0457.

Figure 13:
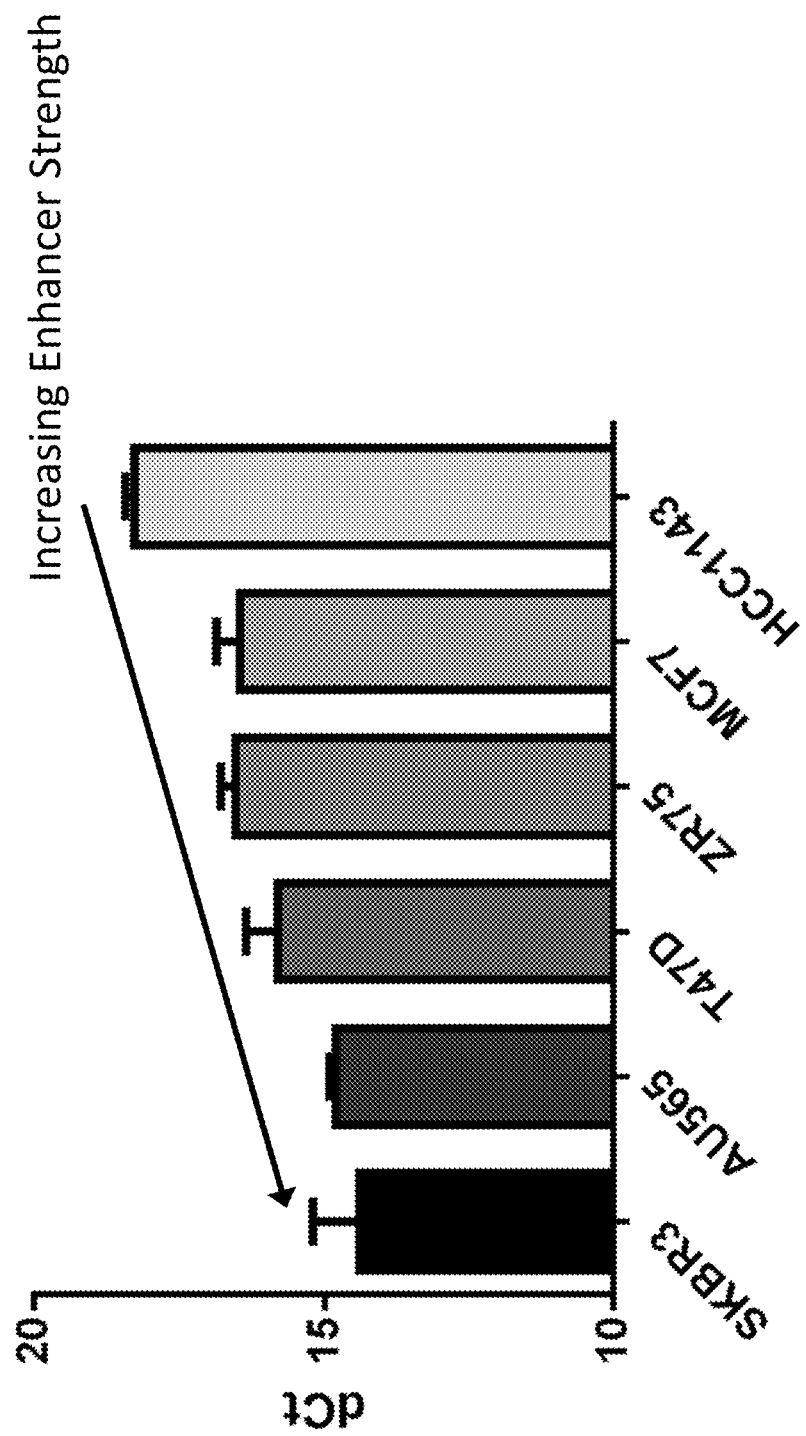
FIG. 13 shows the inverse mRNA expression level as measured by rt-qPCR and expressed as dCt for 5 different breast cancer cell lines.
Figure 14B:
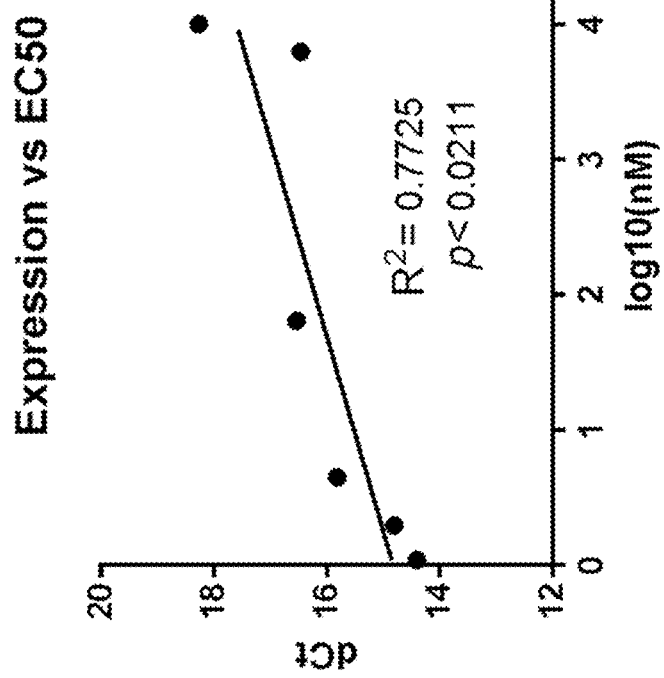
FIG. 14B shows the correlation between mRNA expression levels as measured by rt-qPCR and responsiveness to tamibarotene (as measured by $\log_{10} EC_{50}$) for seven different breast cell cancer lines.
Figure 14A:
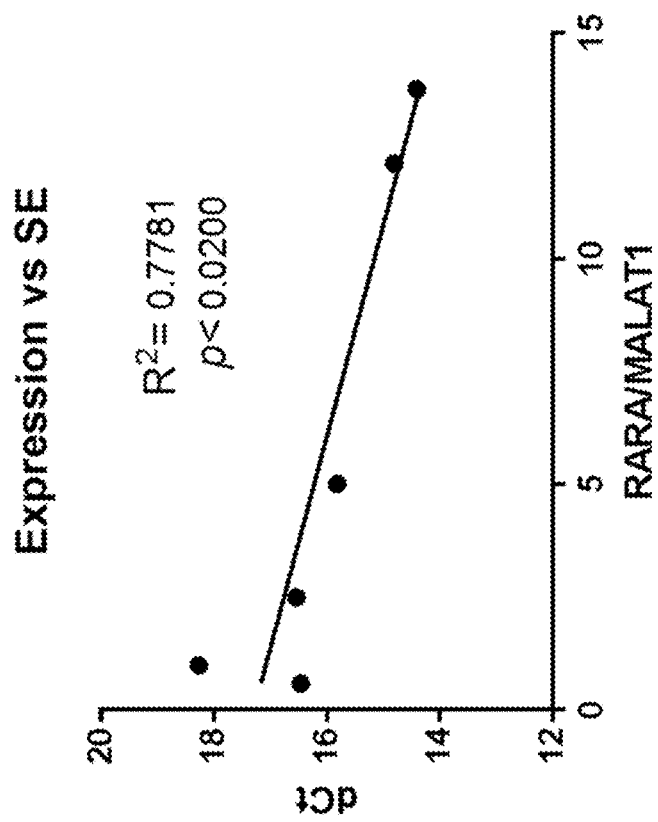
FIG. 14A shows the correlation between mRNA expression levels as measured by rt-qPCR and RARA SE strength (RARA/MALAT1 fold enrichment) for seven different breast cell cancer lines.

III. qPCR. Expression is also studied using rt-qPCR. Cells were counted and plated at the 200,000 cells per mL for each cell line. Cells are then treated with 500 nM tamibarotene or vehicle for 48 hours. RNA is extracted from cells using Trizol® and purified using the mirVana™ RNA purification kit (both from Life Technologies), following the manufacturer's protocol. The purified RNA is converted to cDNA using SuperScript® Vilo™ reverse transcriptase (Life Technologies) following the manufacturer's protocol. Transcript abundance is then measured using Taqman® probes (Life Technologies) to RARA and to 18s rRNA for normalization. For RARA, probe Hs00940446_m1 is used with an amplicon length of 68 and spanning exons 6-7. For 18S rRNA probe 4319413E with a 187 bp amplicon was used. The qPCR is run using Taqman® Gene Expression Master Mix (Life Technologies) following the manufacturer's protocol. Analysis of the data is performed using the delta Ct method. The 18s rRNA Ct value is subtracted from each sample to normalize to cell abundance. The dCt values indicate relative fold differences in RNA transcript abundance. Lower dCt values indicate higher mRNA expression. The results for rt-qPCR values for 6 different breast cancer cell lines graphed in order of their SE strength (from highest (SKBR3) to lowest (HCC1143) is shown in FIG. 13. As can be seen rt-qPCR value correlate well with super enhancer strength at the RARA locus. FIGS. 14A-B show that the dCT values have a high correlation with SE strength and with sensitivity as measured by $EC_{50}$.

IV. Western Blotting.

Figure 15:
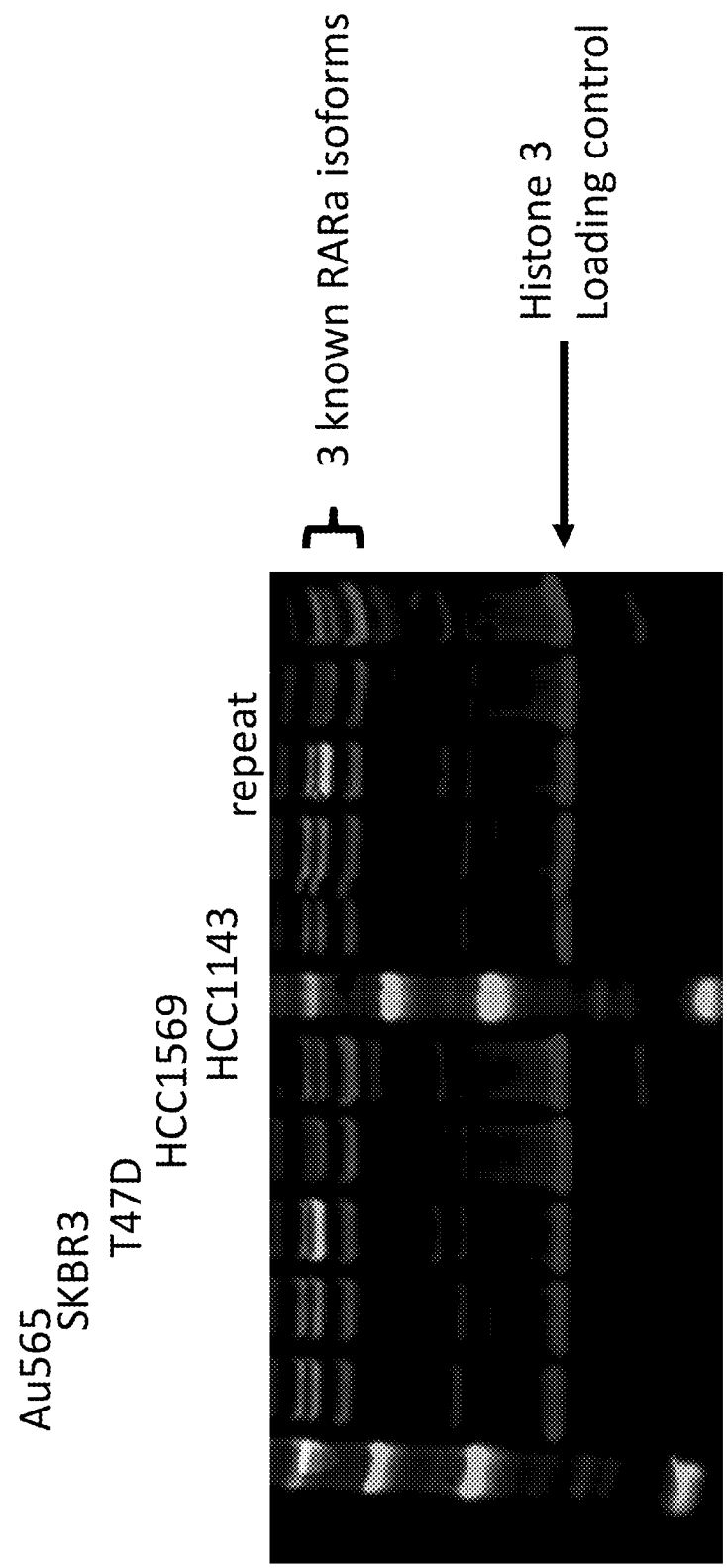
FIG. 15 is a Western blot depicting the protein level of three different known RARA isoforms in 5 different breast cell cancer lines.

Cells are counted and adjusted to 2 million per cell line and pelleted. Cell pellets are lysed using RIPA buffer (Life Technologies) plus Roche protease cocktail in a 100 μL volume. Samples are cleared by centrifugation at 20,000×g for 5 minutes. Ten L of sample is loaded on to 4-12% Bis-Tris gels (Life Technologies). Antibodies used are Abcam 1791 histone H3 for loading control and Sigma Aldrich SAB 1404298 for RARA. The results are shown in FIG. 15. There does not appear to be a good correlation between RARA protein levels and either size of the super-enhancer or sensitivity of the cells to an RARA agonist. This confirms the prior results of another group that also demonstrated a lack of correlation between RARA protein expression and retinoid sensitivity (G Paroni et al., Oncogene, 31:3431-43 (2012); see FIG. 1C in reference).

V. Z-Score from TCGA.

Z-scores of expression from the TCGA datasets are obtained from the cBio Portal for Cancer Genomics (http://www.cbioportal.org/public-portal/).

VI. MDS Expression Measurements.

Raw Affymetrix expression data of 159 MDS patients and 17 normals associated with Gerstung et. al (PMID: 25574665) are downloaded from the NCBI Gene Expression Omnibus (GSE58831). The expression data is normalized in R using the "justRMA" function with default parameters to produce normalized probe-level values across all the samples. The value of the Affymetrix probe '203749_s_at' is used to represent the RARA mRNA level. The mean and standard deviation of RARA levels in the 17 normal samples is calculated and then used to generate RARA mRNA Z-scores.

Example 4. RARA Gene Copy Number is not Correlated with Sensitivity to Tamibarotene In order to rule out the possibility that sensitivity to tamibarotene was based on HER2 gene copy number and that RARA and HER2 amplification were co-dependent, as suggested by G. Paroni et al., supra., we analyze the copy number of the RARA and HER2 genes in two responsive breast cancer cell lines—Au565 and T47D. DNA is extracted using the QIAamp® DNA Mini Kit (Qiagen) following the manufacturer's instructions. The purified DNA is analyzed using a Human Cytoscan® HD microarray from Affymetrix. The data is processed using the package Aroma from Bioconductor in the statistical environment R, and graphed using base R graphics. As shown in FIGS. 16A-B, while the Au565 cell line has a higher HER2 gene copy number (Box 1) than RARA (Box 2), the same is not seen in the equally tamibarotene-responsive T47D line. Moreover, there is little difference in RARA gene copy number between the two cell lines. This demonstrates that amplification of RARA gene copy number is not dependent upon HER2 copy number and that sensitivity to an RARA agonist is not dependent upon HER2 copy number.

Example 5. Identification of RARA Associated Super Enhancers in Other Cancers We use the known location of the RARA super enhancer domain to probe additional patient cancer samples to determine if such cancers had a RARA super enhancer. We found a large super enhancer associated with RARA in both glioblastoma and neuroblastoma patient samples, but not in colorectal cancer samples (see FIGS. 17A-17C). This suggests that stratification of patients for treatment with a RARA agonist can also be carried out in patients suffering from either glioblastoma or neuroblastoma. Moreover, Z-score analysis of RARA mRNA levels suggest that certain subject suffering from colorectal cancer may be responsive to a RARA agonist, despite these super-enhancer results (see FIG. 30).

Example 6. Sensitivity of a HCC1954 Breast Cancer Cell Xenograft to Tamibarotene Breast cancer cell line (HCC1954)-derived xenograft models in BALB/c nude immunocompromised mice are prepared by Crown Biosciences (Beijing, China) essentially as follows.

Six to eight week old BALB/c nude immunocompromised mice, weighing between 18-20 g are inoculated subcutaneously at the right flank region with HCC1954 tumor cells ($5 \times 10^6$) in 0.1 ml of PBS (1:1 matrigel) for tumor development. When the mean tumor size reaches a volume between 100-200 mm$^3$ animals are matched by tumor volume into treatment groups to be used for dosing and dosing initiated. Tamibarotene is administered orally in pH 8 adjusted PBS, 1% DMSO on a daily schedule (QD, PO) for up to 21 days. The final dosage in mice is 6 mg per kg per day in the high dose arm (n=10) and 3 mg per kg per day in the low dose arm (n=10) in a 10 ml/kg volume. Mice in the vehicle arm (n=10) are given the same schedule, volume, and formulation but lacking drug. Tumor volume is measured twice weekly by caliper measurement.

Figure 18:
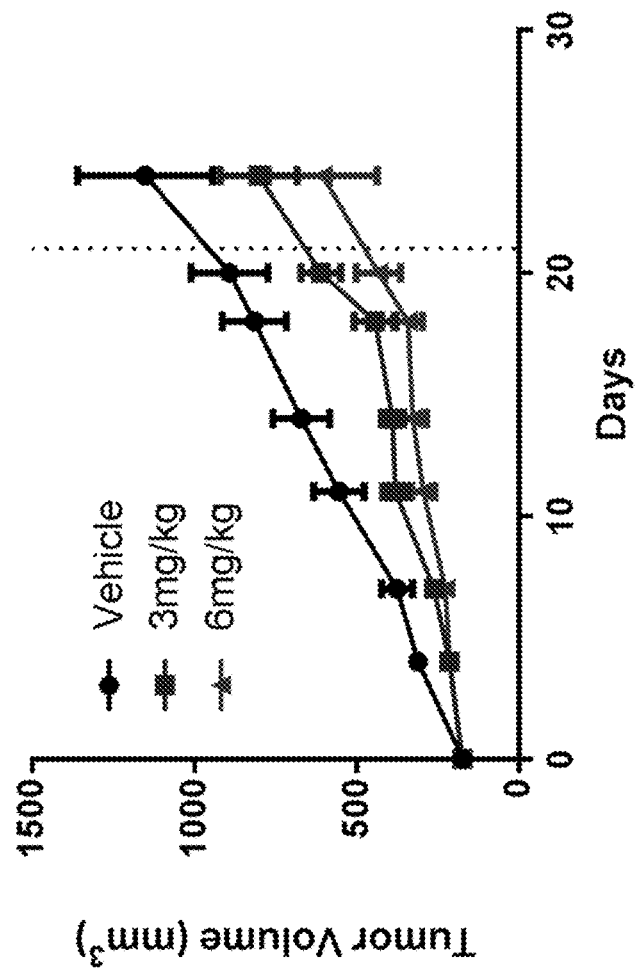
FIG. 18 depicts the response to various daily dosages of tamibarotene in a breast cancer cell line (HCC1945)-derived mouse xenograft model of breast cancer.

The results of these experiments demonstrate that tamibarotene reduces tumor volume in this model in a dose-dependent manner (FIG. 18). The reduction in tumor volume is just below statistical significance in the low-dose arm (p=0.0552) and statistically significant in the high dose arm (p=0.0048) by t-test using Welch's correction. The results in this xenograft model confirm the sensitivity of HCC1945 cells in culture to tamibarotene.

Example 7. RARA Super Enhancer Strength Ordinal Rank Cutoff in Breast Cancer

Figure 19:
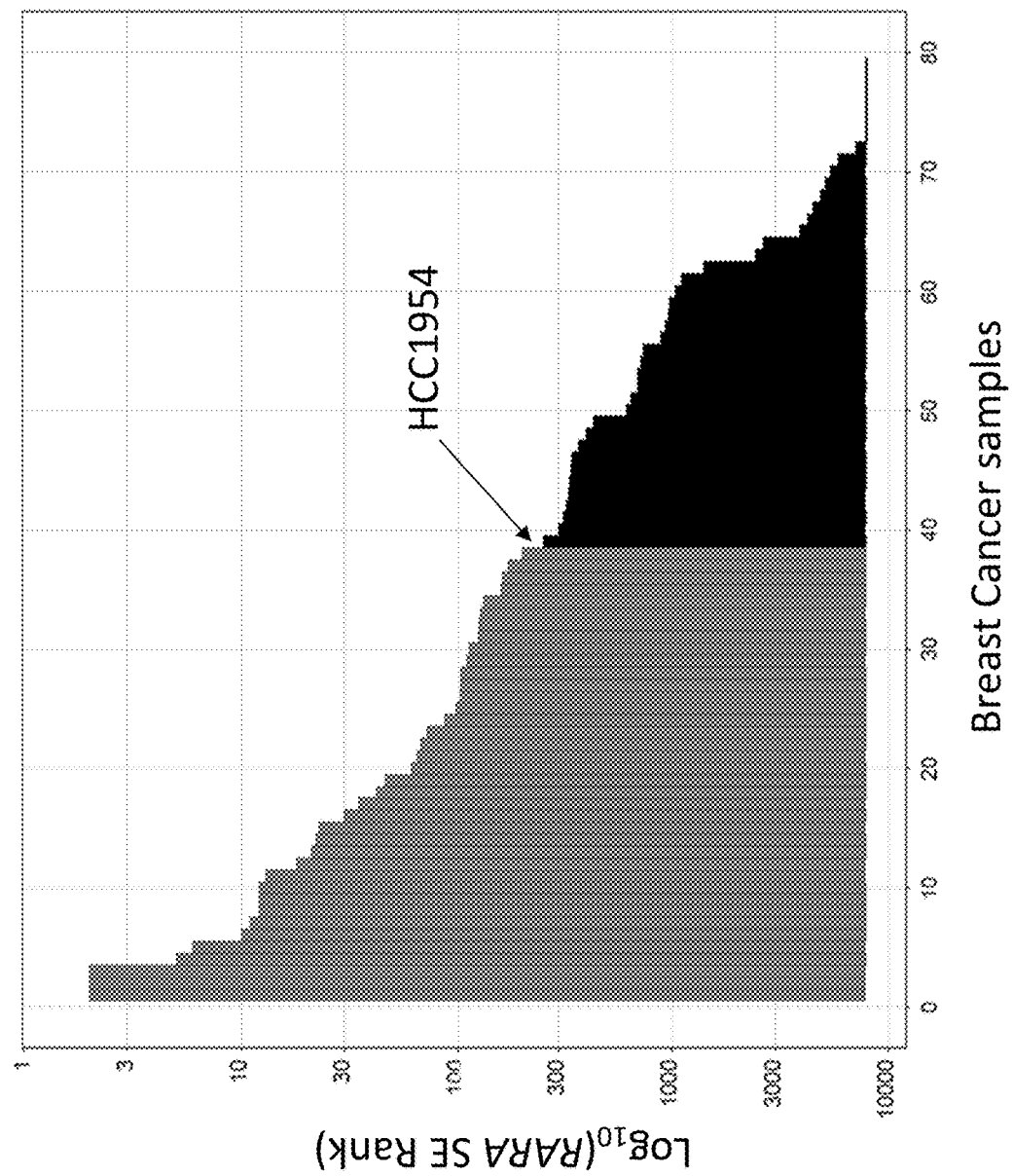
FIG. 19 depicts a $\log_{10}$ rank-ordered graph of RARA super enhancer strength ordinal in 80 breast cancer samples including the breast cancer cell line HCC1945.
Figure 20A:
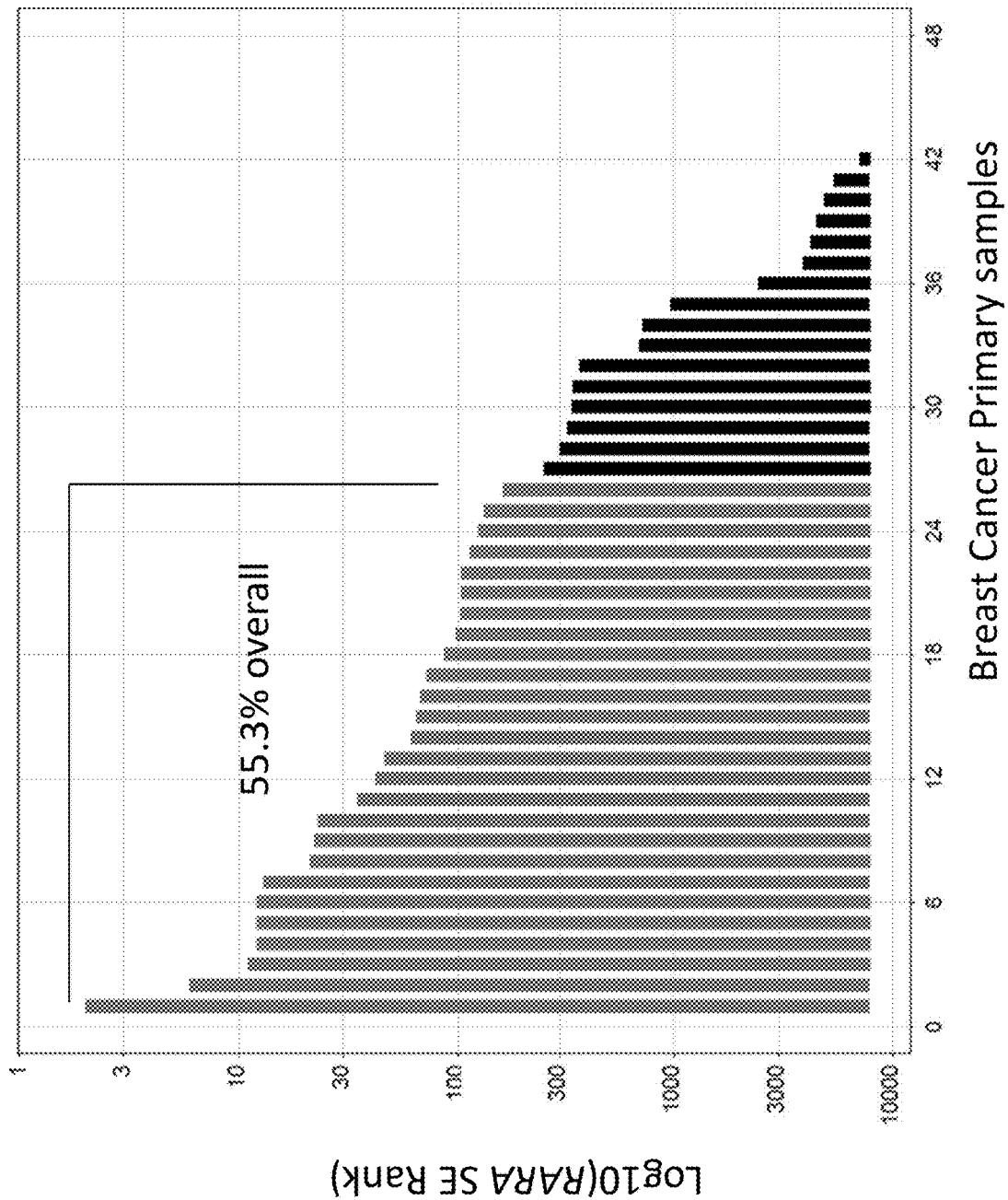
FIG. 20A depicts a $\log_{10}$ rank-ordered graph of RARA super enhancer strength ordinal in 48 patient breast cancer samples. The lighter colored bars represent samples whose RARA super enhancer strength ordinal was equal to or above the prevalence cutoff. Darker colored bars represent samples whose RARA super enhancer strength ordinal was below the prevalence cutoff.

The total enhancer/super enhancer profile of one-hundred seventy breast cancer samples (both patient samples and breast cancer cell lines, including HCC1954) are analyzed using H3K27Ac and ChIP-Seq as described in Example 1. In each of the samples, the ordinal rank of the RARA-associated enhancer in terms of strength (as measured by H3K27Ac) is determined as compared to other enhancers and super-enhancers in the same cell and the determined ordinal ranks plotted on a rank-order bar graph (FIG. 19). In HCC1954 it was determined that the RARA super enhancer was the 204$^{th}$ strongest enhancer in that cell (see FIG. 19). Based on this result and the responsiveness of HCC1954 to tamibarotene, we set the ordinal cutoff for potential tamibarotene-responsive breast cancer patients to those who have a RARA super enhancer in their tumor that is at least the 200$^{th}$ strongest. As determined from our analysis of 48 primary breast cancer tumor cell samples from human subjects, 55.3% of those samples had a RARA super enhancer that was at least the 200$^{th}$ strongest in those cells (FIG. 20A). Therefore, we set the prevalence cutoff at 55.3%. That same prevalence cutoff is also used as the RARA mRNA prevalence cutoff when identifying potential breast cancer responders to tamibarotene based on RARA mRNA measurements.

Figure 20B:
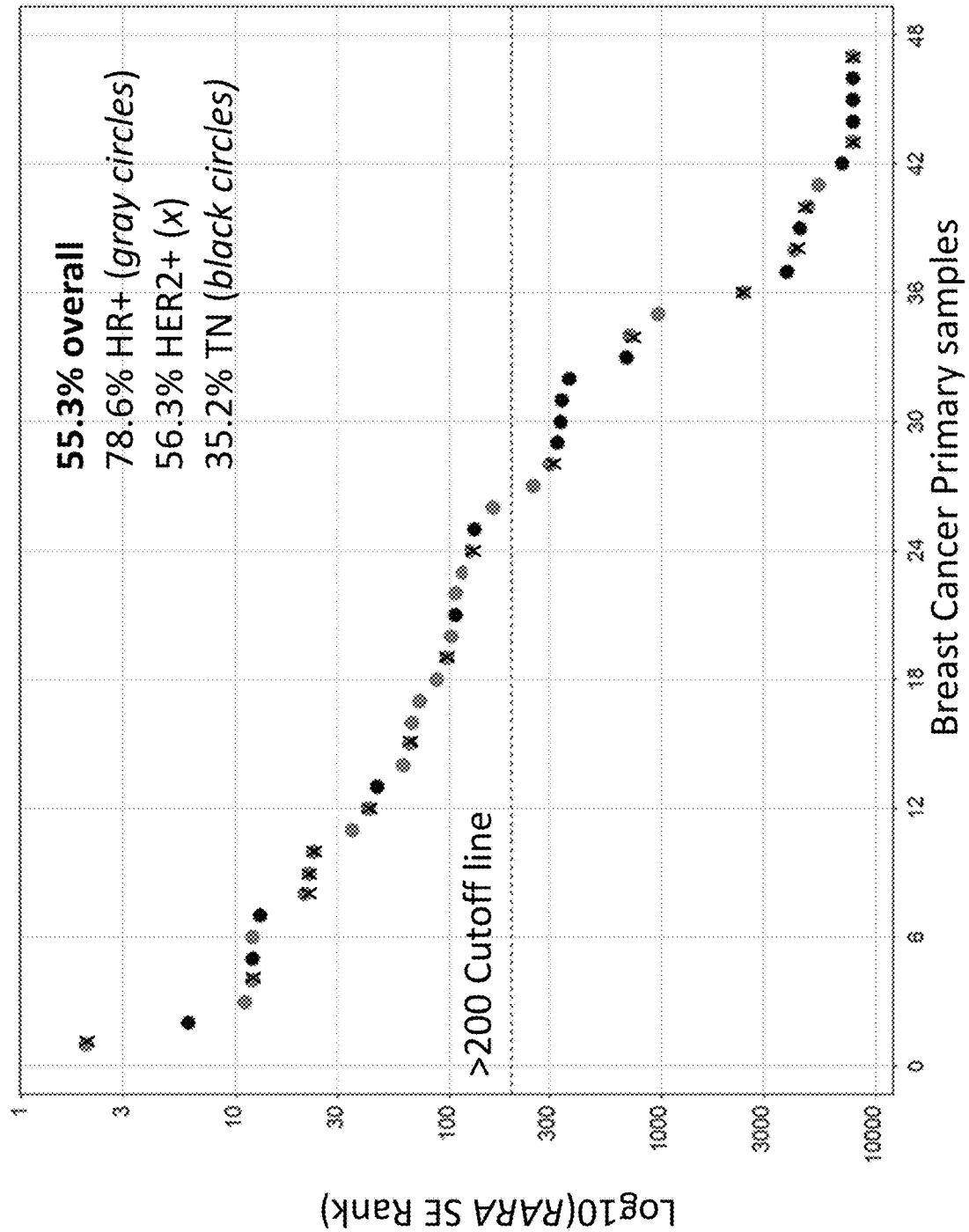
FIG. 20B depicts the same rank ordered graph as Panel A and further indicates the specific subtype of breast cancer (hormone receptor positive ($HR^+$), HER2 positive ($HER2^+$), or triple negative (TN)), as well as the calculated prevalence cutoff for each subtype.

When the primary breast cancer samples are further broken down by subtype, different prevalence cutoffs for each subtype are generated using the same RARA super enhancer ordinal cutoff of 200. These prevalence cutoffs are 78.6% for hormone receptor-positive; 56.3% for HER2 positive; and 35.2% for triple negative breast cancer (FIG. 20B).

Example 8. RARA mRNA Levels Correlate with Responsiveness to Tamibarotene in Breast Cancer PDXs Low Passage TumorGraft® models of human breast cancer in immunocompromised female mice (Harlan; nu/nu nude) are created by Champions Oncology (Baltimore, Md.) using the following protocol.

Stock mice are implanted with patient breast cancer tumor samples (n=3 for each separate patient sample and for the controls), which are allowed to grow to 1-1.5 cm$^3$. Tumors are then harvested from stock mice and fragments thereof are re-implanted unilaterally on the left flank of pre-study mice (female; Harlan; nu/nu nude, 5-8 weeks of age; n=3 for each separate patient sample and for the controls). When tumors reach approximately 100-300 mm$^3$, pre-study animals are matched by tumor volume into treatment groups to be used for dosing and dosing initiated on Day 0. Tamibarotene is administered orally in pH 8 adjusted PBS, 1% DMSO on a daily schedule at a final dose of 6 mg per kg body weight in a 10 ml/kg volume. Mice in the vehicle arm are given the same schedule, volume, and formulation, but lacking tamibarotene.

Figure 21B:
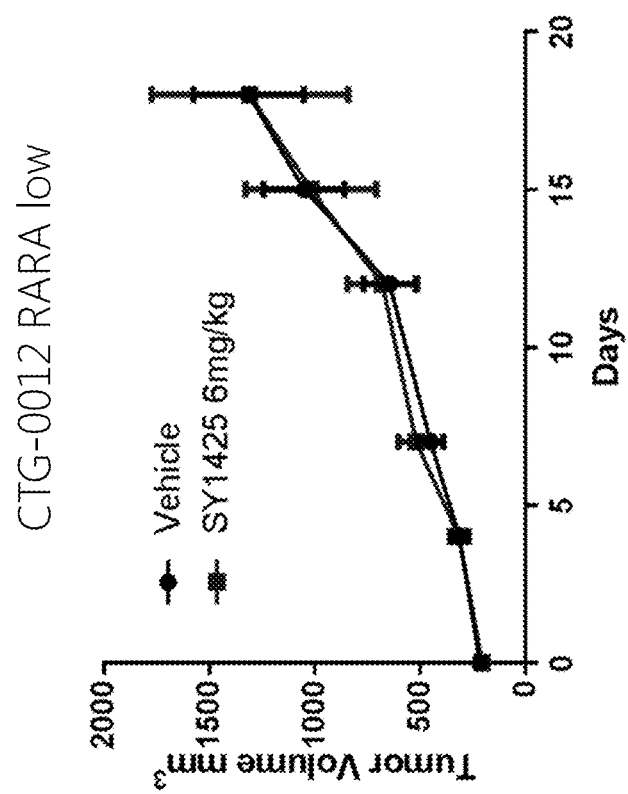
FIGS. 21A-B depict the response to daily dosing of tamibarotene (SY1425) in two different patient sample-derived mouse xenograft breast cancer models.
Figure 21A:
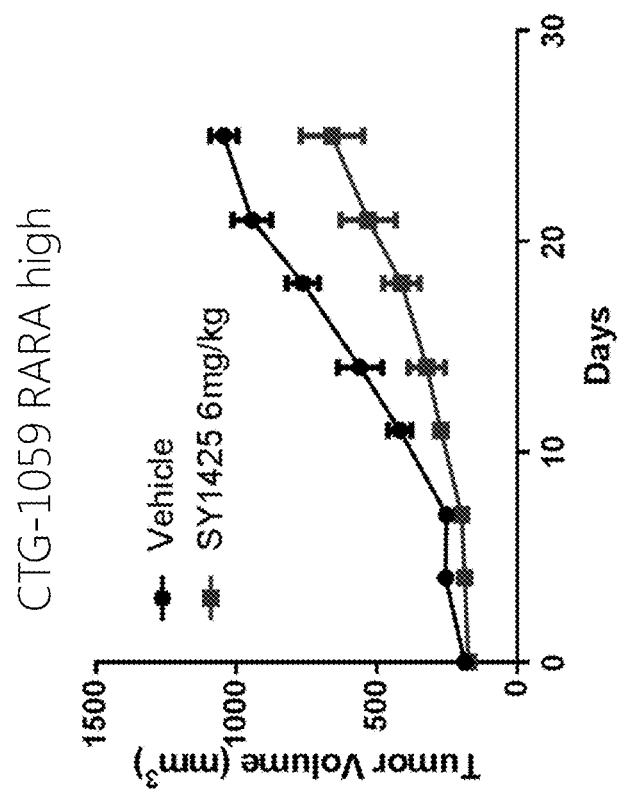

Tumor volumes are measured by caliper twice a week. A final tumor volume measurement is taken on the last day of treatment. FIGS. 21A-B show the responsiveness of two of these PDXs (CTG-1059 (high RARA mRNA) and CTG-0012 (low RARA mRNA) to tamibarotene ("SY1425"). CTG-1059 demonstrates a statistically significant decrease in tumor volume after 25 days of tamibarotene treatment as compared to a vehicle only control. CTG-0012 did not show any significant difference between tamibarotene and the control.

Figure 22:
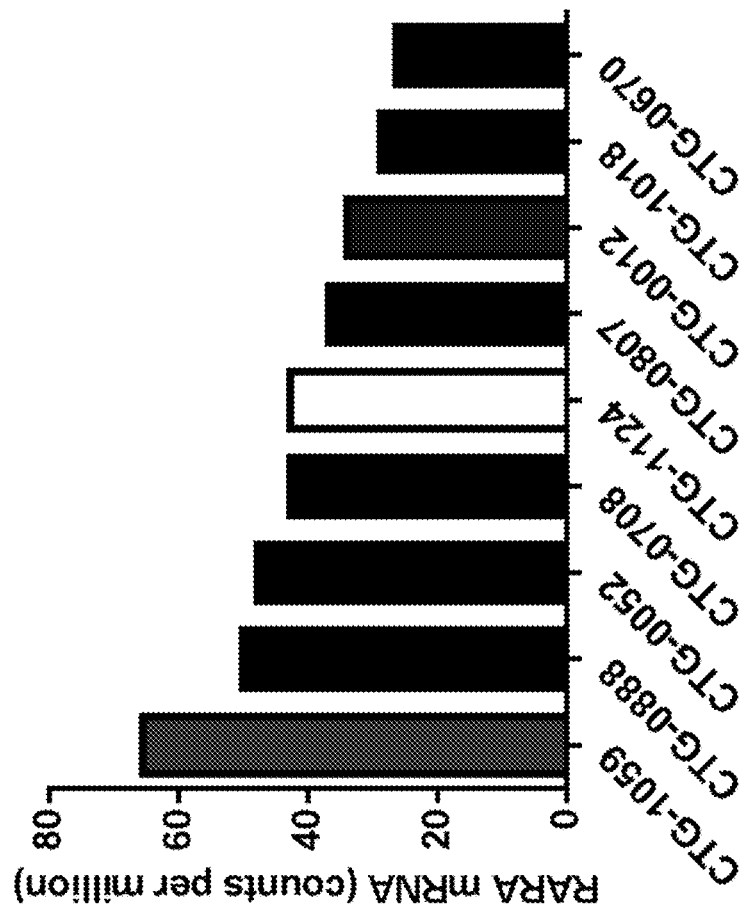
FIG. 22 depicts that RARA mRNA levels in nine different patient sample-derived mouse xenograft breast cancer models. The white bar represents both the value for CTG-1124, as well as the 55.3% prevalence cutoff in this population.

RARA mRNA levels in both of these PDXs, as well as 7 other breast cancer PDXs are determined using RNA-seq as described in Example 3. We assume that these 9 PDXs represent a population having a normal distribution of RARA mRNA levels and using the 55.3% prevalence cutoff as determined based on RARA SE strength ordinal, the tamibarotene-responsive CTG-1059 has a RARA mRNA level prevalence value above 55.3%, while the non-responsive CTG-0012 has a RARA mRNA level prevalence value below 55.3% (FIG. 22).

Example 9. RARA Super Enhancer Strength Ordinal Rank Cutoff in AML

Figure 23C:
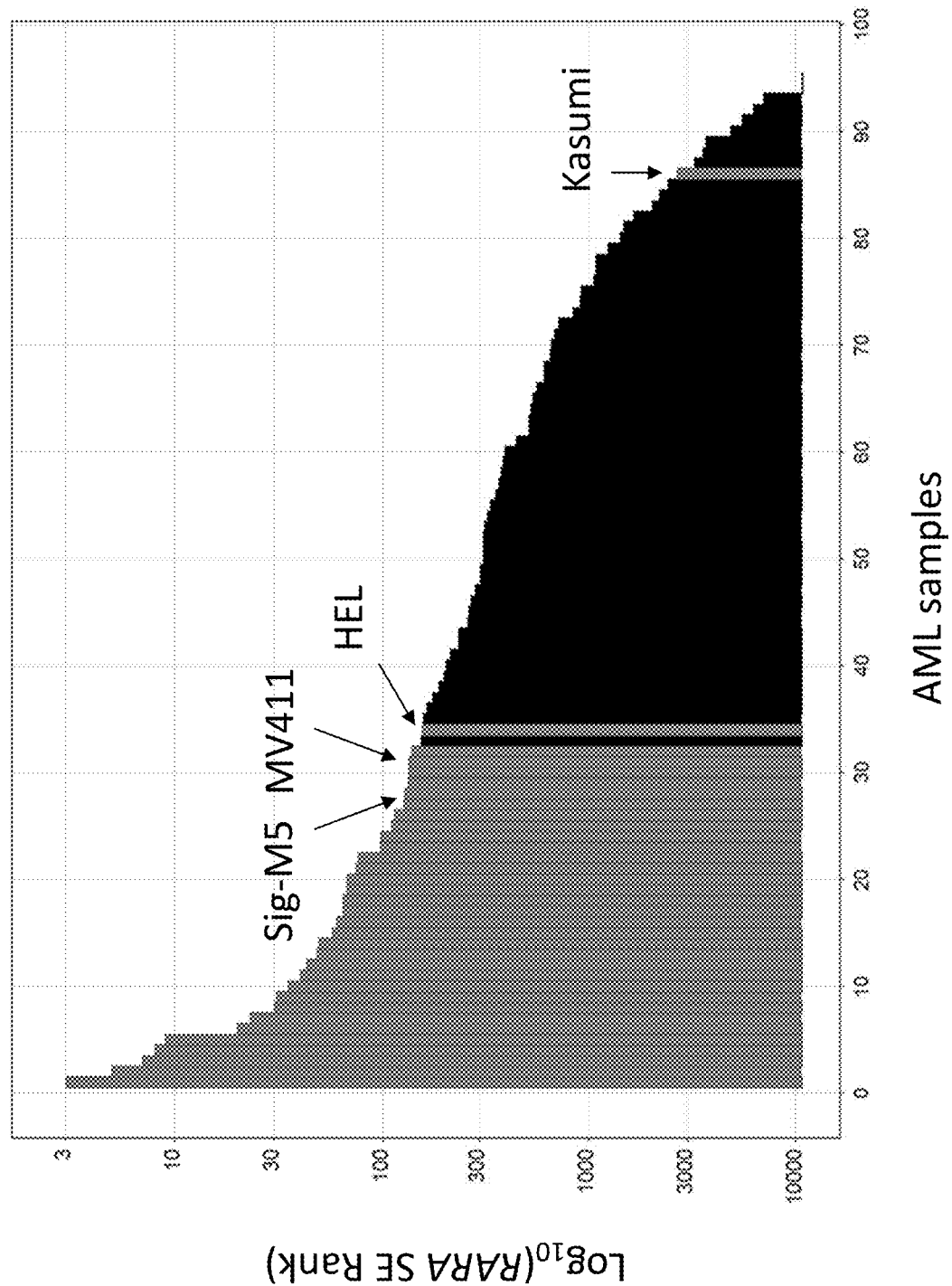
FIG. 23C depicts a $\log_{10}$ rank-ordered graph of RARA super enhancer strength ordinal in 94 AML samples including four of the six AML cell lines analyzed in FIGS. 20A and 20B—Sig-M5, MV411, HEL and Kasumi.

The total enhancer/super enhancer profile of 95 AML samples (both patient samples and AML cell lines, including SigM5, MV411, HEL and Kasumi) are analyzed using H3K27Ac and ChIP-Seq as described in Example 1. In each of the samples, the ordinal rank of the RARA-associated enhancer in terms of strength (as measured by H3K27Ac) is determined as compared to other enhancers and super-enhancers in the same cell and the determined ordinal ranks are plotted on a rank-order bar graph (FIGS. 23A-C). In MV411, it was determined that the RARA-associated enhancer was the 133$^{rd}$ strongest enhancer. MV411 is the confirmed tamibarotene-responsive cell line having the lowest super enhancer strength ordinal. In HEL, it was determined that the RARA-associated enhancer was the 155$^{th}$ strongest enhancer. HEL is the confirmed tamibarotene non-responsive cell line having the highest super enhancer strength ordinal. Based upon these values, we set the RARA enhancer strength ordinal cutoff at 150, a value in between the HEL ordinal and the MV411 ordinal.

Figure 24:
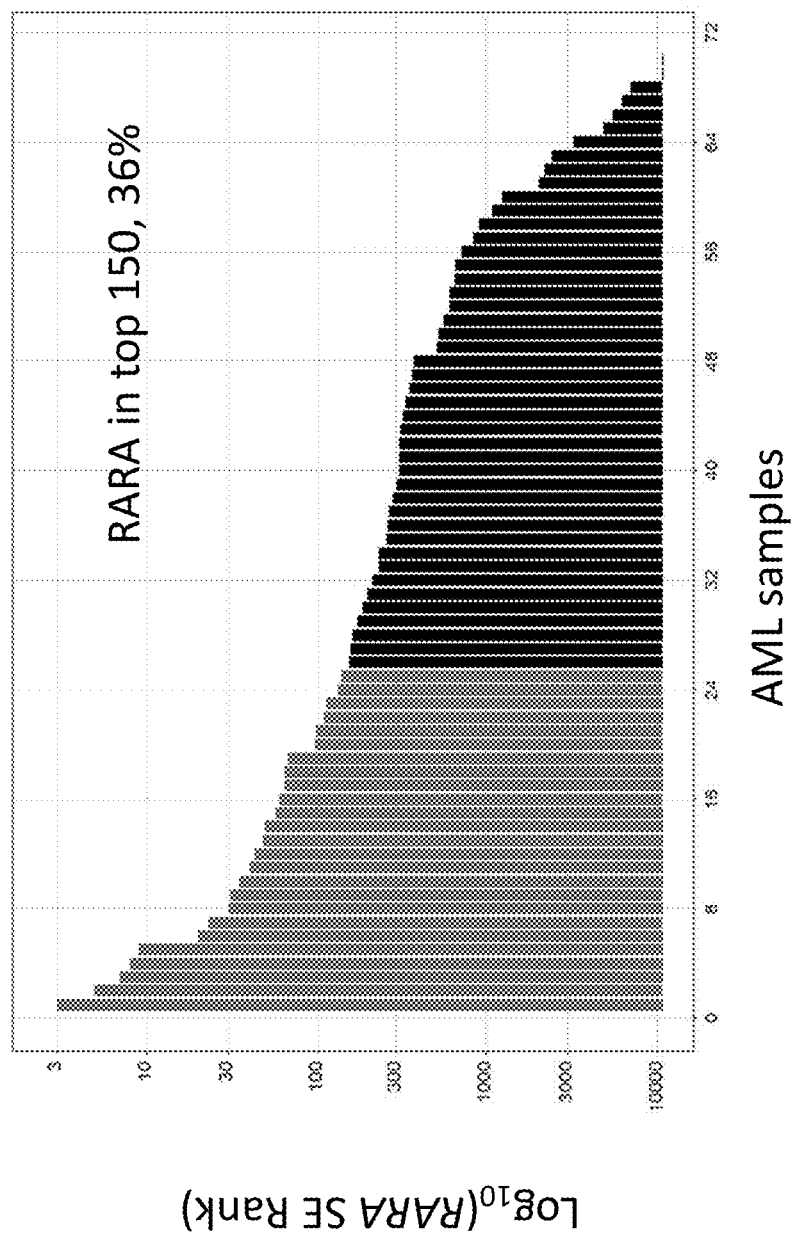
FIG. 24 depicts a $\log_{10}$ rank-ordered graph of RARA super enhancer strength ordinal in 70 AML patient samples. The lighter colored bars represent samples whose RARA super enhancer strength ordinal was equal to or above the prevalence cutoff. Darker colored bars represent samples whose RARA super enhancer strength ordinal was below the prevalence cutoff.

As determined from our analysis of 70 primary AML cell samples from human subjects, 36% of those samples had a RARA super enhancer that was at least the 150$^{th}$ strongest in those cells (FIG. 24). Therefore, we set the prevalence cutoff at 36%. That same prevalence cutoff is also used as the RARA mRNA prevalence cutoff when identifying potential AML responders to tamibarotene based on RARA mRNA measurements.

Figure 32:
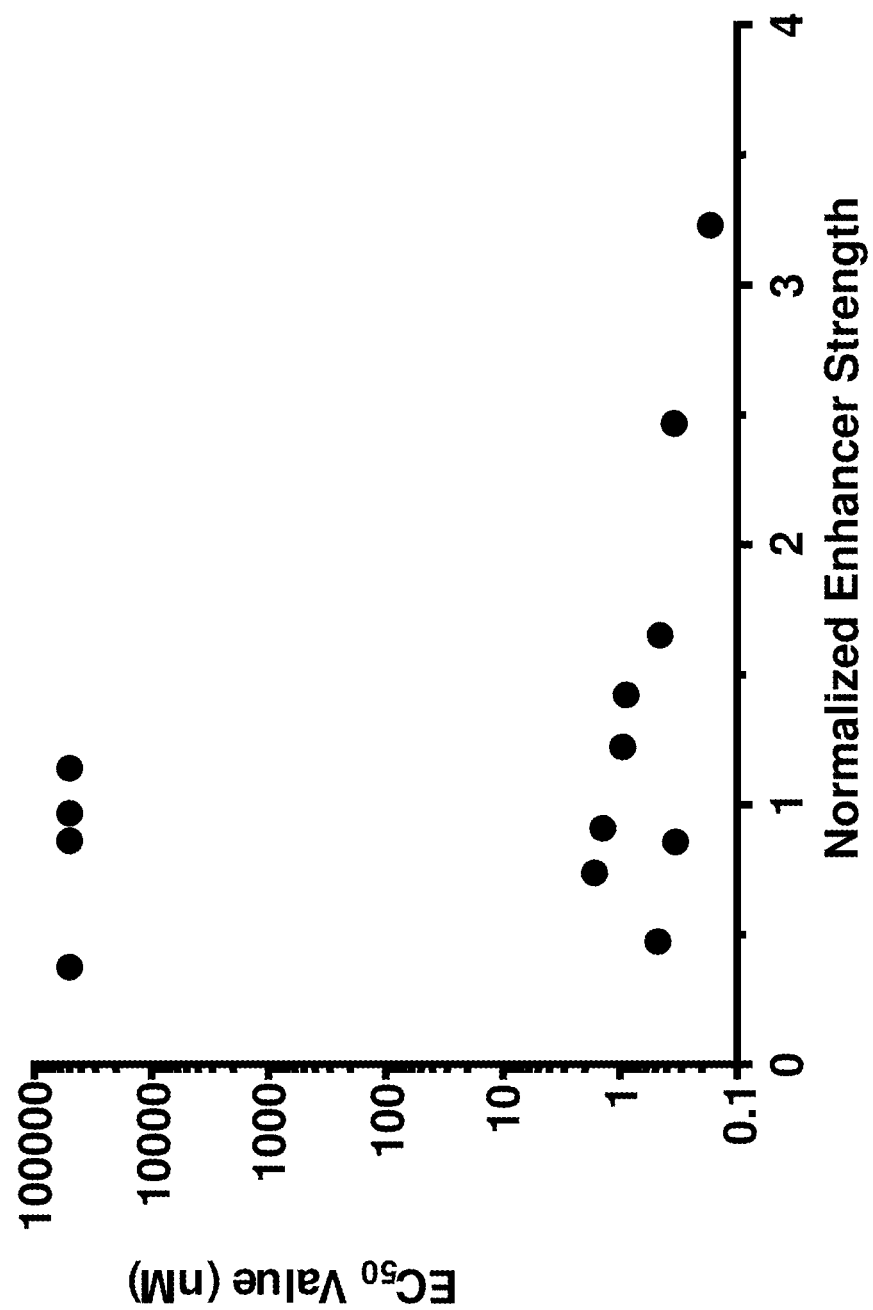
FIG. 32 depicts the correlation between RARA enhancer strength and sensitivity to tamibarotene in 11 different AML cell lines.

We also quantified the enhancers for an expanded panel of AML cell lines by ratio of RARA enhancer to MALAT1 enhancer. Plotting this enhancer strength ratio value against sensitivity to tamibarotene, we confirmed that 5 out of 6 cell lines bearing RARA enhancer strength ratios above 1 are responsive, while only 4 out of 7 cell lines bearing enhancers below this level are responsive (FIG. 32). When the cutoff is moved to RARA/MALAT enhancer ratio of 1.4 or higher, all of the cell lines (4 out of 4) are responsive.

Figure 25:
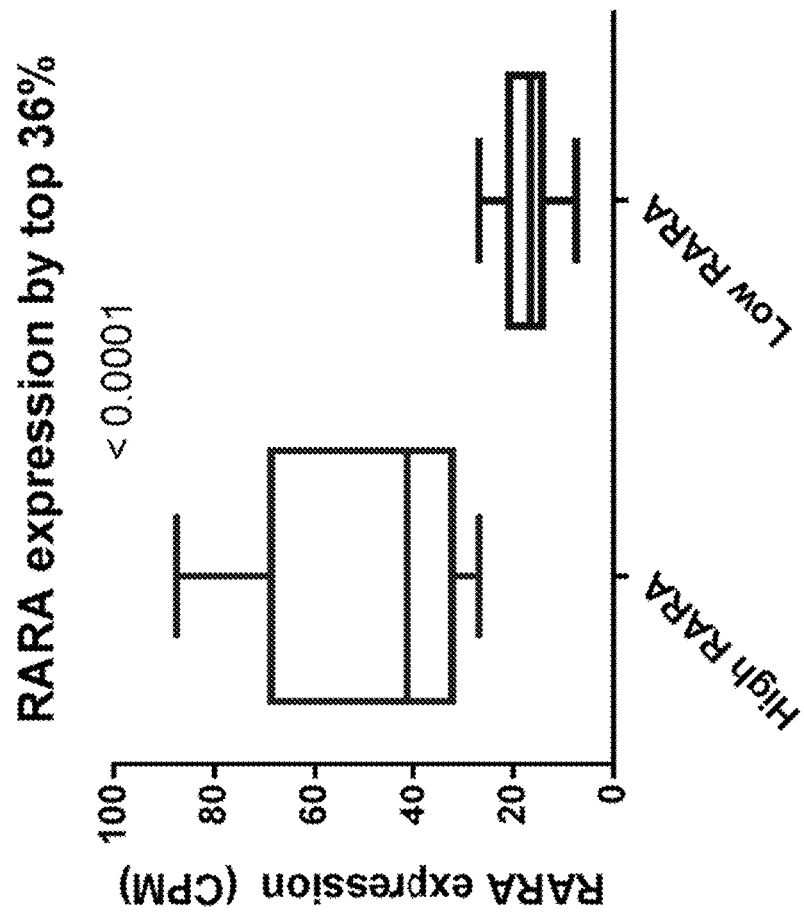
FIG. 25 depicts RARA mRNA levels in the 70 AML patient samples used in FIG. 24 and binned according to whether their RARA super enhancer strength ordinal was above (or equal to) the prevalence cutoff ("High RARA) or below the prevalence cutoff ("Low RARA").
Figure 26C:
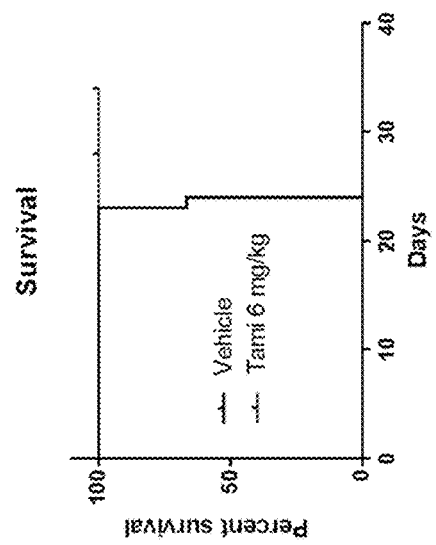
FIGS. 26C and 26F show the time of survival of the mouse models.
Figure 26B:
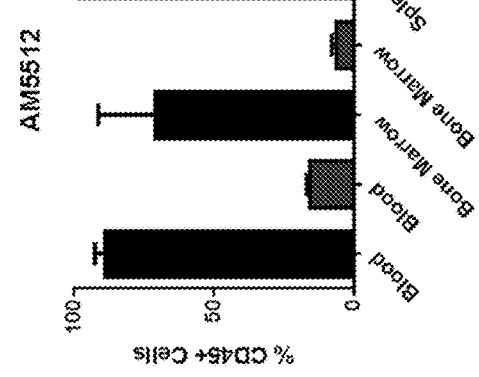
FIGS. 26B and 26E depict the % $CD45^+$ cells in different organs and biological fluids.
Figure 26A:
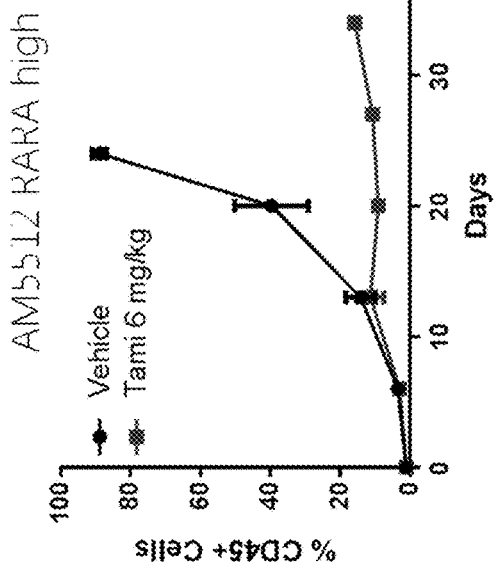
FIGS. 26A and 26D depict the response, as measured by % $CD45^+$ cells, to daily dosing of tamibarotene in two different patient-derived mouse xenograft AML models.
Figure 26F:
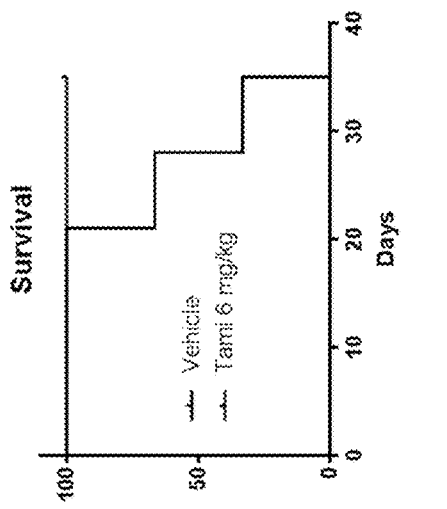
Figure 26E:
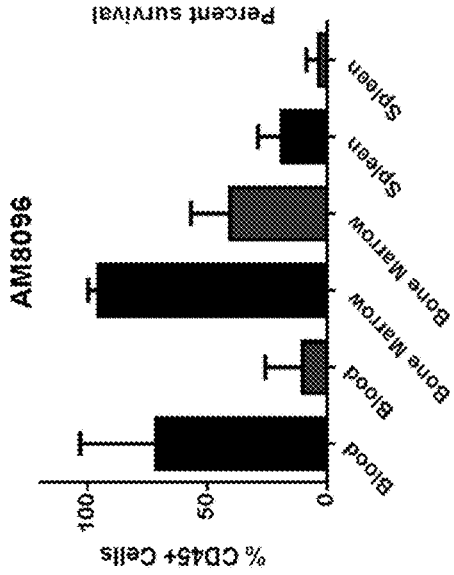
Figure 26D:
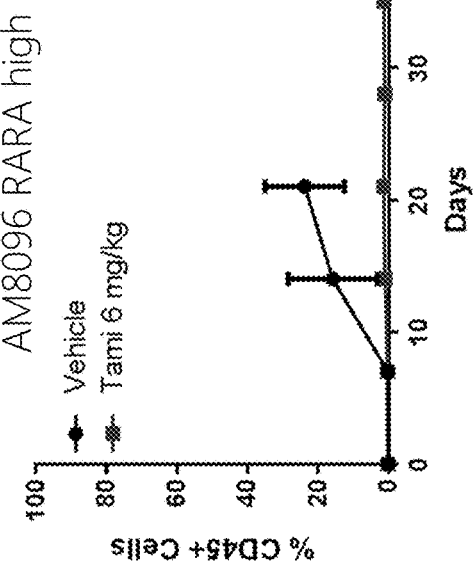
Figure 27C:
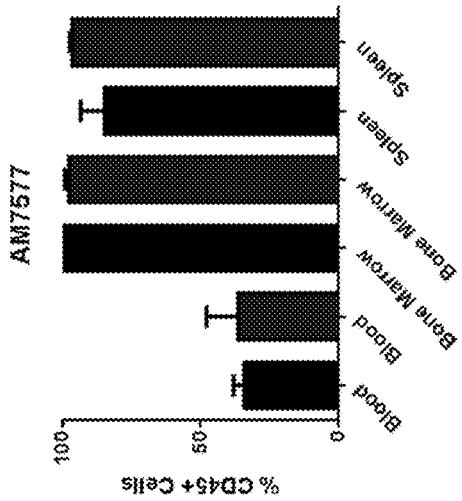
FIG. 27C depicts the % $CD45^+$ cells in different organs and biological fluids in one of those models.
Figure 27D:
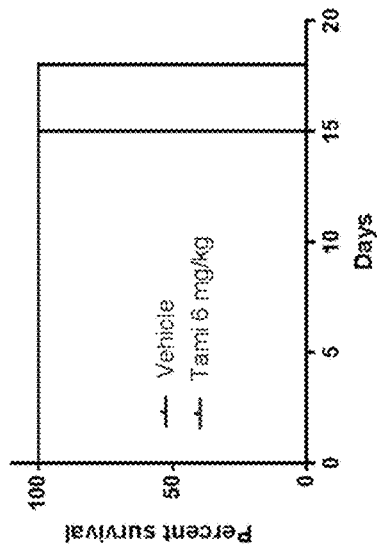
FIG. 27D depicts the time of survival in that model.
Figure 27A:
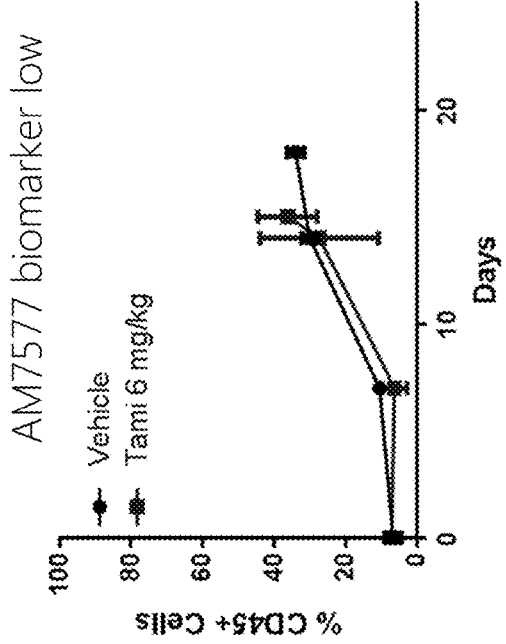
FIG. 27A-B depict the response, as measured by % $CD45^+$ cells, to daily dosing of tamibarotene in two additional patient-derived mouse xenograft AML models.
Figure 27B:
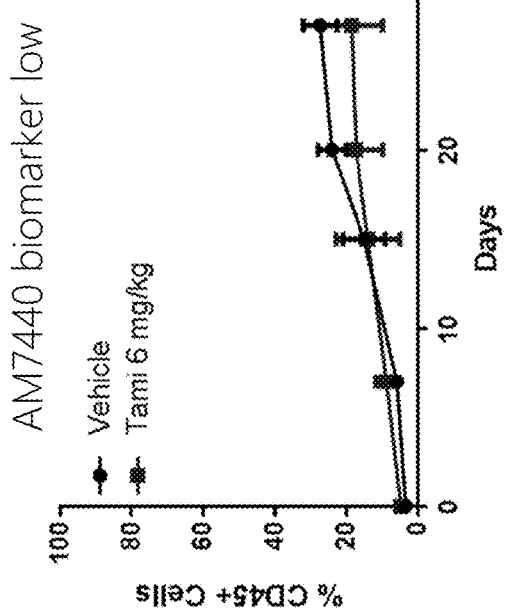

Example 10. RARA Super Enhancer Strength Ordinal Rank Cutoff in AML Correlates with RARA mRNA Levels The AML patient samples used to determine the 36% RARA super enhancer strength ordinal prevalence cutoff, are binned into two groups—those having a prevalence rank of 36% or higher (i.e., a lower % value) and those having a prevalence rank lower than 36% (i.e., a higher % value)—and assayed for RARA mRNA level using RNA-seq as described in Example 3. The results are shown in FIG. 25. The group at or higher than the 36% prevalence rank in RARA super enhancer strength ordinal has a statistically significant higher level of RARA mRNA than the group below the prevalence rank (p<0.001). This again confirmed that a prevalence cutoff determined at the super-enhancer level can also be used as the prevalence cutoff at the mRNA level.

Figure 33:
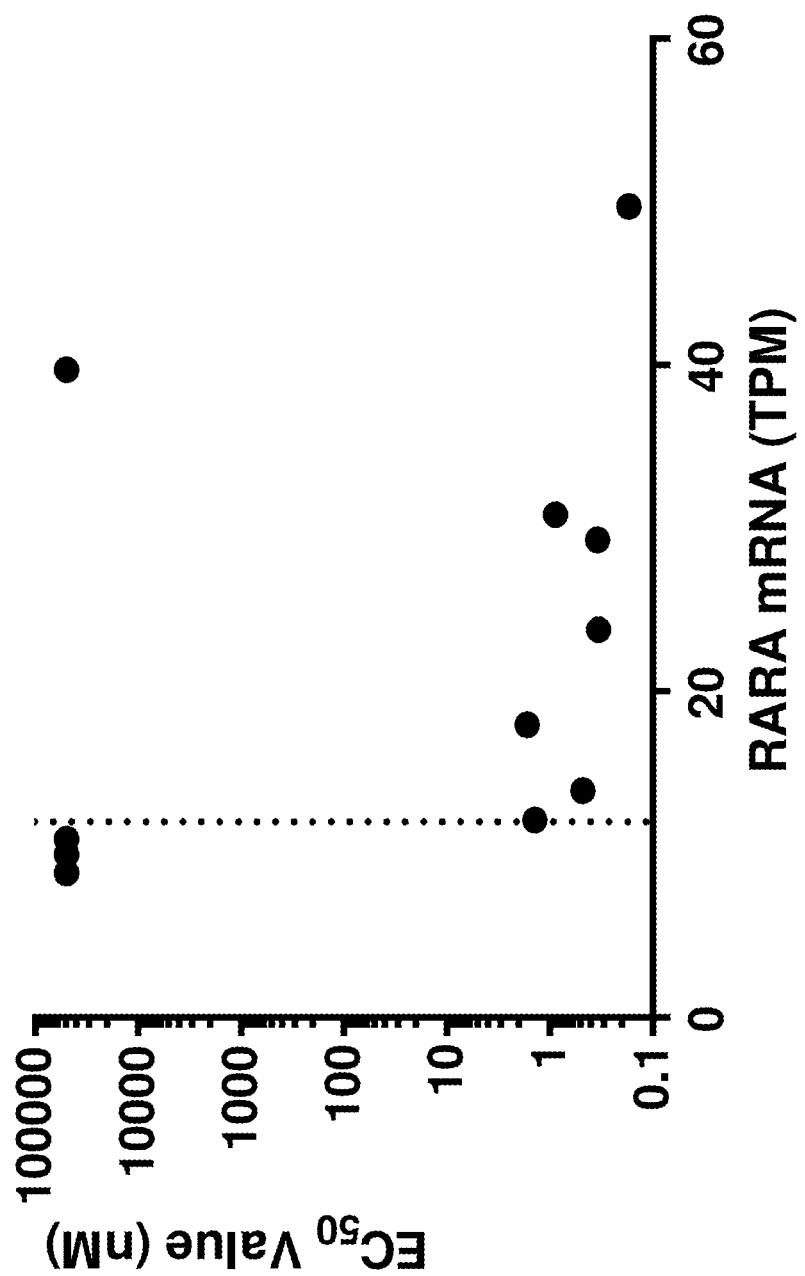
FIG. 33 depicts the correlation between RARA mRNA level and sensitivity to tamibarotene in 11 different AML cell lines.

We also determined the RARA mRNA levels in 11 different AML cell lines using RNA-seq and compared the mRNA levels to sensitivity to tamibarotene. The tested AML cell lines partitioned into two distinct groups based on their sensitivity or insensitivity to tamibarotene. Tamibarotene-sensitive cell lines all had RARA mRNA measured by RNAseq >10 TPM, while three insensitive cell lines had levels below this cut-off level (FIG. 33).

Example 11. Sensitivity of Various AML Patient Sample-Derived Xenografts to Tamibarotene Different AML patient sample (AM8096, AM5512, AM7577 and AM7440)-derived xenograft models in BALB/c nude immunocompromised mice are prepared by Crown Biosciences (Beijing, China) essentially as follows.

Approximately 2×10$^6$ cells from each patient sample are suspended in 100 μL PBS and injected into separate mice (n=3 for each different patient sample and for the control) by IV tail injection. For AM5512, AM7577 and AM7440 xenografts, tumor burden is considered high enough to start treatment when the concentration of human CD45$^+$ cells reaches ~1-5% in the animal's peripheral blood. Human CD45$^+$ cells are detected in mouse blood (obtained via eye bleeds) using a fluorescence activated cell sorter and FITC anti-human CD45 (Biolegend, Cat #304037). For AM8096 xenografts, treatment is begun 40 days after injection of cells.

Tamibarotene is administered orally in pH 8 adjusted PBS, 1% DMSO on a daily schedule at a final dose of 6 mg per kg body weight in a 10 ml/kg volume. Mice in the vehicle arm are given the same schedule, volume, and formulation, but lacking tamibarotene. Human CD45$^+$ cell levels in peripheral blood from the treated animals and control animals are measured once a week.

AM5512 and AM8096 xenografts show a significant reduction in the total % of CD45$^+$ cells, as well as in the % of CD45$^+$ cells in blood, bone marrow and spleen, when treated with tamibarotene as compared to the vehicle control after 35 days of treatment (FIGS. 26A-F). On the other hand, AM7577 and AM7440 show no significant reduction in tumor volume between the tamibarotene treated and vehicle treated animals either overall or in any of blood, bone marrow or spleen (FIGS. 27A-D).

Figure 28:
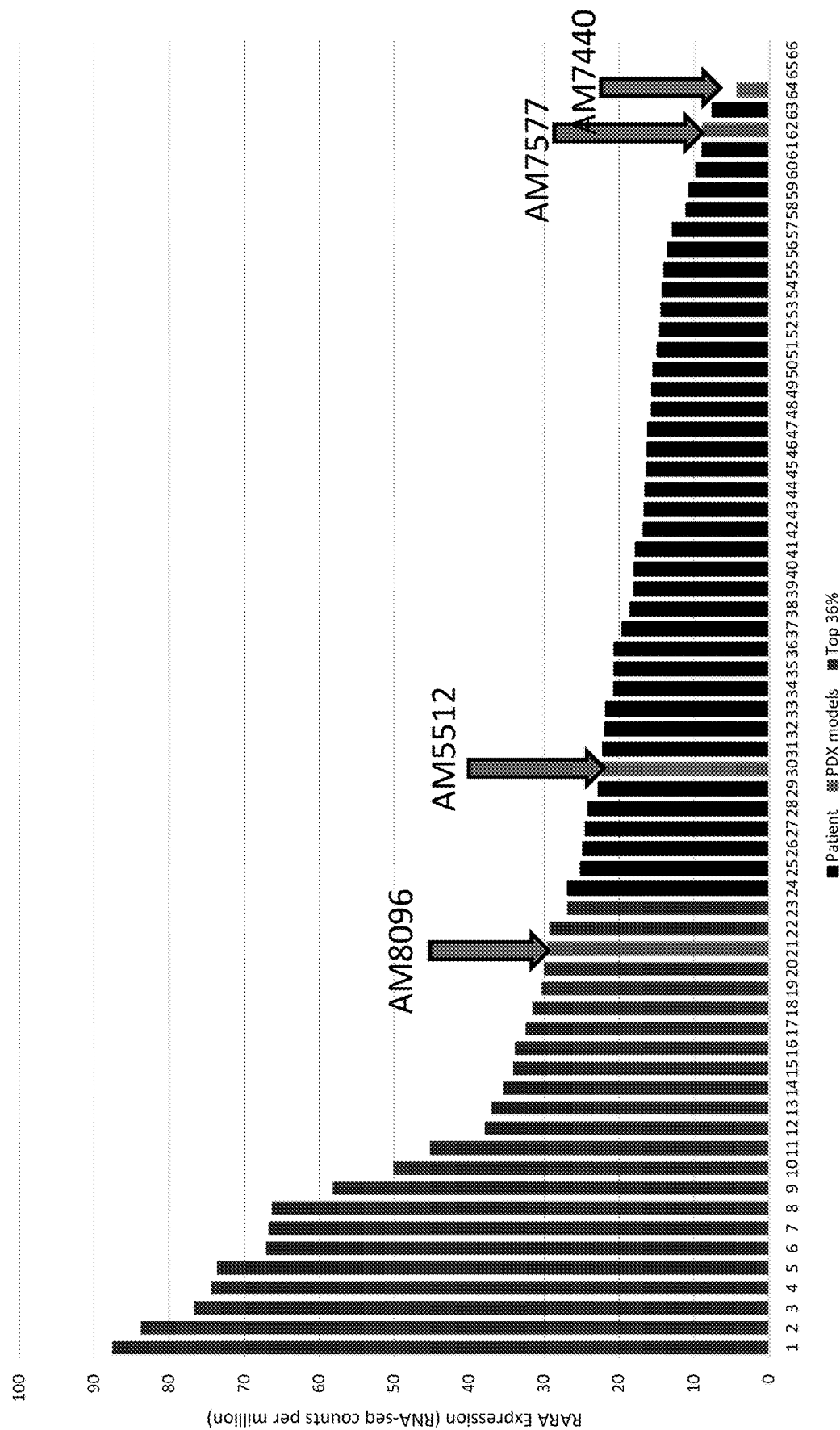
FIG. 28 depicts the RARA mRNA levels in 64 AML patient samples, including the four used to create mouse xenograft models (see FIGS. 26A-26F and FIGS. 27A-27D). The lighter colored bars represent samples whose RARA mRNA was equal to or above the prevalence cutoff as determined from RARA super enhancer strength ordinal. Darker colored bars represent samples whose RARA mRNA level was below that prevalence cutoff.

FIG. 28 shows a rank ordering of RARA mRNA levels from individual patient samples used in the binning analysis shown in FIG. 25. In addition, FIG. 28 includes the RARA mRNA levels of each of the patient samples used in the xenograft study. The two non-responders in the xenograft study, AM7577 and AM7440, have RARA mRNA levels that fall well below the 36% prevalence cutoff. One of the responders, AM8096, has a RARA mRNA level that is above the 36% prevalence cutoff. The other responder, AM5512, falls slightly below the 36% prevalence cutoff (46.9% prevalence value). These RARA mRNA results suggest that the prevalence cutoff could be adjusted downward (e.g., to 46.9%) to maximize the number of potential responders.

Example 12. AM5512 is Sensitive to Tamibarotene but not ATRA

Figure 29B:
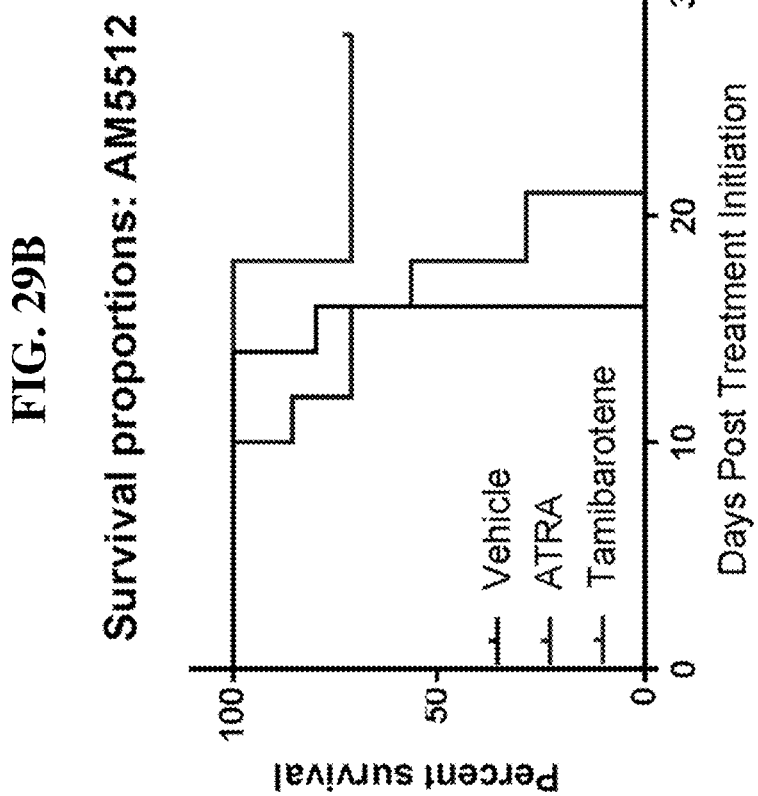
FIG. 29B depicts the survival rate of such mice during the course of the experiment.
Figure 29A:
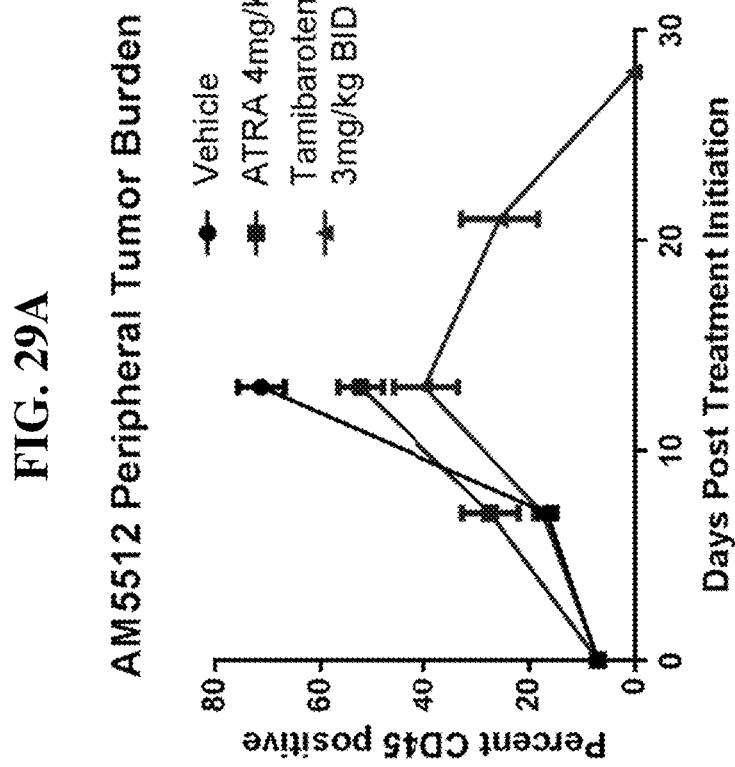
FIG. 29A depicts the response of AM5512 xenograft mice to 4 mg/kg ATRA BID, 3 mg/kg tamibarotene BID and a vehicle control as measured by % $CD45^+$ cells.

AM5512 xenograft mice are prepared as described above. When the concentration of human CD45$^+$ cells reach ~1-5% in the animal's peripheral blood, they are treated with either tamibarotene (n=7; 3 mg/kg, BID), all-trans retinoic acid (ATRA; n=7; 4 mg/kg BID) or a vehicle control (n=5). While tamibarotene is a RARA-specific agonist, ATRA agonizes all retinoic acid receptors (RAR-α, RAR-ß and RAR-γ). As shown in FIGS. 29A-B, AM5512 xenograft mice treated with tamibarotene show a significant reduction in % CD45$^+$ cells after 28 days of treatment as compared to both vehicle control and ATRA-treated animals and 5 of the 7 animals survive the course of the experiment. Surprisingly, while AM5512 xenograft mice treated with ATRA show a reduction in % CD45$^+$ cells as compared to the vehicle control after 14 days of treatment, none of those mice survived past day 21.

Example 13. Subsets of Patient Samples with Other Cancers have High Levels of RARA mRNA For a number of different cancer types, we use RARA mRNA level z-scores provided by TCGA as described in Example 3. In a normal distribution of a population, 5% of samples should have a RARA mRNA level that is greater than 2 standard deviations from the mean. FIG. 30 is a table showing those specific cancer types having greater than 5% of samples with RARA mRNA levels greater than 2 standard deviations from the mean. Without being bound by theory, we believe that each of these cancers will be susceptible to the stratification and treatment methods set forth herein.

Figure 31:
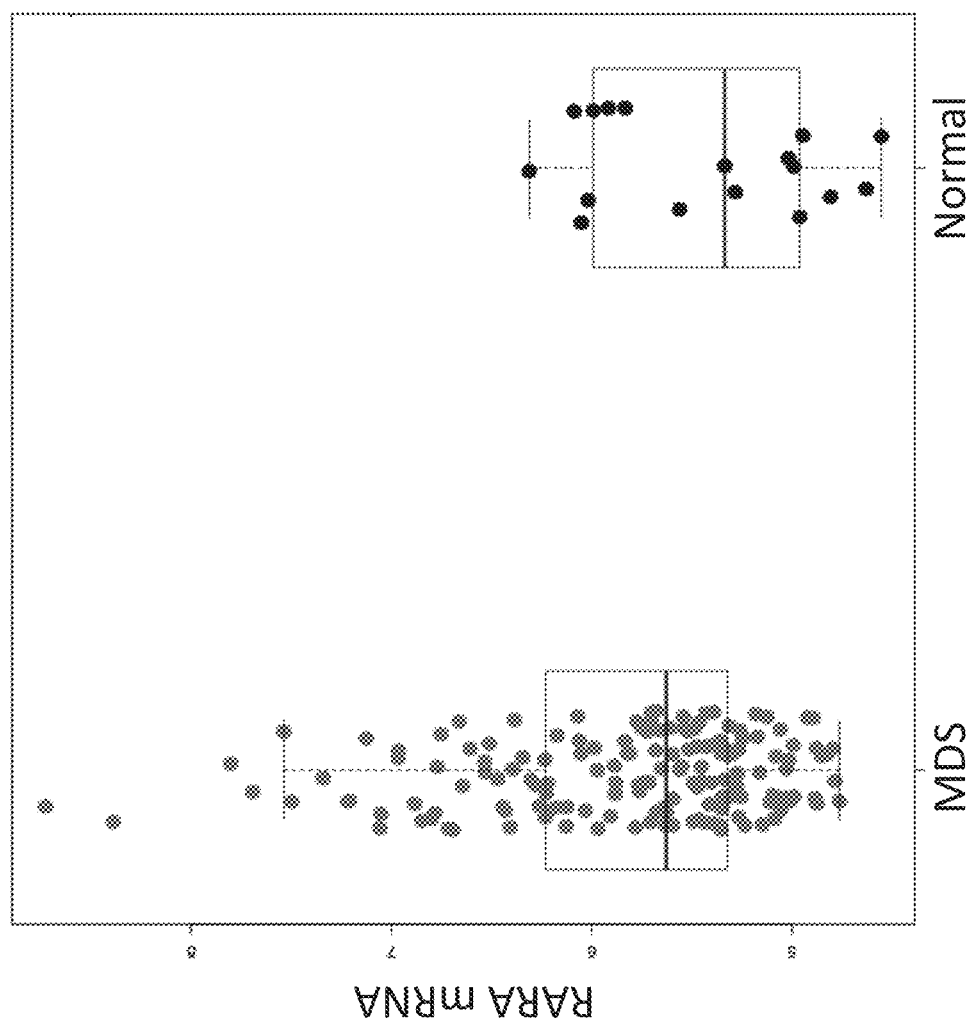
FIG. 31 depicts RARA mRNA levels in MDS patient samples versus cells from healthy ("Normal") patients.

We also look specifically at samples from patients suffering from myelodysplastic syndrome, which is believed to be a cancer closely related to AML. RARA mRNA levels from 176 patients (17 normal; 159 MDS) are obtained as described in Example 3. The samples are binned based on disease state and RARA mRNA levels plotted as shown in FIG. 31. Statistical analysis of the results (T-test) show that RARA mRNA levels are significantly elevated in MDS patients samples as compared to normal patient samples (p=0.08751).

To further validate the presence of elevated RARA in MDS, ChIP-seq H3K27ac enhancer analysis was performed on bone marrow samples collected from two MDS patients. For both of these patients, the RARA gene locus had a markedly stronger H3K27ac signal in the two MDS patient bone marrow samples, compared to the signal found in the blast cells of healthy donors. The strength of the RARA super-enhancer in the MDS patients was similar to that in blasts from the subset of AML patients that have strong RARA super-enhancers and high levels of RARA mRNA. Furthermore, the RARA super-enhancer in the MDS patient cells had a high RARA enhancer strength ordinal (9 and 60, respectively) compared to blast and immature cell types from healthy subjects.

Without being bound by theory, we believe that MDS patients will also be susceptible to the stratification and treatment methods set forth herein.

EQUIVALENTS AND SCOPE

In the embodiments articles such as "a," "an," and "the" may mean one or more than one unless indicated to the contrary or otherwise evident from the context. Embodiments or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed embodiments is introduced into another embodiment. For example, any embodiment that is dependent on another embodiment can be modified to include one or more limitations found in any other embodiment that is dependent on the same base embodiment. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the embodiments. Because such embodiments are deemed to be known to one of ordinary skill in the art, they may be excluded even if the exclusion is not set forth explicitly herein. Any particular embodiment of the invention can be excluded from any embodiment, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended embodiments. Those of ordinary skill in the art will appreciate that various changes and modifications to this description may be made without departing from the spirit or scope of the present invention, as defined in the following embodiments.

The invention claimed is:

1. A method of treating non-acute promyelocytic leukemia acute myelogenous leukemia (non-APL AML) in a subject, the method comprising administering a therapeutically effective amount of tamibarotene to the subject, wherein, prior to administration, a sample of diseased cells from the subject is determined to have
   (a) a super enhancer associated with a retinoic acid receptor alpha (RARA) gene, wherein the super enhancer has a strength or ordinal rank that is equal to or above a pre-determined threshold level, or
   (b) a level of primary RNA transcripts from the RARA gene and/or a portion of the super enhancer associated therewith, wherein the level of the RNA transcripts is equal to or above a pre-determined threshold, and wherein the RNA transcripts are transcribed from a RARA gene that encodes a functional RARA and specifically excludes gene fusions that comprise all or a portion of the RARA gene.

2. The method of claim 1, wherein the pre-determined threshold is a cutoff value.

3. The method of claim 2, wherein the cutoff value is set at a value that is equal to or up to 5% above the level of primary RNA transcripts from the RARA gene in the lowest responder in a population of non-APL AML test samples.

4. The method of claim 3, wherein the population of test samples comprises samples obtained from human subjects, cell lines, or patient-derived xenografts.

5. The method of claim 4, wherein the cutoff value is the level of primary RNA transcripts in xenograft AM5512.

6. The method of claim 1, wherein the level of the primary RNA transcripts from the RARA gene, in the sample, is determined using qPCR, fluorescent hybridization, RNA sequencing, RNA hybridization and signal amplification, or northern blot.

7. The method of claim 1, wherein the subject is a human subject.

8. The method of claim 7, wherein the human subject is an elderly unfit subject.

9. The method of claim 1, wherein the subject has a relapsed or refractory form of the non-APL AML.

10. The method of claim 1, wherein the sample of diseased cells from the subject has been determined to have a super enhancer associated with the RARA gene, wherein the super enhancer has a strength or ordinal rank that is equal to or above a pre-determined threshold level.

11. The method of claim 10, wherein the super enhancer has (i) a strength corresponding to a prevalence rank that is equal to or above a pre-determined prevalence cutoff for RARA gene super enhancer strength; (ii) a strength that is equal to or above a pre-determined RARA gene strength cutoff; (iii) an ordinal of strength corresponding to a prevalence rank that is equal to or above a pre-determined RARA gene strength ordinal prevalence cutoff; and/or (iv) an ordinal of strength that is equal to or above a pre-determined RARA gene strength ordinal cutoff.

12. The method of claim 11, wherein the cutoff value is set at a value that is (i) equal to or up to 5% above the RARA enhancer strength in the lowest responder in a population of cell samples; (ii) equal to or up to 5% above the RARA enhancer strength in the highest non-responder in the population; or (iii) a value in between the RARA enhancer strength of the lowest responder and the highest non-responder in the population.

13. The method of claim 12, wherein the population of cell samples comprises samples obtained from human subjects, cell lines, or patient-derived xenografts.

14. The method of claim 11, wherein the cutoff value is the super enhancer strength or ordinal rank in xenograft AM5512.

15. The method of claim 10, wherein the subject is a human subject.

16. The method of claim 15, wherein the human subject is an elderly unfit subject.

17. The method of claim 10, wherein the subject has a relapsed or refractory form of the non-APL AML.

18. The method of claim 1, wherein the sample of diseased cells from the subject has been determined to have a level of the RNA transcripts from the RARA gene and/or a portion of the super enhancer associated therewith, wherein the level of RNA transcripts is equal to or above a pre-determined threshold.

19. The method of claim 18, wherein the RNA transcripts from the RARA gene are mRNA transcripts.

20. The method of claim 19, wherein the mRNA transcripts are expressed at a level that (i) is equal to or above a pre-determined mRNA level cutoff; and/or (ii) corresponds to a prevalence rank that is equal to or above a pre-determined RARA mRNA prevalence cutoff.

21. The method of claim 20, wherein the cutoff value is set at a value that is equal to or up to 5% above the level of mRNA transcripts from the RARA gene in the lowest responder in a population of non-APL AML test samples.

22. The method of claim 21, wherein the population of cell samples comprises samples obtained from human subjects, cell lines, or patient-derived xenografts.

23. The method of claim 22, wherein the cutoff value is the level of mRNA transcripts from the RARA gene in xenograft AM5512.

24. The method of claim 19, wherein the level of mRNA transcripts from the RARA gene, in the sample, is determined using qPCR, fluorescent hybridization, RNA sequencing, RNA hybridization and signal amplification, or northern blot.

25. The method of claim 19, wherein the subject is a human subject.

26. The method of claim 25, wherein the human subject is an elderly unfit subject.

27. The method of claim 19, wherein the subject has a relapsed or refractory form of the non-APL AML.

\* \* \* \* \*